(12) United States Patent
Yoshida et al.

(10) Patent No.: US 11,401,264 B2
(45) Date of Patent: Aug. 2, 2022

(54) HETEROCYCLIC COMPOUND

(71) Applicant: Orizuru Therapeutics, Inc., Fujisawa (JP)

(72) Inventors: Yoshinori Yoshida, Kyoto (JP); Kenji Miki, Kyoto (JP); Akira Kaieda, Kanagawa (JP); Shigeru Kondo, Kanagawa (JP); Hiroshi Nara, Kanagawa (JP); Yoshinori Ikeura, Kanagawa (JP)

(73) Assignee: Orizuru Therapeutics, Inc., Kanagawa (JP)

( * ) Notice: Subject to any disclaimer, the term of this patent is extended or adjusted under 35 U.S.C. 154(b) by 0 days.

(21) Appl. No.: 17/043,162

(22) PCT Filed: Mar. 28, 2019

(86) PCT No.: PCT/JP2019/013529
§ 371 (c)(1),
(2) Date: Sep. 29, 2020

(87) PCT Pub. No.: WO2019/189553
PCT Pub. Date: Oct. 3, 2019

(65) Prior Publication Data
US 2021/0024512 A1    Jan. 28, 2021

(30) Foreign Application Priority Data
Mar. 30, 2018 (JP) .............................. JP2018-069872

(51) Int. Cl.
*C07D 409/14* (2006.01)
*C07D 403/04* (2006.01)

(52) U.S. Cl.
CPC ......... *C07D 409/14* (2013.01); *C07D 403/04* (2013.01)

(58) Field of Classification Search
CPC .......................... C07D 409/14; C07D 403/04
See application file for complete search history.

(56) References Cited

U.S. PATENT DOCUMENTS

| | | |
|---|---|---|
| 5,591,762 A | 1/1997 | Hauel et al. |
| 5,594,003 A | 1/1997 | Hauel et al. |
| 5,602,127 A | 2/1997 | Hauel et al. |
| 5,614,519 A | 3/1997 | Hauel et al. |
| 2007/0010012 A1 | 1/2007 | Gold et al. |
| 2011/0104122 A1 | 5/2011 | Yamashita et al. |
| 2013/0183753 A1 | 7/2013 | Nakatsuji et al. |
| 2014/0127807 A1 | 5/2014 | Nakatsuji et al. |
| 2015/0284684 A1 | 10/2015 | Gold et al. |
| 2016/0122718 A1 | 5/2016 | Braam |
| 2017/0152485 A1 | 6/2017 | Nakatsuji et al. |

FOREIGN PATENT DOCUMENTS

| | | |
|---|---|---|
| DE | 42 12 748 A1 | 10/1993 |
| JP | 04-346978 A | 12/1992 |
| JP | 2016-521571 A | 7/2016 |
| JP | 2017-060422 A | 3/2017 |
| WO | WO-2007/002136 A2 | 1/2007 |
| WO | WO-2009/118928 A1 | 10/2009 |
| WO | WO-2012/026491 A1 | 5/2012 |
| WO | WO-2015/182765 A1 | 12/2015 |

OTHER PUBLICATIONS

Laflamme et al., "Cardiomyocytes derived from human embryonic stem cells in pro-survival factors enhance function of infarcted rat hearts", Nature Biotechnology, Sep. 2007, 25(9):1015-1024.
Yan et al., "Cyclosporin-A potently induces highly cardiogenic progenitors from embryonic stem cells," Biochemical and Biophysical Research Communications, 2009, 379:115-120.
Yang et al., "Human cardiovascular progenitor cells develop from a KDR embryonic-stem-cell-derived population," Nature, May 22, 2008, 453(7194):524-528.

*Primary Examiner* — Timothy R Rozof
(74) *Attorney, Agent, or Firm* — Foley & Lardner LLP

(57) ABSTRACT

The present invention provides a heterocyclic compound having an activity to promote the maturation of a cardiomyocyte.

A compound represented by the formula (I):

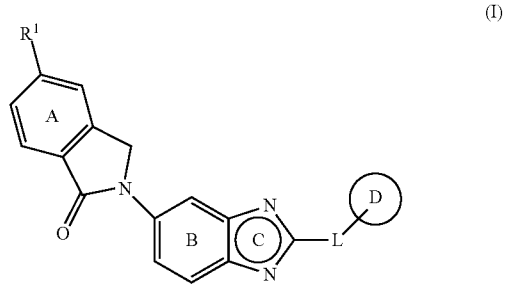

(I)

wherein each symbol is as defined in the description, or a salt thereof has an activity to promote the maturation of a cardiomyocyte, and is useful as a cardiomyocyte maturation promoter.

43 Claims, 5 Drawing Sheets
Specification includes a Sequence Listing.

HETEROCYCLIC COMPOUND

TECHNICAL FIELD

The present invention relates to a heterocyclic compound, particularly a heterocyclic compound having an activity to promote the maturation of a cardiomyocyte, and a preparation method of mature cardiomyocytes.

BACKGROUND OF THE INVENTION

Cardiac diseases are the leading cause of death in the world. Cardiac transplantation, which is currently the sole therapeutic option for severe heart failure patients, suffers from donor shortage. A potential therapeutic option as an alternative to cardiac transplantation is transplantation of cardiomyocytes derived from pluripotent stem cells (e.g., iPS cells (induced pluripotent stem cells), ES cells (embryonic stem cells), etc.). The alternative option has been desired to be developed promptly. Moreover, cardiomyocytes derived from pluripotent stem cells (e.g., iPS cells, ES cells, etc.) are also required as cells used for drug toxicity tests and cardiac disease model studies.

Improvement of efficiency and safety is essential to apply iPS cell-derived mature cardiomyocytes to regenerative medicine. Regarding efficiency, there is a problem of low cost efficiency, because the number of cardiomyocytes capable of inducing maturation is small and proteins such as growth factors in a culture medium are very expensive. Regarding safety, there is a problem that cardiomyocytes have a low purity, and proliferative cells other than the cardiomyocytes can be contaminated, so that there is a risk of canceration.

Moreover, for drug toxicity tests and cardiac disease model studies using cardiomyocytes, it is necessary to collect a large number of mature cardiomyocytes that sufficiently mimic cardiomyocytes in the living body. Cardiomyocytes lose their division potential at the same time as the birth, and regeneration of those cells is very difficult. Because of such properties, a number of studies have been carried out for inducing differentiation of pluripotent stem cells into cardiomyocytes in order to obtain a large number of cardiomyocytes (Patent Document 1, Patent Document 2, Non-patent Document 1, Non-patent Document 2 and Non-patent Document 3).

However, in general, it is said that cardiomyocytes derived from human pluripotent stem cells stay in an immature stage similar to fetal cardiomyocytes, and that their ion channel function is insufficient compared to adult cardiomyocytes. Thus, for the purpose of screening of drug toxicity and therapeutic agents in relation to ion channels, mature cardiomyocytes are required to be used.

Therefore, mature cardiomyocytes and a preparation method thereof are required as cells used for cardiomyocyte transplantation and for screening of drug toxicity and therapeutic drug.

Patent Document 3 reports on the compound represented by the following formula

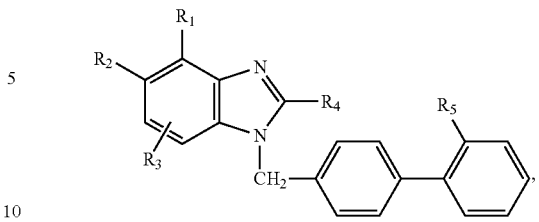

wherein each symbol is as defined above,
as a benzimidazole derivative useful for treatment of cardiac disease, lung disease or central nervous system disorder (e.g., Alzheimer's disease, ischemic disease).

It is possible to obtain mature cardiomyocytes by culturing immature cardiomyocytes for a long period (for example, 1 year or more). However, as a commercial preparation method of mature cardiomyocytes, such method takes too much time and requires expensive medium and medium additive.

Therefore, development of low molecular compounds having an activity to promote the maturation of a cardiomyocyte, which can efficiently prepare mature cardiomyocytes with high purity in a short period at low cost, is still desired.

DOCUMENT LIST

Patent Document

Patent Document 1: WO 2007/002136
Patent Document 2: WO 2009/118928
Patent Document 3: DE 4212748

Non-Patent Document

Non-Patent Document 1: Yan P, et al, Biochem Biophys Res Commun. 379:115-20 (2009)
Non-Patent Document 2: Laflamme M A, et al, Nat Biotechnol, 25:1015-1024 (2007)
Non-Patent Document 3: Yang L et al, Nature, 453:524-528 (2008)

SUMMARY OF THE INVENTION

Problems to be Solved by the Invention

The present invention aims to provide low molecular compounds have an activity to promote the maturation of a cardiomyocyte, which can efficiently prepare mature cardiomyocytes with high purity in a short period at low cost.

Means of Solving the Problems

The present inventors have found that the compound represented by the following formula (I) or a salt thereof (in the present specification, sometimes to be referred to as compound (I)) has an activity to promote the maturation of a cardiomyocyte. As a result of further studies, they have completed the present invention.

Accordingly, the present invention is as follows.

[1] A compound represented by the formula (I):

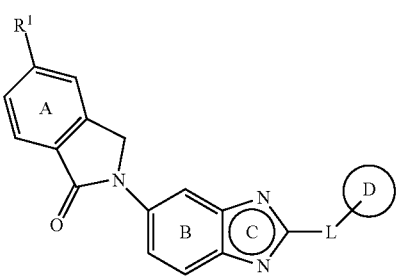

wherein
Ring A and Ring B are each independently an optionally further substituted benzene ring,
Ring C is an imidazole ring optionally further substituted by $C_{1-6}$ alkyl group (s) optionally substituted by 1 to 3 substituents selected from
  (1) a halogen atom,
  (2) a nitro group,
  (3) a cyano group,
  (4) an amino group,
  (5) a hydroxy group, and
  (6) an optionally halogenated $C_{1-6}$ alkoxy group,
L is a bond or an optionally substituted methylene group,
$R^1$ is a hydrogen atom or a substituent, and
Ring D is an optionally further substituted ring, or a salt thereof (hereinafter, to be referred to as compound (I)).

[2] The compound or salt of the above-mentioned [1], wherein, in the formula (I),
Ring A is a benzene ring;
Ring B is a benzene ring;
Ring C is an imidazole ring optionally further substituted by $C_{1-6}$ alkyl group (s);
L is a bond or a methylene group;
$R^1$ is
  (1) a hydrogen atom,
  (2) a halogen atom,
  (3) a mono- or di-$C_{1-6}$ alkylamino group,
  (4) a 5- to 14-membered aromatic heterocyclic group, or
  (5) a 3- to 14-membered non-aromatic heterocyclic group optionally substituted by 1 to 3 $C_{1-6}$ alkyl groups; and
Ring D is
(1) a benzene ring optionally further substituted by 1 to 3 substituents selected from
  (a) a halogen atom,
  (b) a hydroxy group,
  (c) a $C_{1-6}$ alkyl group optionally substituted by 1 to 3 $C_{1-6}$ alkoxy groups,
  (d) a $C_{1-6}$ alkoxy group optionally substituted by 1 to 3 substituents selected from
    (i) a carboxy group,
    (ii) a $C_{1-6}$ alkoxy-carbonyl group,
    (iii) a $C_{7-16}$ aralkyloxy-carbonyl group,
    (iv) a carbamoyl group optionally mono- or di-substituted by substituent(s) selected from
      (I) $C_{1-6}$ alkyl group optionally substituted by 1 to 3 substituents selected from
        (A) a $C_{3-10}$ cycloalkyl group,
        (B) a $C_{6-14}$ aryl group,
        (C) a $C_{6-14}$ arylamino group optionally substituted by 1 to 3 halogen atoms,
        (D) a 5- to 14-membered aromatic heterocyclic group,
        (E) a 3- to 14-membered non-aromatic heterocyclic group, and
        (F) a carbamoyl group optionally mono- or di-substituted by substituent(s) selected from a $C_{1-6}$ alkyl group and a $C_{7-16}$ aralkyl group,
      (II) a $C_{2-6}$ alkenyl group optionally substituted by 1 to 3 $C_{6-14}$ aryl groups,
      (III) a $C_{3-10}$ cycloalkyl group optionally substituted by 1 to 3 $C_{1-6}$ alkyl groups,
      (IV) a $C_{6-14}$ aryl group optionally substituted by 1 to 3 substituents selected from
        (A) a halogen atom, and
        (B) a $C_{1-6}$ alkyl group,
      (V) a $C_{7-16}$ aralkyl group,
      (VI) a 5- to 14-membered aromatic heterocyclic group, and
      (VII) a 3- to 14-membered non-aromatic heterocyclic group, and
    (v) a 3- to 14-membered non-aromatic heterocyclylcarbonyl group optionally substituted by 1 to 3 substituents selected from
      (I) a hydroxy group, and
      (II) a $C_{1-6}$ alkyl group, and
  (e) a $C_{7-16}$ aralkyloxy group,
(2) a cyclohexane ring,
(3) a pyridine ring,
(4) an isoxazole ring,
(5) a thiophene ring,
(6) a piperidine ring optionally further substituted by 1 to 3 $C_{1-6}$ alkoxy-carbonyl groups, or
(7) a tetrahydropyran ring.

[3] N-(1,1-Dioxido-2,3-dihydro-1-benzothiophen-5-yl)-2-(4-(5-(l-oxo-5-(piperidin-1-yl)-1,3-dihydro-2H-isoindol-2-yl)-1H-benzimidazol-2-yl)phenoxy)acetamide, or a salt thereof.

[4] 2-(2-(4-Bromophenyl)-1H-benzimidazol-5-yl)-5-(morpholin-4-yl)isoindolin-1-one, or a salt thereof.

[5] 5-(Piperidin-1-yl)-2-(2-(pyridin-3-yl)-1H-benzimidazol-5-yl)isoindolin-1-one, or a salt thereof.

[6] 5-(Piperidin-1-yl)-2-(2-(pyridin-4-yl)-1H-benzimidazol-5-yl)isoindolin-1-one, or a salt thereof.

[7] 2-(2-(4-Hydroxyphenyl)-1H-benzimidazol-5-yl)-5-(piperidin-1-yl) isoindolin-1-one, or a salt thereof.

[8] A cardiomyocyte maturation promoter comprising the compound or salt of the above-mentioned [1].

[9] A method for preparing a mature cardiomyocyte, which comprises a step of culturing an immature cardiomyocyte in the presence of the compound or salt of the above-mentioned [1].

[10] A mature cardiomyocyte obtained by the method of the above-mentioned [9].

Effect of the Invention

Since the above-mentioned compound (I) has an action of maturing cardiomyocytes, it is useful as a cardiomyocyte maturation promoter. The method for promoting cardiomyocyte maturation using the above-mentioned compound matures immature cardiomyocytes in a short period at low cost, as compared with a method for culturing immature cardiomyocytes for a long period.

DETAILED DESCRIPTION OF THE INVENTION

Figure 1:
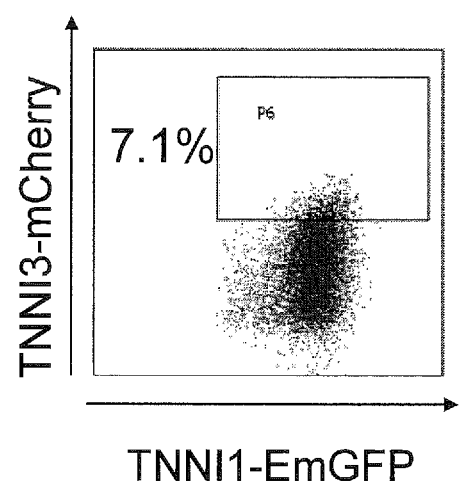
FIG. 1 shows the results of mCherry expression analysis (control (no addition)) by flow cytometry in Experimental Example 2.
Figure 2:
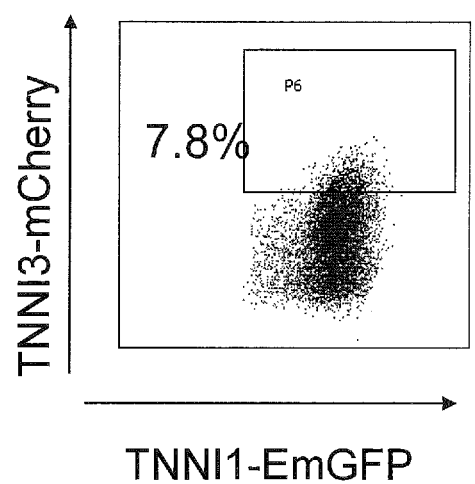
FIG. 2 shows the results of mCherry expression analysis (control (DMSO addition)) by flow cytometry in Experimental Example 2.
Figure 3:
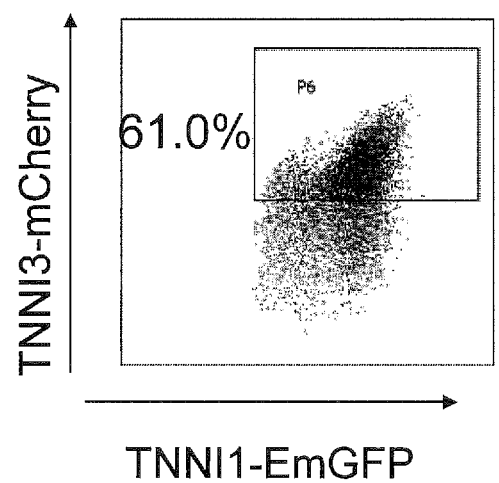
FIG. 3 shows the results of mCherry expression analysis (addition of compound of Example 8) by flow cytometry in Experimental Example 2.
Figure 4:
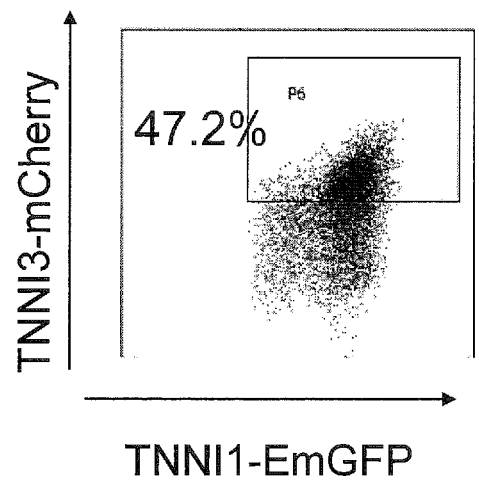
FIG. 4 shows the results of mCherry expression analysis (addition of compound of Example 46) by flow cytometry in Experimental Example 2.
Figure 5:
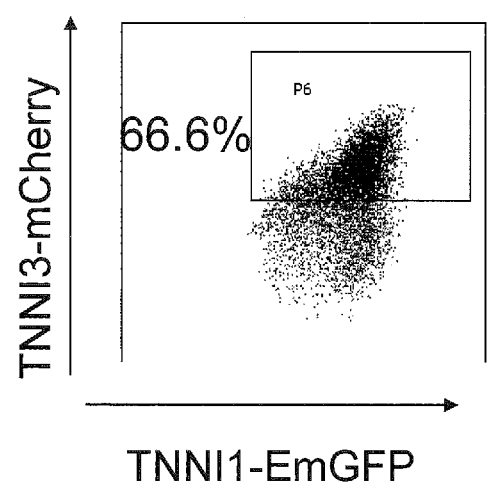
FIG. 5 shows the results of mCherry expression analysis (addition of compound of Example 45) by flow cytometry in Experimental Example 2.
Figure 6:
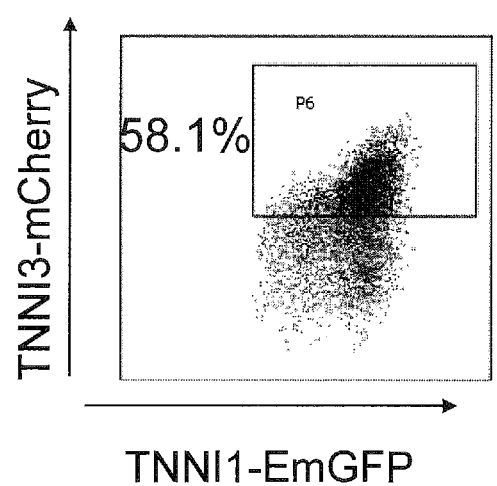
FIG. 6 shows the results of mCherry expression analysis (addition of compound of Example 4) by flow cytometry in Experimental Example 2.
Figure 7:
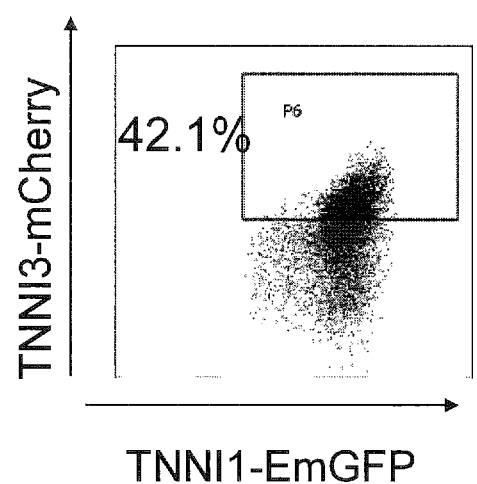
FIG. 7 shows the results of mCherry expression analysis (addition of compound of Example 17) by flow cytometry in Experimental Example 2.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-6}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butyl sulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethyl sulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent (s) selected from the following Substituent Group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamine, isopropylamino, butylamino, dimethylamino, diethylamino, dipropylamino, dibutylamino, N-ethyl-N-methylamino),
(46) a mono- or di-$C_{6-14}$ arylamino group (e.g., phenyl amino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl) amino group (e.g., N-acetyl-N-methylamino),
(52) a $C_{6-14}$ aryl-carbonylamino group (e.g., phenylcarbonylamino, naphthylcarbonylamino),

(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group, and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 heteroatoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 heteroatoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi- or tri-cyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 heteroatoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi- or tri-cyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the above-mentioned Substituent Group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dlmethylphosphono, dlethylphosphono, dlisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent Group A".

Preferable examples of the optionally substituted amino group include an amino group, a mono- or di-(optionally halogenated $C_{1-6}$ alkyl) amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl) amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl) amino group (e.g., N-acetyl-N-methylamino) and a ($C_{1-6}$ alkyl) ($C_{6-14}$ aryl-carbonyl) amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-6}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent Group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-14}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent Group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-6}$ aralkyl group, a $C_{1-6}$ alkyl-carbonyl group, a $C_{6-14}$ aryl-carbonyl group, a $C_{7-6}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent Group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-4}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-4}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxy group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-4}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent Group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ aryl sulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from Substituent Group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-6}$ aralkyl group, each of which optionally has 1 to 3 substituents selected from Substituent Group A".

Preferable examples of the optionally substituted silyl group include a tri-$C_{1-6}$ alkylsilyl group (e.g., trimethylsilyl, tert-butyl(dimethyl)silyl).

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi- or tri-cyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxazine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepane, diazepane, azepine, azocane, diazocane, oxepane and the like; and 9- to 14-membered fused polycyclic (preferably bi- or tri-cyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a heterocycle containing at least one nitrogen atom as a ring-constituting atom, from among the "heterocycle".

In the present specification, examples of the "ring" include a "hydrocarbon ring" and a "heterocycle".

In the present specification, examples of the "5- to 6-membered monocyclic aromatic cyclic amino group" include a 5- to 6-membered monocyclic aromatic heterocyclic group containing at least one nitrogen atom as a ring constituting atom and having a bond on the nitrogen atom, from among the "5- to 6-membered monocyclic aromatic heterocyclic group". Specific examples thereof include 1-pyrrolyl, 1-imidazolyl, 1-pyrazolyl, 1-triazolyl, 1-tetrazolyl and the like.

In the present specification, examples of the "3- to 8-membered monocyclic non-aromatic cyclic amino group" include a 3- to 8-membered monocyclic non-aromatic heterocyclic group containing at least one nitrogen atom as a ring constituting atom and having a bond on the nitrogen atom, from among the "3- to 8-membered monocyclic non-aromatic heterocyclic group". Specific examples thereof include 1-aziridinyl, 1-azetidinyl, 1-pyrrolinyl, 1-imidazolidinyl, 1-pyrazolidinyl, 3-oxazolidinyl, 3-thiazolidinyl, 3-tetrahydroisoxazolyl, 3-tetrahydroisothiazolyl, 1-piperidyl, 1-piperazinyl, 4-morpholinyl, 4-thiomorpholinyl and the like.

The definition of each symbol in the formula (I) is explained in detail in the following.

Ring A and Ring B are each independently an optionally further substituted benzene ring.

The "optionally further substituted benzene ring" represented by Ring A optionally further has substituent(s), in addition to $R^1$ in the formula (I). Examples of the substituent include substituent(s) selected from the above-mentioned Substituent Group A. The number of the substituents is 1 to 3, preferably 1 or 2. When the number of the substituents is 2 or more, the respective substituents may be the same or different.

Ring A is preferably a benzene ring.

The "optionally further substituted benzene ring" represented by Ring B optionally further has substituent(s), in addition to

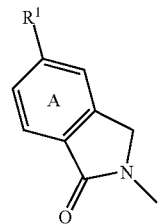

in the formula (I). Examples of the substituent include substituent(s) selected from the above-mentioned Substituent Group A. The number of the substituents is 1 to 3, preferably 1 or 2. When the number of the substituents is 2 or more, the respective substituents may be the same or different.

Ring B is preferably a benzene ring.

Ring C is an imidazole ring optionally further substituted by $C_{1-6}$ alkyl group(s) optionally substituted by 1 to 3 substituents selected from
(1) a halogen atom,
(2) a nitro group,
(3) a cyano group,
(4) an amino group,
(5) a hydroxy group, and
(6) an optionally halogenated $C_{1-6}$ alkoxy group, in addition to -L-Ring D in the formula (I).

Ring C is preferably an imidazole ring optionally further substituted by $C_{1-6}$ alkyl group (s) (e.g., methyl).

Ring C is more preferably an imidazole ring.

The partial structure represented by the formula:

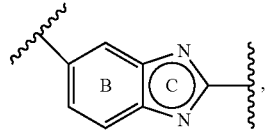

in the formula (I) is a partial structure represented by the formula:

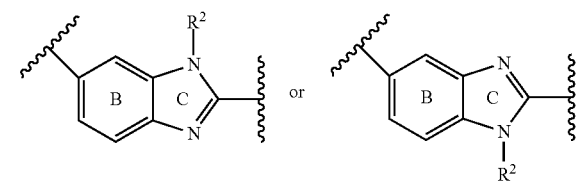

wherein $R^2$ is
(1) a hydrogen atom, or
(2) a $C_{1-6}$ alkyl group optionally substituted by 1 to 3 substituents selected from
  (a) a halogen atom,
  (b) a nitro group, (c) a cyano group,
(d) an amino group,
(e) a hydroxy group, and
(f) an optionally halogenated $C_{1-6}$ alkoxy group.

L is a bond or an optionally substituted methylene group.

Examples of the substituent of the "optionally substituted methylene group" represented by L include substituent (s) selected from the above-mentioned Substituent Group A. The number of the substituents is 1 or 2, preferably 1. When the number of the substituents is 2, the respective substituents may be the same or different.

L is preferably a bond or a methylene group.

L is more preferably a bond.

$R^1$ is a hydrogen atom or a substituent.

$R^1$ is preferably
(1) a hydrogen atom,
(2) a halogen atom (e.g., a bromine atom),
(3) an optionally substituted amino group (preferably a mono- or di-$C_{1-6}$ alkylamino group (e.g., dimethylamino, diethylamino)),
(4) an optionally substituted 5- to 14-membered aromatic heterocyclic group (preferably a 5- to 6-membered monocyclic aromatic heterocyclic group, more preferably a 5- to 6-membered monocyclic aromatic cyclic amino group (e.g., 1-pyrrolyl)), or
(5) an optionally substituted 3- to 14-membered non-aromatic heterocyclic group (preferably a 3- to 8-membered monocyclic non-aromatic heterocyclic group, more preferably a 3- to 8-membered monocyclic non-aromatic cyclic amino group (e.g., 1-piperidyl, 1-piperazinyl, 4-morpholinyl)).

Examples of the substituent of the above-mentioned "optionally substituted 5- to 14-membered aromatic heterocyclic group" and "optionally substituted 3- to 14-membered non-aromatic heterocyclic group" include substituent(s) selected from the above-mentioned Substituent Group A. The number of the substituents is preferably 1 to 3. When the number of the substituents is 2 or more, the respective substituents may be the same or different.

$R^1$ is more preferably
(1) a hydrogen atom,
(2) a halogen atom (e.g., a bromine atom),
(3) a mono- or di-$C_{1-6}$ alkylamino group (e.g., dimethylamino, diethylamino),
(4) a 5- to 14-membered aromatic heterocyclic group (preferably a 5- to 6-membered monocyclic aromatic heterocyclic group, more preferably a 5- to 6-membered monocyclic aromatic cyclic amino group (e.g., 1-pyrrolyl)), or
(5) a 3- to 14-membered non-aromatic heterocyclic group (preferably a 3- to 8-membered (preferably 5- to 6-membered) monocyclic non-aromatic heterocyclic group, more preferably a 3- to 8-membered (preferably 5- to 6-membered) monocyclic non-aromatic cyclic amino group (e.g., 1-piperidyl, 1-piperazinyl, 4-morpholinyl)) optionally substituted by 1 to 3 $C_{1-6}$ alkyl groups (e.g., methyl).

$R^1$ is further more preferably a 3- to 8-membered (preferably 5- to 6-membered) monocyclic non-aromatic heterocyclic group (preferably a 3- to 8-membered (preferably 5- to 6-membered) monocyclic non-aromatic cyclic amino group (e.g., 1-piperidyl, 4-morpholinyl)).

$R^1$ is still more preferably a 3- to 8-membered (preferably 5- to 6-membered) monocyclic non-aromatic cyclic amino group (e.g., 1-piperidyl, 4-morpholinyl).

$R^1$ is particularly preferably a 6-membered monocyclic non-aromatic cyclic amino group (e.g., 1-piperidyl, 4-morpholinyl).

Ring D is an optionally further substituted ring.

The "ring" of the "optionally further substituted ring" represented by Ring D is preferably a $C_{6-14}$ aromatic hydrocarbon ring (e.g., benzene), a $C_{3-10}$ cycloalkane (preferably a $C_{3-8}$ cycloalkane (e.g., cyclohexane)), a 5- to 14-membered aromatic heterocycle (preferably a 5- to 6-membered monocyclic aromatic heterocycle (e.g., pyridine, isoxazole, thiophene)) or a 3- to 14-membered non-aromatic heterocycle (preferably a 3- to 8-membered monocyclic non-aromatic heterocycle (e.g., piperidine, tetrahydropyran)), more preferably a benzene ring, a cyclohexane ring, a pyridine ring, an isoxazole ring, a thiophene ring, a piperidine ring or a tetrahydropyran ring, particularly preferably a benzene ring.

Ring D is preferably
(1) an optionally further substituted $C_{6-14}$ aromatic hydrocarbon ring (e.g., benzene),
(2) an optionally further substituted $C_{3-10}$ cycloalkane (preferably a $C_{3-8}$ cycloalkane (e.g., cyclohexane)),
(3) an optionally further substituted 5- to 14-membered aromatic heterocycle (preferably a 5- to 6-membered monocyclic aromatic heterocycle (e.g., pyridine, isoxazole, thiophene)), or
(4) an optionally further substituted 3- to 14-membered non-aromatic heterocycle (preferably a 3- to 8-membered monocyclic non-aromatic heterocycle (e.g., piperidine, tetrahydropyran)).

The above-mentioned "optionally further substituted $C_{6-14}$ aromatic hydrocarbon ring", "optionally further substituted $C_{3-10}$ cycloalkane", "optionally further substituted 5- to 14-membered aromatic heterocycle" and "optionally further substituted 3- to 14-membered non-aromatic heterocycle" each optionally further has substituent(s), in addition to -L-Ring C/Ring B in the formula (I). Examples of the substituent include the above-mentioned "substituent". The number of the substituents is preferably 1 to 3. When the number of the substituents is 2 or more, the respective substituents may be the same or different.

Ring D is more preferably
(1) a $C_{6-14}$ aromatic hydrocarbon ring (e.g., benzene) optionally further substituted by 1 to 3 substituents selected from
  (a) a halogen atom (e.g., a fluorine atom, a chlorine atom, a bromine atom),
  (b) a hydroxy group,
  (c) a $C_{1-6}$ alkyl group (e.g., methyl) optionally substituted by 1 to 3 $C_{1-6}$ alkoxy groups (e.g., methoxy),
  (d) a $C_{1-6}$ alkoxy group (e.g., methoxy, ethoxy, propoxy, isopropoxy, hexyloxy) optionally substituted by 1 to 3 substituents selected from
    (i) a carboxy group,
    (ii) a $C_{1-6}$ alkoxy-carbonyl group (e.g., methoxycarbonyl),
    (iii) a $C_{7-16}$ aralkyloxy-carbonyl group (e.g., benzyloxycarbonyl),
    (iv) a carbamoyl group optionally mono- or di-substituted by substituent(s) selected from
      (I) a $C_{1-6}$ alkyl group (e.g., methyl, ethyl, propyl, isopropyl, isobutyl) optionally substituted by 1 to 3 substituents selected from
        (A) a $C_{3-10}$ cycloalkyl group (e.g., cyclopropyl),
        (B) a $C_{6-14}$ aryl group (e.g., phenyl),
        (C) a $C_{6-14}$ arylamino group (e.g., phenyl amino) optionally substituted by 1 to 3 halogen atoms (e.g., a fluorine atom),
        (D) a 5- to 14-membered aromatic heterocyclic group (preferably a 5- to 6-membered monocyclic aromatic heterocyclic group (e.g., pyridyl)), (E) a 3- to 14-membered non-aromatic heterocyclic group (preferably a 3- to 8-membered monocyclic non-aromatic heterocyclic group (e.g., tetrahydropyranyl)), and (F) a carbamoyl group optionally mono- or di-substituted by substituent(s) selected from a $C_{1-6}$ alkyl group (e.g., methyl) and a $C_{7-16}$ aralkyl group (e.g., 2-phenylethyl), (II) a $C_{2-6}$ alkenyl group (e.g., pent-2-yl) optionally substituted by 1 to 3 $C_{6-14}$ aryl groups (e.g., phenyl), (III) a $C_{3-10}$ cycloalkyl group (e.g., cyclopropyl) optionally substituted by 1 to 3 $C_{1-6}$ alkyl groups (e.g., methyl), (IV) a $C_{6-14}$ aryl group (e.g., phenyl) optionally substituted by 1 to 3 substituents selected from
(A) a halogen atom (e.g., a fluorine atom, a chlorine atom), and
(B) a $C_{1-6}$ alkyl group (e.g., methyl), (V) a $C_{7-16}$ aralkyl group (e.g., benzyl), (VI) a 5- to 14-membered aromatic heterocyclic group (preferably a 5- to 6-membered monocyclic aromatic heterocyclic group (e.g., pyridyl)), and (VII) a 3- to 14-membered non-aromatic heterocyclic group (preferably a 3- to 8-membered monocyclic non-aromatic heterocyclic group (e.g., tetrahydropyranyl), a 9- to 14-membered fused polycyclic (preferably bi- or tri-cyclic) non-aromatic heterocyclic group (e.g., 1,1-dioxidodihydrobenzothienyl)), and (v) a 3- to 14-membered non-aromatic heterocyclylcarbonyl group (preferably a 3- to 8-membered monocyclic non-aromatic heterocyclylcarbonyl group (e.g., pyrrolidinylcarbonyl, piperidylcarbonyl, morpholinylcarbonyl, 1,1-dioxidothiazolidinylcarbonyl)) optionally substituted by 1 to 3 substituents selected from
(I) a hydroxy group, and
(II) a $C_{1-6}$ alkyl group (e.g., methyl), and (e) a $C_{7-16}$ aralkyloxy group (e.g., benzyloxy), (2) a $C_{3-10}$ cycloalkane (preferably a $C_{3-8}$ cycloalkane (e.g., cyclohexane)), (3) a 5- to 14-membered aromatic heterocycle (preferably a 5- to 6-membered monocyclic aromatic heterocycle (e.g., pyridine, isoxazole, thiophene)), or (4) a 3- to 14-membered non-aromatic heterocycle (preferably a 3- to 8-membered monocyclic non-aromatic heterocycle (e.g., piperidine, tetrahydropyran)) optionally further substituted by 1 to 3 $C_{1-6}$ alkoxy-carbonyl groups (e.g., tert-butoxycarbonyl).

Ring D is further more preferably
(1) a benzene ring optionally further substituted by 1 to 3 substituents selected from
  (a) a halogen atom (e.g., a fluorine atom, a chlorine atom, a bromine atom),
  (b) a hydroxy group,
  (c) a $C_{1-6}$ alkyl group (e.g., methyl) optionally substituted by 1 to 3 $C_{1-6}$ alkoxy groups (e.g., methoxy),
  (d) a $C_{1-6}$ alkoxy group (e.g., methoxy, ethoxy, propoxy, isopropoxy, hexyloxy) optionally substituted by 1 to 3 substituents selected from
    (i) a carboxy group,
    (ii) a $C_{1-6}$ alkoxy-carbonyl group (e.g., methoxycarbonyl),
    (iii) a $C_{7-16}$ aralkyloxy-carbonyl group (e.g., benzyloxycarbonyl),
    (iv) a carbamoyl group optionally mono- or di-substituted by substituent (s) selected from
      (I) a $C_{1-6}$ alkyl group (e.g., methyl, ethyl, propyl, isopropyl, isobutyl) optionally substituted by 1 to 3 substituents selected from
        (A) a $C_{3-10}$ cycloalkyl group (e.g., cyclopropyl),
        (B) a $C_{6-14}$ aryl group (e.g., phenyl),
        (C) a $C_{6-14}$ arylamino group (e.g., phenylamino) optionally substituted by 1 to 3 halogen atoms (e.g., a fluorine atom),
        (D) a 5- to 14-membered aromatic heterocyclic group (preferably a 5- to 6-membered monocyclic aromatic heterocyclic group (e.g., pyridyl)),
        (E) a 3- to 14-membered non-aromatic heterocyclic group (preferably a 3- to 8-membered monocyclic non-aromatic heterocyclic group (e.g., tetrahydropyranyl)), and
        (F) a carbamoyl group optionally mono- or di-substituted by substituent (s) selected from a $C_{1-6}$ alkyl group (e.g., methyl) and a $C_{7-16}$ aralkyl group (e.g., 2-phenylethyl),
      (II) a $C_{2-6}$ alkenyl group (e.g., pent-2-yl) optionally substituted by 1 to 3 $C_{6-14}$ aryl groups (e.g., phenyl),
      (III) a $C_{3-10}$ cycloalkyl group (e.g., cyclopropyl) optionally substituted by 1 to 3 $C_{1-6}$ alkyl groups (e.g., methyl),
      (IV) a $C_{6-14}$ aryl group (e.g., phenyl) optionally substituted by 1 to 3 substituents selected from
        (A) a halogen atom (e.g., a fluorine atom, a chlorine atom), and
        (B) a $C_{1-6}$ alkyl group (e.g., methyl),
      (V) a $C_{7-16}$ aralkyl group (e.g., benzyl),
      (VI) a 5- to 14-membered aromatic heterocyclic group (preferably a 5- to 6-membered monocyclic aromatic heterocyclic group (e.g., pyridyl)), and
      (VII) a 3- to 14-membered non-aromatic heterocyclic group (preferably a 3- to 8-membered monocyclic non-aromatic heterocyclic group (e.g., tetrahydropyranyl), a 9- to 14-membered fused polycyclic (preferably bi- or tri-cyclic) non-aromatic heterocyclic group (e.g., 1,1-dioxidodihydrobenzothienyl)), and
    (v) a 3- to 14-membered non-aromatic heterocyclylcarbonyl group (preferably a 3- to 8-membered monocyclic non-aromatic heterocyclylcarbonyl group (e.g., pyrrolidinylcarbonyl, piperidylcarbonyl, morpholinylcarbonyl, 1,1-dioxidothiazolidinylcarbonyl)) optionally substituted by 1 to 3 substituents selected from
      (I) a hydroxy group, and
      (II) a $C_{1-6}$ alkyl group (e.g., methyl), and
  (e) a $C_{7-16}$ aralkyloxy group (e.g., benzyloxy),
(2) a cyclohexane ring,
(3) a pyridine ring,
(4) an isoxazole ring,
(5) a thiophene ring,
(6) a piperidine ring optionally further substituted by 1 to 3 $C_{1-6}$ alkoxy-carbonyl groups (e.g., tert-butoxycarbonyl), or
(7) a tetrahydropyran ring.

Ring D is still more preferably a benzene ring optionally further substituted by 1 to 3 substituents selected from
  (a) a halogen atom (e.g., a bromine atom), and
  (b) a $C_{1-6}$ alkoxy group (e.g., methoxy) optionally substituted by 1 to 3 substituents selected from
    (i) a carbamoyl group optionally mono- or di-substituted by substituent(s) selected from (I) a $C_{1-6}$ alkyl group (e.g., methyl, isobutyl) optionally substituted by 1 to 3 $C_{3-6}$ cycloalkyl groups (e.g., cyclopropyl), and (II) a 3- to 8-membered monocyclic non-aromatic heterocyclic group (e.g., tetrahydropyranyl), and (ii) a 3- to 8-membered monocyclic non-aromatic heterocyclylcarbonyl group (e.g., piperidylcarbonyl) optionally substituted by 1 to 3 substituents selected from (I) a hydroxy group, and (II) a $C_{1-6}$ alkyl group (e.g., methyl).

As another embodiment, Ring D is still more preferably (1) a benzene ring optionally further substituted by 1 to 3 substituents selected from (a) a halogen atom (e.g., a bromine atom), (b) a hydroxy group, and (c) a $C_{1-6}$ alkoxy group (e.g., methoxy) optionally substituted by carbamoyl group(s) optionally mono- or di-substituted by 9- to 14-membered fused polycyclic (preferably bi- or tri-cyclic) non-aromatic heterocyclic group (s) (e.g., 1,1-dioxidodihydrobenzothienyl), or (2) a pyridine ring.

In the embodiment, Ring D is particularly preferably a benzene ring further substituted by one substituent selected from (a) a halogen atom (e.g., a bromine atom), and (b) a $C_{1-6}$ alkoxy group (e.g., methoxy) substituted by carbamoyl group(s) mono-substituted by a 9- to 14-membered fused polycyclic (preferably bi- or tri-cyclic) non-aromatic heterocyclic group (e.g., 1,1-dioxidodihydrobenzothienyl).

Preferable examples of compound (I) include the following compounds.

[Compound A]

Compound (I) wherein

Ring A is an optionally further substituted benzene ring;
Ring B is an optionally further substituted benzene ring;
Ring C is an imidazole ring optionally further substituted by $C_{1-6}$ alkyl group (s) optionally substituted by 1 to 3 substituents selected from (1) a halogen atom, (2) a nitro group, (3) a cyano group, (4) an amino group, (5) a hydroxy group, and (6) an optionally halogenated $C_{1-6}$ alkoxy group; L is a bond or an optionally substituted methylene group;

$R^1$ is (1) a hydrogen atom, (2) a halogen atom (e.g., a bromine atom), (3) an optionally substituted amino group (preferably a mono- or di-$C_{1-6}$ alkylamino group (e.g., dimethylamino, diethylamino)), (4) an optionally substituted 5- to 14-membered aromatic heterocyclic group (preferably a 5- to 6-membered monocyclic aromatic heterocyclic group, more preferably a 5- to 6-membered monocyclic aromatic cyclic amino group (e.g., 1-pyrrolyl)), or (5) an optionally substituted 3- to 14-membered non-aromatic heterocyclic group (preferably a 3- to 8-membered monocyclic non-aromatic heterocyclic group, more preferably a 3- to 8-membered monocyclic non-aromatic cyclic amino group (e.g., 1-piperidyl, 1-piperazinyl, 4-morpholinyl)); and Ring D is (1) an optionally further substituted $C_{6-14}$ aromatic hydrocarbon ring (e.g., benzene), (2) an optionally further substituted $C_{3-10}$ cycloalkane (preferably a $C_{3-8}$ cycloalkane (e.g., cyclohexane)), (3) an optionally further substituted 5- to 14-membered aromatic heterocycle (preferably a 5- to 6-membered monocyclic aromatic heterocycle (e.g., pyridine, isoxazole, thiophene)), or (4) an optionally further substituted 3- to 14-membered non-aromatic heterocycle (preferably a 3- to 8-membered monocyclic non-aromatic heterocycle (e.g., piperidine, tetrahydropyran)).

[Compound B]

Compound (I) wherein

Ring A is a benzene ring;
Ring B is a benzene ring;
Ring C is an imidazole ring optionally further substituted by $C_{1-6}$ alkyl group (e.g., methyl);
L is a bond or a methylene group;
$R^1$ is (1) a hydrogen atom, (2) a halogen atom (e.g., a bromine atom), (3) a mono- or di-$C_{1-6}$ alkylamino group (e.g., dimethylamino, diethylamino), (4) a 5- to 14-membered aromatic heterocyclic group (preferably a 5- to 6-membered monocyclic aromatic heterocyclic group, more preferably a 5- to 6-membered monocyclic aromatic cyclic amino group (e.g., 1-pyrrolyl)), or (5) a 3- to 14-membered non-aromatic heterocyclic group (preferably a 3- to 8-membered (preferably 5- to 6-membered) monocyclic non-aromatic heterocyclic group, more preferably a 3- to 8-membered (preferably 5- to 6-membered) monocyclic non-aromatic cyclic amino group (e.g., 1-piperidyl, 1-piperazinyl, 4-morpholinyl)) optionally substituted by 1 to 3 $C_{1-6}$ alkyl groups (e.g., methyl); and Ring D is (1) a $C_{6-14}$ aromatic hydrocarbon ring (e.g., benzene) optionally further substituted by 1 to 3 substituents selected from (a) a halogen atom (e.g., a fluorine atom, a chlorine atom, a bromine atom), (b) a hydroxy group, (c) a $C_{1-6}$ alkyl group (e.g., methyl) optionally substituted by 1 to 3 $C_{1-6}$ alkoxy groups (e.g., methoxy), (d) a $C_{1-6}$ alkoxy group (e.g., methoxy, ethoxy, propoxy, isopropoxy, hexyloxy) optionally substituted by 1 to 3 substituents selected from (i) a carboxy group, (ii) a $C_{1-6}$ alkoxy-carbonyl group (e.g., methoxycarbonyl), (iii) a $C_{7-16}$ aralkyloxy-carbonyl group (e.g., benzyloxycarbonyl), (iv) a carbamoyl group optionally mono- or di-substituted by substituent(s) selected from (I) a $C_{1-6}$ alkyl group (e.g., methyl, ethyl, propyl, isopropyl, isobutyl) optionally substituted by 1 to 3 substituents selected from (A) a $C_{3-10}$ cycloalkyl group (e.g., cyclopropyl), (B) a $C_{6-14}$ aryl group (e.g., phenyl), (C) a $C_{6-14}$ arylamino group (e.g., phenylamino) optionally substituted by 1 to 3 halogen atoms (e.g., a fluorine atom), (D) a 5- to 14-membered aromatic heterocyclic group (preferably a 5- to 6-membered monocyclic aromatic heterocyclic group (e.g., pyridyl)), (E) a 3- to 14-membered non-aromatic heterocyclic group (preferably a 3- to 8-membered monocyclic non-aromatic heterocyclic group (e.g., tetrahydropyranyl)), and (F) a carbamoyl group optionally mono- or disubstituted by substituent(s) selected from a $C_{1-6}$ alkyl group (e.g., methyl) and a $C_{7-16}$ aralkyl group (e.g., 2-phenylethyl),
(II) a $C_{2-6}$ alkenyl group (e.g., pent-2-yl) optionally substituted by 1 to 3 $C_{6-14}$ aryl groups (e.g., phenyl),
(III) a $C_{3-10}$ cycloalkyl group (e.g., cyclopropyl) optionally substituted by 1 to 3 $C_{1-6}$ alkyl groups (e.g., methyl),
(IV) a $C_{6-14}$ aryl group (e.g., phenyl) optionally substituted by 1 to 3 substituents selected from
(A) a halogen atom (e.g., a fluorine atom, a chlorine atom), and
(B) a $C_{1-6}$ alkyl group (e.g., methyl),
(V) a $C_{7-16}$ aralkyl group (e.g., benzyl),
(VI) a 5- to 14-membered aromatic heterocyclic group (preferably a 5- to 6-membered monocyclic aromatic heterocyclic group (e.g., pyridyl)), and
(VII) a 3- to 14-membered non-aromatic heterocyclic group (preferably a 3- to 8-membered monocyclic non-aromatic heterocyclic group (e.g., tetrahydropyranyl), a 9- to 14-membered fused polycyclic (preferably bi- or tri-cyclic) non-aromatic heterocyclic group (e.g., 1,1-dioxidodihydrobenzothienyl)), and
(v) a 3- to 14-membered non-aromatic heterocyclylcarbonyl group (preferably a 3- to 8-membered monocyclic non-aromatic heterocyclylcarbonyl group (e.g., pyrrolidinylcarbonyl, piperidylcarbonyl, morpholinylcarbonyl, 1,1-dioxidothiazolidinylcarbonyl)) optionally substituted by 1 to 3 substituents selected from
(I) a hydroxy group, and
(II) a $C_{1-6}$ alkyl group (e.g., methyl), and
(e) a $C_{7-16}$ aralkyloxy group (e.g., benzyloxy),
(2) a $C_{3-10}$ cycloalkane (preferably a $C_{3-8}$ cycloalkane (e.g., cyclohexane)),
(3) a 5- to 14-membered aromatic heterocycle (preferably a 5- to 6-membered monocyclic aromatic heterocycle (e.g., pyridine, isoxazole, thiophene)), or
(4) a 3- to 14-membered non-aromatic heterocycle (preferably a 3- to 8-membered monocyclic non-aromatic heterocycle (e.g., piperidine, tetrahydropyran)) optionally further substituted by 1 to 3 $C_{1-6}$ alkoxy-carbonyl groups (e.g., tert-butoxycarbonyl).
[Compound C]
Compound (I) wherein
Ring A is a benzene ring;
Ring B is a benzene ring;
Ring C is an imidazole ring optionally further substituted by $C_{1-6}$ alkyl group (e.g., methyl);
L is a bond or a methylene group;
$R^1$ is
(1) a hydrogen atom,
(2) a halogen atom (e.g., a bromine atom),
(3) a mono- or di-$C_{1-6}$ alkylamino group (e.g., dimethylamino, diethylamino),
(4) a 5- to 14-membered aromatic heterocyclic group (preferably a 5- to 6-membered monocyclic aromatic heterocyclic group, more preferably a 5- to 6-membered monocyclic aromatic cyclic amino group (e.g., 1-pyrrolyl)), or
(5) a 3- to 14-membered non-aromatic heterocyclic group (preferably a 3- to 8-membered (preferably 5- to 6-membered) non-aromatic heterocyclic group, more preferably a 3- to 8-membered (preferably 5- to 6-membered) monocyclic non-aromatic cyclic amino group (e.g., 1-piperidyl, 1-piperazinyl, 4-morpholinyl)) optionally substituted by 1 to 3 $C_{1-6}$ alkyl groups (e.g., methyl); and
Ring D is
(1) a benzene ring optionally further substituted by 1 to 3 substituents selected from
(a) a halogen atom (e.g., a fluorine atom, a chlorine atom, a bromine atom),
(b) a hydroxy group,
(c) a $C_{1-6}$ alkyl group (e.g., methyl) optionally substituted by 1 to 3 $C_{1-6}$ alkoxy groups (e.g., methoxy),
(d) a $C_{1-6}$ alkoxy group (e.g., methoxy, ethoxy, propoxy, isopropoxy, hexyloxy) optionally substituted by 1 to 3 substituents selected from
(i) a carboxy group,
(ii) a $C_{1-6}$ alkoxy-carbonyl group (e.g., methoxycarbonyl),
(iii) a $C_{7-16}$ aralkyloxy-carbonyl group (e.g., benzyloxycarbonyl),
(iv) a carbamoyl group optionally mono- or di-substituted by substituent(s) selected from
(I) a $C_{1-6}$ alkyl group (e.g., methyl, ethyl, propyl, isopropyl, isobutyl) optionally substituted by 1 to 3 substituents selected from
(A) a $C_{3-10}$ cycloalkyl group (e.g., cyclopropyl),
(B) a $C_{6-14}$ aryl group (e.g., phenyl),
(C) a $C_{6-14}$ arylamino group (e.g., phenylamino) optionally substituted by 1 to 3 halogen atoms (e.g., a fluorine atom),
(D) a 5- to 14-membered aromatic heterocyclic group (preferably a 5- to 6-membered monocyclic aromatic heterocyclic group (e.g., pyridyl)),
(E) a 3- to 14-membered non-aromatic heterocyclic group (preferably a 3- to 8-membered monocyclic non-aromatic heterocyclic group (e.g., tetrahydropyranyl)), and
(F) a carbamoyl group optionally mono- or di-substituted by substituent(s) selected from a $C_{1-6}$ alkyl group (e.g., methyl) and a $C_{7-16}$ aralkyl group (e.g., 2-phenylethyl),
(II) a $C_{2-6}$ alkenyl group (e.g., pent-2-yl) optionally substituted by 1 to 3 $C_{6-14}$ aryl groups (e.g., phenyl),
(III) a $C_{3-10}$ cycloalkyl group (e.g., cyclopropyl) optionally substituted by 1 to 3 $C_{1-6}$ alkyl groups (e.g., methyl),
(IV) a $C_{6-14}$ aryl group (e.g., phenyl) optionally substituted by 1 to 3 substituents selected from
(A) a halogen atom (e.g., a fluorine atom, a chlorine atom), and
(B) a $C_{1-6}$ alkyl group (e.g., methyl),
(V) a $C_{7-16}$ aralkyl group (e.g., benzyl),
(VI) a 5- to 14-membered aromatic heterocyclic group (preferably a 5- to 6-membered monocyclic aromatic heterocyclic group (e.g., pyridyl)), and
(VII) a 3- to 14-membered non-aromatic heterocyclic group (preferably a 3- to 8-membered monocyclic non-aromatic heterocyclic group (e.g., tetrahydropyranyl), a 9- to 14-membered fused polycyclic (preferably bi- or tri-cyclic) non-aromatic heterocyclic group (e.g., 1,1-dioxidodihydrobenzothienyl)), and
(v) a 3- to 14-membered non-aromatic heterocyclylcarbonyl group (preferably a 3- to 8-membered monocyclic non-aromatic heterocyclylcarbonyl group (e.g., pyrrolidinylcarbonyl, piperidylcarbonyl, morpholinylcarbonyl, 1,1-dioxidothiazolidinylcarbonyl)) optionally substituted by 1 to 3 substituents selected from
(I) a hydroxy group, and
(II) a $C_{1-6}$ alkyl group (e.g., methyl), and
(e) a $C_{7-16}$ aralkyloxy group (e.g., benzyloxy),
(2) a cyclohexane ring,
(3) a pyridine ring,
(4) an isoxazole ring,
(5) a thiophene ring,
(6) a piperidine ring optionally further substituted by 1 to 3 $C_{1-6}$ alkoxy-carbonyl groups (e.g., tert-butoxycarbonyl), or
(7) a tetrahydropyran ring.

[Compound D]
Compound (I) wherein
Ring A is a benzene ring;
Ring B is a benzene ring;
Ring C is an imidazole ring;
L is a bond;
$R^1$ is a 3- to 8-membered (preferably 5- to 6-membered) monocyclic non-aromatic heterocyclic group (preferably a 3- to 8-membered (preferably 5- to 6-membered) monocyclic non-aromatic cyclic amino group (e.g., 1-piperidyl, 4-morpholinyl)); and
Ring D is a benzene ring optionally further substituted by 1 to 3 substituents selected from
(a) a halogen atom (e.g., a bromine atom), and
(b) a $C_{1-6}$ alkoxy group (e.g., methoxy) optionally substituted by 1 to 3 substituents selected from
(i) a carbamoyl group optionally mono- or di-substituted by substituent(s) selected from
(I) a $C_{1-6}$ alkyl group (e.g., methyl, isobutyl) optionally substituted by 1 to 3 $C_{3-6}$ cycloalkyl groups (e.g., cyclopropyl), and
(II) a 3- to 8-membered monocyclic non-aromatic heterocyclic group (e.g., tetrahydropyranyl), and
(ii) a 3- to 8-membered monocyclic non-aromatic heterocyclylcarbonyl group (e.g., piperidylcarbonyl) optionally substituted by 1 to 3 substituents selected from
(I) a hydroxy group, and
(II) a $C_{1-6}$ alkyl group (e.g., methyl).

[Compound E]
Compound (I) wherein
Ring A is a benzene ring;
Ring B is a benzene ring;
Ring C is an imidazole ring;
L is a bond;
$R^1$ is a 3- to 8-membered (preferably 5- to 6-membered) monocyclic non-aromatic heterocyclic group (preferably a 3- to 8-membered (preferably 5- to 6-membered) monocyclic non-aromatic cyclic amino group (e.g., 1-piperidyl, 4-morpholinyl)); and
Ring D is
(1) a benzene ring optionally further substituted by 1 to 3 substituents selected from
(a) a halogen atom (e.g., a bromine atom),
(b) a hydroxy group, and
(c) a $C_{1-6}$ alkoxy group (e.g., methoxy) optionally substituted by carbamoyl group(s) optionally mono- or di-substituted by 9- to 14-membered fused polycyclic (preferably bi- or tri-cyclic) non-aromatic heterocyclic group(s) (e.g., 1,1-dioxidodihydrobenzothienyl), or
(2) a pyridine ring.

[Compound F]
Compound (I) wherein
Ring A is a benzene ring;
Ring B is a benzene ring;
Ring C is an imidazole ring;
L is a bond;
$R^1$ is a 3- to 8-membered (preferably 5- to 6-membered) monocyclic non-aromatic cyclic amino group (e.g., 1-piperidyl, 4-morpholinyl); and
Ring D is a benzene ring further substituted by one substituent selected from
(a) a halogen atom (e.g., a bromine atom), and
(b) a $C_{1-6}$ alkoxy group (e.g., methoxy) substituted by carbamoyl group(s) mono-substituted by a 9- to 14-membered fused polycyclic (preferably bi- or tricyclic) non-aromatic heterocyclic group (e.g., 1,1-dioxidodihydrobenzothienyl).

[Compound G]
N-(1,1-dioxido-2,3-dihydro-1-benzothiophen-5-yl)-2-(4-(5-(1-oxo-5-(piperidin-1-yl)-1,3-dihydro-2H-isoindol-2-yl)-1H-benzimidazol-2-yl)phenoxy)acetamide, or a salt thereof (Example 17).
2-(2-(4-bromophenyl)-1H-benzimidazol-5-yl)-5-(morpholin-4-yl)isoindolin-1-one, or a salt thereof (Example 8).
5-(piperidin-1-yl)-2-(2-(pyridin-3-yl)-1H-benzimidazol-5-yl)isoindolin-1-one, or a salt thereof (Example 46).
5-(piperidin-1-yl)-2-(2-(pyridin-4-yl)-1H-benzimidazol-5-yl)isoindolin-1-one, or a salt thereof (Example 45).
2-(2-(4-hydroxyphenyl)-1H-benzimidazol-5-yl)-5-(piperidin-1-yl)isoindolin-1-one, or a salt thereof (Example 4).

Specific examples of compound (I) include the compounds of the below-mentioned Examples 1 to 73.

As a salt of a compound represented by the formula (I), a pharmacologically acceptable salt is preferable, and examples of such salt include a salt with inorganic base, a salt with organic base, a salt with inorganic acid, a salt with organic acid, a salt with basic or acidic amino acid and the like.

Preferable examples of the salt with inorganic base include alkali metal salts such as sodium salt, potassium salt and the like, alkaline earth metal salts such as calcium salt, magnesium salt and the like, aluminum salt, ammonium salt and the like.

Preferable examples of the salt with organic base include salts with trimethylamine, triethylamine, pyridine, picoline, ethanolamine, diethanolamine, triethanolamine, tromethamine[tris(hydroxymethyl)methylamine], tert-butylamine, cyclohexylamine, benzylamine, dicyclohexylamine, N,N-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

The production method of compound (I) is explained below.

The raw material compound and reagent used and the compound obtained in each step in the following production method may be each in a form of a salt, and examples of such salt include those similar to the salts of the compound represented by the formula (I), and the like.

When the compound obtained in each step is a free form, it can be converted to the objective salt according to a method known per se. When the compound obtained in each step is a salt, it can be converted to the objective free form or the other salt according to a method known per se.

The compound obtained in each step can be used directly as the reaction mixture or as a crude product for the next reaction. Alternatively, the compound obtained in each step can be isolated and purified from a reaction mixture according to a method known per se, for example, a separation means such as concentration, crystallization, recrystallization, distillation, solvent extraction, fractional distillation, column chromatography and the like.

When the raw material compound and reagent used in each step are commercially available, the commercially available product can also be used directly.

In the reaction in each step, while the reaction time varies depending on the kind of the reagent and solvent to be used, it is generally 1 min-48 hr, preferably 10 min-8 hr, unless otherwise specified.

In the reaction in each step, while the reaction temperature varies depending on the kind of the reagent and solvent to be used, it is generally −78° C.-300° C., preferably −78° C.-150° C., unless otherwise specified.

In the reaction in each step, while the pressure varies depending on the kind of the reagent and solvent to be used, it is generally 1 atm-20 atm, preferably 1 atm-3 atm, unless otherwise specified.

Microwave synthesizer such as Initiator manufactured by Biotage and the like may be used for the reaction in each step.

While the reaction temperature varies depending on the kind of the reagent and solvent to be used, it is generally room temperature—300° C., preferably 50° C.-250° C., unless otherwise specified. While the reaction time varies depending on the kind of the reagent and solvent to be used, it is generally 1 min-48 hr, preferably 1 min-8 hr, unless otherwise specified.

In the reaction in each step, the reagent is used in an amount of 0.5 equivalents-20 equivalents, preferably 0.8 equivalents-5 equivalents, relative to the substrate, unless otherwise specified. When the reagent is used as a catalyst, the reagent is used in an amount of 0.001 equivalent-1 equivalent, preferably 0.01 equivalent-0.2 equivalent, relative to the substrate. When the reagent is used as a reaction solvent, the reagent is used in a solvent amount.

Unless otherwise specified, the reaction in each step is carried out without solvent, or by dissolving or suspending the raw material compound in a suitable solvent. Examples of the solvent include those described in Examples and the following solvents.
alcohols: methanol, ethanol, tert-butyl alcohol, 2-methoxyethanol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like;
amides: N,N-dimethylformamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
anhydrides: acetic anhydride and the like;
organic acids: formic acid, acetic acid, trifluoroacetic acid and the like;
inorganic acids: hydrochloric acid, sulfuric acid and the like;
esters: ethyl acetate and the like;
ketones: acetone, methyl ethyl ketone and the like; water.

The above-mentioned solvent can be used in a mixture of two or more kinds thereof in an appropriate ratio.

When a base is used for the reaction in each step, examples thereof include those described in Examples and the following bases.
inorganic bases: sodium hydroxide, magnesium hydroxide, sodium carbonate, calcium carbonate, sodium hydrogen carbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
metal alkoxides: sodium ethoxide, potassium tert-butoxide and the like;
alkali metal hydrides: sodium hydride and the like;
metal amides: sodium amide, lithium diisopropylamide, lithium hexamethyldisilazide and the like;
organic lithiums: n-butyllithium and the like.

When an acid or an acid catalyst is used for the reaction in each step, examples thereof include those described in Examples and the following acids and acid catalysts.
inorganic acids: hydrochloric acid, sulfuric acid, nitric acid, hydrobromic acid, phosphoric acid and the like;
organic acids: acetic acid, trifluoroacetic acid, citric acid, p-toluenesulfonic acid, 10-camphorsulfonic acid and the like;
Lewis acid: boron trifluoride diethyl ether complex, zinc iodide, anhydrous aluminum chloride, anhydrous zinc chloride, anhydrous iron chloride and the like.

Unless otherwise specified, the reaction in each step is carried out according to a method known per se, for example, the method described in Jikken Kagaku Kouza, 5th Edition, vol. 13-19 (the Chemical Society of Japan ed.); Shin Jikken Kagaku Kouza, vol. 14-15 (the Chemical Society of Japan ed.); Fine Organic Chemistry, Revised 2nd Edition (L. F. Tietze, Th. Eicher, Nankodo); Organic Name Reactions, the Reaction Mechanism and Essence, Revised Edition (Hideo Togo, Kodansha); ORGANIC SYNTHESES Collective Volume I-VII (John Wiley & Sons Inc.); Modern Organic Synthesis in the Laboratory A Collection of Standard Experimental Procedures (Jie Jack Li, OXFORD UNIVERSITY); Comprehensive Heterocyclic Chemistry III, Vol. 1-Vol. 14 (Elsevier Japan); Strategic Applications of Named Reactions in Organic Synthesis (translated by Kiyoshi Tomioka, Kagakudojin); Comprehensive Organic Transformations (VCH Publishers Inc.), 1989, or the like, or the method described in Examples.

In each step, the protection or deprotection reaction of an functional group is carried out according to a method known per se, for example, the method described in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski), or the like, or the method described in Examples.

Examples of the protecting group for a hydroxy group of an alcohol and the like and a phenolic hydroxy group include ether-type protecting groups such as methoxymethyl ether, benzyl ether, tert-butyldimethylsilyl ether, tetrahydropyranyl ether and the like; carboxylate ester-type protecting groups such as acetate ester and the like; sulfonate ester-type protecting groups such as methanesulfonate ester and the like; carbonate ester-type protecting groups such as tert-butylcarbonate and the like, and the like.

Examples of the protecting group for a carbonyl group of an aldehyde include acetal-type protecting groups such as dimethylacetal and the like; cyclic acetal-type protecting groups such as 1,3-dioxane and the like, and the like.

Examples of the protecting group for a carbonyl group of a ketone include ketal-type protecting groups such as dimethylketal and the like; cyclic ketal-type protecting groups such as 1,3-dioxane and the like; oxime-type protecting groups such as O-methyloxime and the like; hydrazone-type protecting groups such as N,N-dimethylhydrazone and the like, and the like.

Examples of the protecting group for a carboxyl group include ester-type protecting groups such as methyl ester and the like; amide-type protecting groups such as N,N-dimethylamide and the like, and the like.

Examples of the protecting group for a thiol include ether-type protecting groups such as benzyl thioether and the like; ester-type protecting groups such as thioacetate ester, thiocarbonate, thiocarbamate and the like, and the like.

Examples of the protecting group for an amino group and an aromatic heterocycle such as imidazole, pyrrole, indole and the like include carbamate-type protecting groups such as benzyl carbamate and the like; amide-type protecting groups such as acetamide and the like; alkyl amine-type protecting groups such as N-triphenylmethylamine and the like; sulfonamide-type protecting groups such as methanesulfonamide and the like, and the like.

The protecting groups can be removed according to a method known per se, for example, by employing a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method, and the like.

When reduction reaction is carried out in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney nickel; Raney cobalt; hydrogen; formic acid; triethylsilane and the like. When carbon-carbon double bond or triple bond is reduced, a method using a catalyst such as palladium-carbon, Lindlar's catalyst and the like may be employed.

When oxidation reaction is carried out in each step, examples of the oxidizing agent to be used include peroxides such as m-chloroperbenzoic acid (mCPBA), hydrogen peroxide, tert-butylhydroperoxide and the like; perchlorates such as tetrabutylammonium perchlorate and the like; chlorates such as sodium chlorate and the like; chlorites such as sodium chlorite and the like; periodates such as sodium periodate and the like; hypervalent iodine reagents such as iodosylbenzene and the like; reagents containing manganese such as manganese dioxide, potassium permanganate and the like; leads such as lead tetraacetate and the like; reagents containing chromium such as pyridinium chlorochromate (PCC), pyridinium dichromate (PDC), Jones reagent and the like; halogen compounds such as N-bromosuccinimide (NBS) and the like; oxygen; ozone; sulfur trioxide-pyridine complex; osmium tetroxide; selenium dioxide; 2,3-dichloro-5,6-dicyano-1,4-benzoquinone (DDQ) and the like.

When radical cyclization reaction is carried out in each step, examples of the radical initiator to be used include azo compounds such as azobisisobutyronitrile (AIBN) and the like; water-soluble radical initiators such as 4-4'-azobis-4-cyanopentanoic acid (ACPA) and the like; triethylboron in the presence of air or oxygen; benzoyl peroxide and the like.

Examples of the radical reagent to be used include tributylstannane, tristrimethylsilylsilane, 1,1,2,2-tetraphenyldisilane, diphenylsilane, samarium iodide and the like.

When Wittig reaction is carried out in each step, examples of the Wittig reagent to be used include alkylidene phosphoranes and the like. The alkylidene phosphoranes can be prepared according to a method known per se, for example, by reacting a phosphonium salt with a strong base.

When Horner-Emmons reaction is carried out in each step, examples of the reagent to be used include phosphonoacetates such as methyl dimethylphosphonoacetate, ethyl diethylphosphonoacetate and the like; and bases such as alkali metal hydrides, organic lithiums and the like.

When Friedel-Crafts reaction is carried out in each step, a combination of a Lewis acid and an acid chloride or a combination of a Lewis acid and an alkylating agent (e.g., an alkyl halide, an alcohol, an olefin etc.) is used as a reagent. Alternatively, an organic acid or an inorganic acid can also be used instead of a Lewis acid, and an anhydride such as acetic anhydride and the like can also be used instead of an acid chloride.

When aromatic nucleophilic substitution reaction is carried out in each step, a nucleophile (e.g., an amine, imidazole etc.) and a base (e.g., an organic base etc.) are used as a reagent.

When nucleophilic addition reaction by a carbo anion, nucleophilic 1,4-addition reaction (Michael addition reaction) by a carbo anion or nucleophilic substitution reaction by a carbo anion is carried out in each step, and examples of the base to be used for generation of the carbo anion include organic lithiums, metal alkoxides, inorganic bases, organic bases and the like.

When Grignard reaction is carried out in each step, examples of the Grignard reagent to be used include arylmagnesium halides such as phenylmagnesium bromide and the like; and alkylmagnesium halides such as methy Magnesium bromide and the like. The Grignard reagent can be prepared according to a method known per se, for example, by reacting an alkyl halide or an aryl halide with a metal magnesium in an ether or tetrahydrofuran as a solvent.

When Knoevenagel condensation reaction is carried out in each step, a compound having an activated methylene group with two electron withdrawing groups (e.g., malonic acid, diethyl malonate, malononitrile etc.) and a base (e.g., an organic base, a metal alkoxide, an inorganic base) are used as a reagent.

When Vilsmeier-Haack reaction is carried out in each step, phosphoryl chloride and an amide derivative (e.g., N,N-dimethylformamide etc.) are used as a reagent.

When azidation reaction of an alcohol, an alkyl halide or a sulfonate is carried out in each step, examples of the azidating agent to be used include diphenylphosphorylazide (DPPA), trimethylsilylazide, sodium azide and the like. For example, for the azidation reaction of an alcohol, a method using diphenylphosphorylazide and 1,8-diazabicyclo [5.4.0] undec-7-ene (DBCJ), a method using trimethylsilylazide and a Lewis acid, and the like are employed.

When reductive amination reaction is carried out in each step, examples of the reducing agent to be used include sodium triacetoxyborohydride, sodium cyanoborohydride, hydrogen, formic acid and the like. When the substrate is an amine compound, examples of the carbonyl compound to be used include paraformaldehyde, aldehydes such as acetaldehyde and the like, and ketones such as cyclohexanone and the like. When the substrate is a carbonyl compound, examples of the amine to be used include ammonia, primary amines such as methylamine and the like; secondary amines such as dimethylamine and the like, and the like.

When Mitsunobu reaction is carried out in each step, an azodicarboxylate (e.g., diethyl azodicarboxylate (DEAD), diisopropyl azodicarboxylate (DIAD) etc.) and a phosphine (e.g., triphenylphosphine, tributhlphosphine) are used as a reagent.

When esterification reaction, amidation reaction or urea formation reaction is carried out in each step, examples of the reagent to be used include acyl halides such as acid chlorides, acid bromides and the like; activated carboxylic acids such as acid anhydrides, activated esters, sulfates and the like. Examples of the activating agent of the carboxylic acid include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride n-hydrate (DMT-MM) and the like; carbonate condensing agents such as 1,1-carbonyldiimidazole (GDI) and the like; diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphate (HATU); sulfuric acid; combinations thereof and the like. When carbodiimide condensing agent is used, an additive such as 1-hydroxybenzotriazole (HOBt), N-hydroxysuccinimide (HOSu), dimethylaminopyridine (DMAP) and the like may be added to the reaction system.

When coupling reaction is carried out in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride and the like; nickel compounds such as tetrakis (triphenylphosphine)nickel(0) and the like; rhodium compounds such as tris(triphenylphosphine)rhodium(III) chloride and the like; cobalt compounds; copper compounds such as copper oxide, copper(I) iodide and the like; platinum compounds and the like. In addition, a base can be added to the reaction system, and examples thereof include inorganic bases and the like.

When thiocarbonylation reaction is carried out in each step, phosphorus pentasulfide is typically used as the thiocarbonylating agent. Alternatively, a reagent having a 1,3,2,4-dithiadiphosphetane-2,4-disulfide structure (e.g., 2,4-bis(4-methoxyphenyl)-1,3,2,4-dithiadiphosphetane-2,4-disulfide (Lawesson reagent) etc.) can also be used instead of phosphorus pentasulfide.

When Wohl-Ziegler reaction is carried out in each step, examples of the halogenating agent to be used include N-iodosuccinimide, N-bromosuccinimide (NBS), N-chlorosuccinimide (NCS), bromine, sulfuryl chloride and the like. In addition, the reaction can be accelerated by subjecting a radical initiator such as heat, light, benzoyl peroxide, azobisisobutyronitrile and the like to the reaction system reaction.

When halogenation reaction of a hydroxy group is carried out in each step, examples of the halogenating agent to be used include hydrohalic acids and acid halides of inorganic acids, specifically, hydrochloric acid, thionyl chloride, phosphorus oxychloride and the like for chlorination, 48% hydrobromic acid and the like for bromination. In addition, a method of producing an alkyl halide by reacting an alcohol with triphenylphosphine and carbon tetrachloride or carbon tetrabromide or the like can be employed. Alternatively, a method of producing an alkyl halide via two step comprising converting an alcohol to the corresponding sulfonate, and then reacting the sulfonate with lithium bromide, lithium chloride or sodium iodide can also be employed.

When Arbuzov reaction is carried out in each step, examples of the reagent to be used include alkyl halides such as ethyl bromoacetate and the like; and phosphites such as triethyl phosphite, tri(isopropyl) phosphite and the like.

When sulfonate esterification reaction is carried out in each step, examples of the sulfonating agent to be used include methanesulfonyl chloride, p-toluenesulfonyl chloride, methanesulfonic anhydride, p-toluenesulfonic anhydride and the like.

When hydrolysis reaction is carried out in each step, an acid or a base is used as a reagent. For acid hydrolysis reaction of tert-butyl ester, formic acid, triethylsilane and the like may be added to reductively-trap tert-butyl cation which is by-produced.

When dehydration reaction is carried out in each step, examples of the dehydrating agent to be used include sulfuric acid, diphosphorus pentaoxide, phosphorus oxychloride, N, N'-dicyclohexylcarbodiimide, alumina, polyphosphoric acid and the like.

Compound (I) can be produced from compound (II) according to the following method.

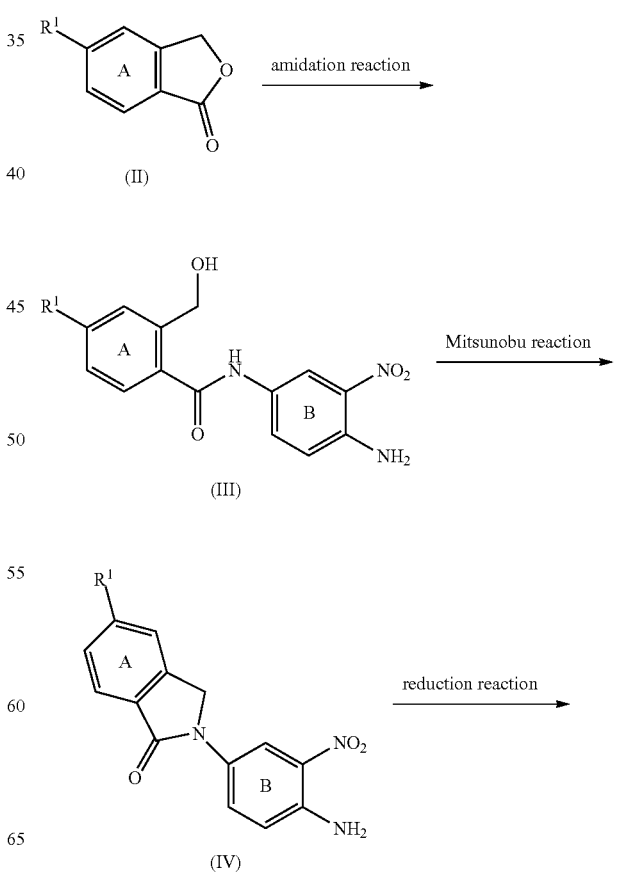

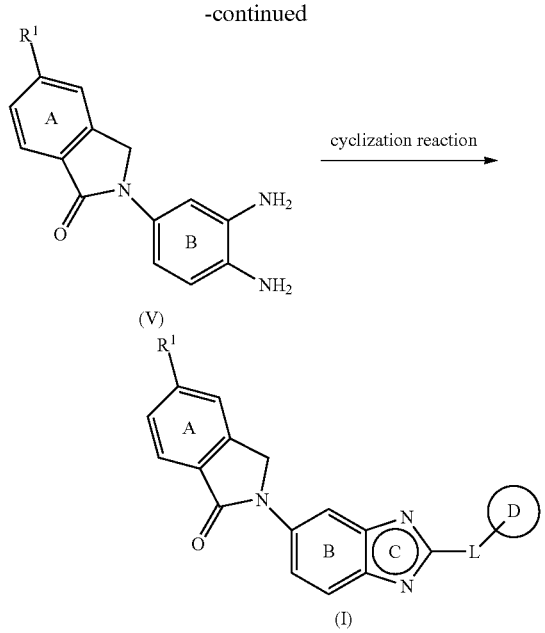

wherein each symbol is as defined above.

Compound (II) can be produced according to a method known per se or a method analogous thereto.

Compound (III) can be produced by subjecting compound (II) to an amidation reaction.

Compound (IV) can be produced by subjecting compound (III) to a Mitsunobu reaction.

Compound (V) can be produced by subjecting compound (IV) to a reduction reaction.

Compound (I) can be produced by subjecting compound (V) to a cyclization reaction. Examples of the reactant include an aldehyde, an acid chloride and the like, which correspond to -L-Ring D. Sodium hydrogensulfite, triethylamine and the like may be added to the reaction system.

In the thus-obtained compound (I), an intramolecular functional group can also be converted to an object functional group by a combination of chemical reactions known per se. Examples of the chemical reaction include oxidation reaction, reduction reaction, alkylation reaction, acylation reaction, ureation reaction, hydrolysis reaction, amination reaction, esterification reaction, aryl coupling reaction, deprotection reaction and the like.

In the above-mentioned production method, when a starting compound has an amino group, a carboxyl group, a hydroxy group, a carbonyl group or a mercapto group as a substituent, a protecting group generally used in the peptide chemistry may be introduced into these groups, and the object compound can be obtained by removing the protecting group as necessary after the reaction.

Compound (I) obtained by the above-mentioned production method can be isolated and purified by a known means, such as solvent extraction, liquid conversion, phase transfer, crystallization, recrystallization, chromatography and the like.

When compound (I) contains optical isomer, stereoisomer, regio isomer and rotamer, these compounds are also included in compound (I), and each can be obtained as a single product by a synthesis method or a separation method known per se. For example, when an optical isomer exists in compound (I), an optical isomer resolved from the compound is also encompassed in compound (I).

Here, an optical isomer can be produced by a method known per se.

Compound (I) may be a crystal.

A crystal of compound (I) (hereinafter sometimes to be abbreviated as the crystal of the present invention) can be produced by crystallizing compound (I), by applying a crystallization method known per se.

In the present specification, the melting point means a melting point measured, for example, by micro melting point apparatus (Yanako, MP-500D or Buchi, B-545), DSC (differential scanning calorimetry analysis) apparatus (SEIKO, EXSTAR6000) and the like.

Generally, the melting point sometimes varies depending on the measurement device, measurement condition and the like. The crystal in the present specification may be a crystal showing a melting point different from the values described in the present specification as long as the difference is within a general error range.

The above-mentioned compound may be a hydrate, a non-hydrate, a solvate or a non-solvate.

Moreover, the above-mentioned compound may be labeled with or substituted by isotope (e.g., $^2$H, $^3$H, $^{11}$C, $^{14}$C, $^{18}$F, $^{35}$S, $^{125}$I and the like) and the like.

The above-mentioned compound also encompasses a deuterium conversion form wherein $^1$H is converted to $^2$H(D).

The above-mentioned compound also encompasses the tautomers.

The above-mentioned compound may be a pharmaceutically acceptable cocrystal or cocrystal salt. The cocrystal or cocrystal salt means a crystalline substance constituted with two or more special solids at room temperature, each having different physical properties (e.g., structure, melting point, melting heat, hygroscopicity, solubility, stability etc.). The cocrystal or cocrystal salt can be produced by a cocrystallization method known per se.

The cardiomyocyte maturation promoter of the present invention can be used as it is or by mixing with a pharmacologically acceptable carrier, and formulating the mixture according to a method known per se.

Since compound (I) has an excellent activity to promote the maturation of a cardiomyocyte, it is useful as a cardiomyocyte maturation promoter. Therefore, by culturing immature cardiomyocytes in the presence of compound (I) or a salt thereof, mature cardiomyocytes can be prepared in a shorter period than when culturing in only medium components.

As used herein, the term "pluripotency" means ability to differentiate into various tissues or cells having different morphologies and/or functions, and to differentiate into any series of cells of three germ layers. The "pluripotency" cannot differentiate into blastodisc. Therefore, the "pluripotency" is distinguished from the term "totipotency" which can differentiate into every tissue of the living body including blastodisc, in that it has no ability to form an individual.

As used herein, the term "multipotency" means ability to differentiate into plural limited numbers of series of cells. For example, mesenchymal stem cells, hematopoietic stem cells and neural stem cells are multipotent, but not pluripotent.

As used herein, examples of the "stem cells" include pluripotent stem cells.

The "cardiomyocytes" to which compound (I) is applied is not particularly limited, and they are preferably derived from a mammal (e.g., mouse, rat, hamster, rabbit, cat, dog, cow, sheep, pig, monkey, human), more preferably derived from human.

The cardiomyocytes whose maturation can be promoted by compound (I) are not particularly limited as long as it can be determined that they are in an immature stage based on the below-mentioned marker expression levels, morphologies and structures (e.g., sarcomere, mitochondria), properties (e.g., pulsatility, electrophysiological maturity) and the like.

The cardiomyocytes whose maturation can be promoted by compound (I) may also be cells prepared by differentiation induction from pluripotent stem cells, or immature cardiomyocytes isolated from a living body (e.g., cardiomyocytes derived from a mouse or rat fetus or newborn).

Examples of the pluripotent stem cells include, but are not limited to, embryonic stem (ES) cells, germline stem cells ("GS cells"), embryonic germ cells ("EG cells"), induced pluripotent stem (iPS) cells, embryonic stem cells derived from a cloned embryo obtained by nuclear transfer (ntES cells), and the like. The pluripotent stem cells are preferably ES cells, iPS cells or ntES cells.

(A) Embryonic Stem Cells

ES cells are stem cells established from the inner cell mass of an early embryo (for example, blastocyst) of a mammal such as human, mouse and the like, which cells have pluripotency and growth ability by self-renewal.

ES cells are embryo-derived stem cells originated from the inner cell mass of a blastocyst, which is the embryo formed following the 8-cell stage and the morula stage of a fertilized egg. ES cells have ability to differentiate into any cells constituting an adult, that is, the so-called pluripotency of differentiation, and growth ability by self-renewal. ES cells were discovered in mouse in 1981 (M. J. Evans and M. H. Kaufman. (1981), Nature 292: 154-156), and this was followed by establishment of ES cell lines of primates such as human, monkey and the like (J. A. Thomson et al. (1998), Science 282: 1145-1147; J. A. Thomson et al. (1995), Proc. Natl. Acad. Sci. USA, 92: 7844-7848; J. A. Thomson et al. (1996), Biol. Reprod., 55: 254-259; J. A. Thomson and V. S. Marshall (1998), Curr. Top. Dev. Biol., 38: 133-165).

ES cells can be established by removing the inner cell mass from the blastocyst of a fertilized egg of a subject animal, followed by culturing the inner cell mass on feeder fibroblasts. The cells can be maintained by subculture using a culture medium supplemented with a substance (s) such as leukemia inhibitory factor (LIE), basic fibroblast growth factor (bFGF), and the like. Methods of establishment and maintenance of human and monkey ES cells are described in, for example, U.S. Pat. No. 5,843,780 B; Thomson J A, et al. (1995), Proc Natl. Acad. Sci. USA. 92: 7844-7848; Thomson J A, et al. (1998), Science. 282: 1145-1147; H. Suemori et al. (2006), Biochem. Biophys. Res. Commun., 345: 926-932; M. Ueno et al. (2006), Proc. Natl. Acad. Sci. USA, 103: 9554-9559; H. Suemori et al. (2001), Dev. Dyn., 222: 273-279; H. Kawasaki et al. (2002), Proc. Natl. Acad. Sci. USA, 99: 1580-1585; and Klimanskaya I, et al. (2006), Nature. 444: 481-485.

With regard to culture medium for preparation of ES cells, human ES cells can be maintained, for example, using DMEM/F-12 culture medium supplemented with 0.1 mM 2-mercaptoethanol, 0.1 mM non-essential amino acids, 2 mM L-glutamic acid, 20% KSR and 4 ng/ml bFGF at 37° C. under a moist atmosphere of 2% $CO_2$/98% air (O. Fumitaka et al. (2008), Nat. Biotechnol., 26:215-224). ES cells are required to be subcultured every 3 to 4 days, and the subculture can be carried out using, for example, 0.25% trypsin and 0.1 mg/ml collagenase IV in PBS containing 1 mM $CaCl_2$ and 20% KSR.

Selection of ES cells can be generally carried out by the Real-Time PCR method using, as an index, expression of a gene marker such as alkaline phosphatase, Oct-3/4, Nanog and the like. In particular, for selection of human ES cells, expression of a gene marker such as OCT-3/4, NANOG, EGAD and the like can be used as an index (E. Kroon et al. (2008), Nat. Biotechnol., 26: 443-452).

With regard to ES cells, as mouse ES cells, various mouse ES cell lines established by inGenious targeting laboratory, Riken (Institute of Physical and Chemical Research) etc., are available, and, as human ES cells, various human ES cell lines established by NIH, Riken, Kyoto University, Cellartis etc., are available. For examples, examples of human ES cell lines include line CHB-1-CHB-12, line RUES1, line RUES2, line-HUES1-HUES28 etc., of NIH, line H1 and line H9 of WisCell Research, and line KhES-1, line KhES-2, line KhES-3, line KhES-4, line KhES-5, line SSES1, line SSES2, line SSES3 etc., of Riken. Alternatively, clinical-grade cell lines, research or clinical cell lines prepared from these cell lines, and the like may be used.

(B) Germline Stem Cells

Germline stem cells are pluripotent stem cells derived from testis, and play a role as the origin for spermatogenesis. Similarly to ES cells, these cells can be induced to differentiate into various series of cells, and, for example, have a property to enable preparation of a chimeric mouse by transplantation of the cells to a mouse blastocyst (M. Kanatsu-Shinohara et al. (2003) Biol. Reprod., 69: 612-616; K. Shinohara et al. (2004), Cell, 119: 1001-1012). Germline stem cells are capable of self-renewal in a culture medium containing glial cell line-derived neurotrophic factor (GDNF), and, by repeating their subculture under the same culture conditions as those for ES cells, germline stem cells can be obtained (Masanori Takehashi et al. (2008), Experimental Medicine, 26(5) (extra edition): 41-46, Yodosha (Tokyo, Japan)).

(C) Embryonic Germ Cells

Embryonic germ cells are established from fetal primordial germ cells and have pluripotency similarly to ES cells. They can be established by culturing primordial germ cells in the presence of substances such as LIF, bFGF, stem cell factor and the like (Y. Matsui et al. (1992), Cell, 70: 841-847; J. L. Resnick et al. (1992), Nature, 359: 550-551).

(D) Induced Pluripotent Stem Cells

The "induced pluripotent stem cell (iPSC)" refers to a cell obtained by introducing a certain factor (nuclear reprogramming factor) into a mammalian somatic cell or an undifferentiated stem cell to perform reprogramming. At present, there are various "induced pluripotent stem cells", and those that can also be used are as follows: an iPSC established by Yamanaka, et al., by introducing four factors, Oct3/4, Sox2, Klf4 and c-Myc into a mouse fibroblast (Takahashi K, Yamanaka S., Cell, (2006) 126: 663-676); as well as an iPSC derived from a human cell established by introducing the same four factors to a human fibroblast (Takahashi K, Yamanaka S., et al. Cell, (2007) 131: 861-872); a Nanog-iPS cell established by introducing the four factors described above and then performing screening with the expression of Nanog as an index (Okita, K., Ichisaka, T., and Yamanaka, S. (2007). Nature 448, 313-317); an iPS cell prepared with a method in which c-Myc is not included (Nakagawa M, Yamanaka S., et al. Nature Biotechnology, (2008) 26, 101-106); and an iPS cell established by introducing six factors with a virus free method (Okita K et al. Nat. Methods 2011 May; 8(5):409-12, Okita K et al. Stem Cells. 31(3):458-66). In addition, an induced pluripotent stem cell prepared by Thomson, et al., which is established by introducing four factors, OCT3/4, SOX2, NANOG and LIN28 (Yu J., Thomson J A. et al., Science (2007) 318: 1917-1920), an induced pluripotent stem cell prepared by Daley, et al. (Park I H, Daley G Q. et al., Nature (2007) 451: 141-146), and an induced pluripotent stem cell prepared by Sakurada, et al. (Japanese Patent Application Laid-Open No. 2008-307007), etc. can also be used.

Besides, any of the induced pluripotent stem cells known in the art described in all published papers (for example, Shi Y., Ding S., et al., Cell Stem Cell, (2008) Vol 3, Issue 5, 568-574; Kim J B., Scholer H R., et al., Nature, (2008) 454, 646-650; Huangfu D., Melton, D A., et al., Nature Biotechnology, (2008) 26, No 7, 795-797), or patents (for example, Japanese Patent Application Laid-Open No. 2008-307007, Japanese Patent Application Laid-Open No. 2008-283972, US 2008-2336610, US 2009-047263, WO 2007-069666, WO 2008-118220, WO 2008-124133, WO 2008-151058, WO 2009-006930, WO 2009-006997, WO 2009-007852) can also be used.

As induced pluripotent cell lines, various iPSC lines established by NIH, Riken, Kyoto University, etc. are available. For example, examples of human iPSC lines include line HiPS-RIKEN-1A, line H1PS-RIKEN-2A, line H1PS-RIKEN-12A and line Nips-B2 of Riken, line 253G1, line 201B7, line 409B2, line 454E2, line 606A1, line 610B1 and line 648A1 of Kyoto University, and the like. Alternatively, clinical-grade cell lines provided by Kyoto University, Cellular Dynamics International etc., research or clinical cell lines prepared from these cell lines, and the like may be used.

The term "somatic cells" used herein means any animal cells (preferably cells of mammals including human) excluding germ-line cells and totipotent cells such as eggs, oocytes, ES cells and the like. Examples of the somatic cells include, but are not limited to, any of fetal somatic cells, neonatal somatic cells, and mature, healthy or diseased somatic cells, as well as any of primary cultured cells, subcultured cells, and established cell lines. Specific examples of the somatic cells include (1) tissue stem cells (somatic stem cells) such as neural stem cells, hematopoietic stem cells, mesenchymal stem cells, dental pulp stem cells and the like; (2) tissue progenitor cells; (3) differentiated cells such as lymphocytes, epithelial cells, endothelial cells, muscle cells, fibroblasts (skin cells etc.), hair cells, hepatic cells, gastric mucosal cells, enterocytes, spleen cells, pancreatic cells (pancreatic exocrine cells etc.), brain cells, lung cells, kidney cells, adipocytes and the like, and the like.

In the present invention, the mammalian individual from which somatic cells are collected is not limited, and preferably human. In cases where the obtained iPS cells are to be used for human regenerative medicine, it is especially preferred to collect somatic cells from the patient himself or another person having the same or substantially the same human leukocyte antigen (HLA) type in view of prevention of the rejection reaction. Here, "substantially the same" HLA type means that the HLA type is matching to an extent which allows survival of transplanted cells by use of an immunosuppressant(s) and/or the like when cells obtained by differentiation induction from iPS cells derived from the somatic cells are transplanted to the patient. For example, it means that the person has the same major HLAs (for example, at the three gene loci HLA-A, HLA-B and HLA-DR) as those of the patient (the same applies hereinafter). On the other hand, in cases where the cells are not administered (transplanted) to human, for example, in a method for testing toxicity of a candidate drug to cardiomyocytes, the origin of the somatic cells to be used as the source of the iPS cells is not limited.

In cases where the iPS cells are used as the source of cells for screening for evaluation of drug sensitivity or side effects of a patient, it is preferred to collect somatic cells from the patient himself or another person who has the same genetic polymorphism(s) associated with the drug sensitivity or the side effects.

(E) ES Cells Derived from Cloned Embryo Obtained by Nuclear Transfer ntES cells are ES cells derived from a cloned embryo prepared by the nuclear transfer technique, and have almost the same properties as those of ES cells derived from fertilized eggs (T. Wakayama et al. (2001), Science, 292: 740-743; S. Wakayama et al. (2005), Biol. Reprod., 72: 932-936; J. Byrne et al. (2007), Nature, 450: 497-502). That is, an ntES (nuclear transfer ES) cell is an ES cell established from the inner cell mass of a blastocyst derived from a cloned embryo obtained by replacement of the nucleus of an unfertilized egg with the nucleus of a somatic cell. For preparation of ntES cells, the combination of the nuclear transfer technique (J. B. Cibelli et al. (1998), Nature Biotechnol., 16: 642-646) and the ES cell preparation technique (described above) is employed (Sayaka Wakayama et al. (2008), Experimental Medicine 26(5) (extra edition), pp. 47-52). In nuclear transfer, reprogramming can be achieved by injecting the nucleus of a somatic cell into a mammalian enucleated unfertilized egg, and culturing the resultant for several hours.

As used herein, the term "cardiomyocyte" means a cell expressing at least one marker gene selected from the group consisting of cardiac troponin (cTNT), αMHC (α myosin heavy chain, MYH6) and βMHC (MYH7). Examples of cTNT include NCBI accession number NM_000364 in a case of human, and NM_001130176 in a case of mouse. Examples of αMHC include NCBI accession number NM_002471 in a case of human, and NM_001164171 in a case of mouse. Examples of βMHC include NCBI accession number NM_000257 in a case of human, and NM_080728 in a case of mouse.

It is known that an isoform switch occurs in which the expression of troponin I1 (TNNI1) is decreased and the expression of troponin I3 (TNNI3) is increased, as cardiomyocytes mature (Fikru B. Bedada, (2014) 3(4): 594-605). As used herein, "cardiomyocyte is matured (mature)" means that at least TNNI3 expression is increased.

With regard to methods of inducing differentiation of pluripotent stem cells into immature cardiomyocytes, cardiomyocytes can be prepared from pluripotent stem cells by, for example, a method reported by Laflamine M A et al. (Laflamme M A & Murry C E, Nature 2011, Review).

Other examples of the method include, but are not limited to, a method in which cardiomyocytes are prepared by formation of cell mass (embryoid bodies) by suspension culture of induced pluripotent stem cells, a method in which cardiomyocytes are prepared in the presence of a substance that suppresses bone morphogenic protein (BMP) signaling (WO 2005/033298), a method in which cardiomyocytes are prepared by addition of Activin A and BMP in this order (WO 2007/002136), a method in which cardiomyocytes are prepared in the presence of a substance that promotes activation of the canonical Wnt signaling pathway (WO 2007/126077), a method in which Flk/KDR-positive cells are isolated from induced pluripotent stem cells, followed by preparation of cardiomyocytes in the presence of cyclosporin A (WO 2009/118928), and the like.

In addition, a method of inducing differentiation into cardiomyocytes using cytokine by embryoid body formation (Yang L, et al., Human cardiovascular progenitor cells develop from a KDR+ embryonic-stem-cell-derived population., Nature., 2008 May 22; 453 (7194):524-8), a method of inducing differentiation into cardiomyocytes by adhesion culture under cytokine-free condition (Lian X, et al., Robust cardiomyocyte differentiation from human pluripotent stem cells via temporal modulation of canonical Wnt signaling., Proc Natl Acad Sci USA., 2012 Jul. 3; 109 (27):E1848-57), a method of inducing differentiation into cardiomyocytes by combination use of adhesion culture and suspension culture under cytokine-free condition (Minami I, et al., A small molecule that promotes cardiac differentiation of human pluripotent stem cells under defined, cytokine- and xeno-free conditions., Cell Rep., 2012 Nov. 29; 2 (5):1448-60) and the like are also suggested.

The medium to obtain immature cardiomyocytes from pluripotent stem cells is not particularly limited, and mediums known per se can be used. Examples thereof include IMDM medium, Medium 199 medium, Eagle's Minimum Essential Medium (EMEM) medium, αMEM medium, Dulbecco's modified Eagle's Medium (DMEM) medium, Ham's F12 medium, RPMI 1640 medium, Fischer's medium, Neurobasal Medium (Life Technologies), StemPro34 (Invitrogen), medium after removal of solution C from StemFit AK02 (AJINOMOTO AK02, 400 mL of solution A and 100 mL of B solution, total 500 mL), Essential 6 medium (Thermo Fischer Scientific) and mixed media thereof, and the like.

Additives known per se can be added to these mediums, depending on cells and cultural conditions. For example, the medium may contain serum, or may be serum-free. If necessary, the medium may contain one or more of serum replacements such as albumin, transferrin, Knockout Serum Replacement (KSR) (serum replacement for FBS during ES cell culture), N2 supplement (Invitrogen), B27 supplement (Invitrogen), fatty acids, insulin, collagen precursors, trace elements, 2-mercaptoethanol, 1-thiolglycerol and the like, and may also contain one or more of substances such as lipids, amino acids, L-glutamine, Glutamax (Invitrogen), non-essential amino acids, vitamins, growth factors, low-molecular-weight compounds, antibiotics, antioxidants, pyruvic acid, buffers, inorganic salts and the like. Among them, the preferred medium is StemPro34 or a medium after removal of solution C from StemFit AK02, each containing transferrin, 1-thiolglycerol, L-glutamine and ascorbic acid, or RPMI1640 containing B27 supplement.

A combination of activin A, BMP4 and bFGF, or CHIR99021 is used as an initial additive for differentiation induction into cardiomyocytes using the above-mentioned medium.

In the case of the combination of activin A, BMP4 and bFGF, the use concentrations of these additives are preferably 1 ng/ml to 100 ng/ml for activin A, 1 ng/ml to 100 ng/ml for BMP4, and 1 ng/ml to 100 ng/ml for bFGF, more preferably 6 ng/ml for activin A, 10 ng/ml for BMP4, and 5 ng/ml for bFGF.

In the case of CHIR99021, the use concentration is preferably 100 nM to 100 µM, more preferably 4 to 6 µM.

After addition of the above-mentioned additive, by adding vascular endothelial growth factor (VEGF) and a Wnt inhibitor to the medium, the pluripotent stem cells can be differentiated into cardiomyocytes.

The concentration of the VEGF to be used is preferably 1 to 100 ng/ml, more preferably 10 ng/ml.

Examples of the Wnt inhibitor include DKK1 protein (e.g., NCBI accession number: NM_012242 in a case of human), sclerostin (e.g., NCBI accession number: NM_025237 in a case of human), IWR-1 (Merck Millipore), IWP-2 (Sigma-Aldrich), IWP-3 (Sigma-Aldrich), IWP-4 (Sigma-Aldrich), PNU-74654 (Sigma-Aldrich), XAV939 (Sigma-Aldrich) and derivatives thereof, and the like. Among them, IWP-3, IWP-4 and IWR-1 are preferably used.

The concentration of the Wnt inhibitor to be used is not particularly limited as long as it inhibits Wnt, and it is preferably 1 nM to 50 µM, particularly preferably 1 to 2 µM.

The culture period for preparation of immature cardiomyocytes from pluripotent stem cells is, for example, 5 to 365 days, preferably 5 to 100 days, more preferably 5 to 60 days, further more preferably 5 to 40 days, still more preferably 5 to 30 days.

The amount of the compound to be used as the cardiomyocyte maturation promoter of the present invention is not particularly limited, and it is, for example, 0.01 to 100 µM, preferably 0.1 to 30 µM, more preferably 1 to 10 µM, per $1 \times 10^4$ to $1 \times 10^7$ cell of immature cardiomyocytes.

The cardiomyocyte maturation promoter of the present invention may contain the specific compound described herein alone or in combination of one or more. Alternatively, the cardiomyocyte maturation promoter of the present invention may contain a combination of one or more of the specific compounds described herein and one or more compounds having an activity to promote the maturation of a cardiomyocyte other than those described herein (e.g., compounds that can be confirmed to have an activity to promote the maturation of a cardiomyocyte according to the methods described in the experimental examples here, for example, 2-methoxy-5-((Z)-2-(3,4,5-trimethoxyphenyl)vinyl)phenol, (1-ethyl-1H-benzotriazol-5-yl)methyl (2-(2-methoxy-4-methylphenyl)-4-methyl-1,3-thiazol-5-yl)carbamate, (2'beta)-22-oxovincaleukoblastine, 2-(2-(4-chlorophenyl)ethyl)-6-(2-furyl)-3H-imidazo[4,5-b]pyridine, 4,5-anhydro-1,2-dideoxy-4-methyl-2-((N-(morpholin-4-ylacetyl)-L-alanyl-O-methyl-L-tyrosyl)amino)-1-phenyl-L-threo-pent-3-ulose, 3-(3-methoxyphenyl)-N7,N7-dimethylisoquinoline-1,7-diamine, methyl 4-(2-benzylbenzoyl)-2,5-dimethyl-1H-pyrrole-3-carboxylate, 2'-(4-aminophenyl)-1H,1'H-2,5'-bibenzimidazol-5-amine, and salts thereof).

As an index of cardiomyocyte maturity, expression level of marker for cardiomyocyte maturation, morphology and structure (e.g., sarcomere, mitochondria), property (e.g., pulsatility, electrophysiological maturity) and the like can be used. These indexes can be confirmed by a method known per se.

For example, the expression level of marker for cardiomyocyte maturation can be analyzed by measuring the expression level of marker gene using PCR; analyzed by the expression level of marker protein using western blot and the like; or analyzed by fluorescent label using microscope or flow cytometry. The index of electrophysiological maturity can be analyzed by the depth of resting membrane potential using patch clamping technique, and the like. The index of sarcomere microstructure or mitochondria can be observed by electronic microscope; analyzed by fluorescent label using microscope or flow cytometry; or function-analyzed by extracellular flux analyzer, and the like.

In one embodiment, the mature cardiomyocytes obtained by using compound (I) of the present invention can be used in cardiac regenerative medicine. For example, a composition comprising cell mass of the cardiomyocytes prepared by the method of the present invention can be administered to the heart of a patient suffering from cardiac disease.

Specifically, the cardiomyocytes obtained by the method of the present invention may be directly transplanted into the heart of a patient suffering from cardiac disease as a cell suspension, or in the form of a cardiomyocyte sheet (single layer or multi layers). For example, WO 2012/133945, WO 2013/137491, WO 2014/192909 and WO 2016/076368 are referred to for the preparation method of cardiomyocyte sheets.

In another embodiment, the cardiomyocytes obtained by using compound (I) of the present invention can also be used for drug screening or drug cardiotoxicity evaluation for the treatment of cardiac disease, since the cardiomyocytes are homogeneously mature. For example, by administering a test drug to the cardiomyocytes obtained by the method of the present invention, and then measuring the response of the cardiomyocytes, the effect and toxicity of the test drug can be evaluated.

In another embodiment, the cardiomyocytes with reduced automaticity, which are obtained by using compound (I) of the present invention, can be used in cardiac regenerative medicine.

EXAMPLES

The present invention is explained in detail in the following by referring to Examples and Experimental Examples. However, the examples do not limit the present invention and the examples can be modified within the scope of the present invention.

The "room temperature" in the following Examples is generally about 10° C. to about 35° C. The ratio for mixed solvent is, unless otherwise specified, a volume mixing ratio and % means wt % unless otherwise specified.

The elution by column chromatography in the Examples was performed under the observation by TLC (Thin Layer Chromatography) unless otherwise specified. In the observation by TLC, 60 $F_{254}$ manufactured by Merck was used as a TLC plate, the solvent used as an elution solvent in column chromatography was used as an eluent, and UV detector was used for the detection. In silica gel column chromatography, the indication of NH means use of aminopropylsilane-bonded silica gel and the indication of Diol means use of 3-(2,3-dihydroxypropoxy)propylsilane-bonded silica gel. In preparative HPLC (high performance liquid chromatography), the indication of CIS means use of octadecyl-bonded silica gel. The ratio for elution solvent is, unless otherwise specified, a volume mixing ratio.

$^1$H NMR was measured by Fourier transform NMR. For the analysis of $^1$H NMR, ACD/SpecManager (trade name) software and the like were used. Peaks of a hydroxyl group, an amino group and the like, having very mild proton peak, are not sometimes described.

MS was measured by LC/MS. As the ionization method, ESI method, or APCI method was used. The data indicates actual measured value (found). While molecular ion peak is generally observed, a fragment ion is sometimes observed. In the case of a salt, a molecular ion peak or fragment ion peak of free form is generally observed.

The unit of sample concentration (c) for optical rotation ($[\alpha]_D$) is g/100 mL.

Elemental analysis value (Anal.) is described as calculated value (Calcd) and actual measured value (Found).

Peaks by powder X-ray diffraction in the Examples mean peaks measured at room temperature by using Ultima IV (Rigaku Corporation, Japan) with Cu Kα radiation as a radiation source.

The measurement conditions are as follows.
Electric pressure/Electric current: 40 kV/50 mA
Scan speed: 6 degrees/min
Scan range of 2 Theta: 2-35 degrees
The crystallinity by powder X-ray diffraction in the Examples was calculated by the Hermans method.

In the following Examples, the following abbreviations are used.
mp: melting point
MS: mass spectrum
M: mol concentration
N: normality
$CDCl_3$: deuterochloroform
DMSO-$d_6$: deuterodimethyl sulfoxide
$^1$H NMR: proton nuclear magnetic resonance
LC/MS: liquid chromatograph mass spectrometer
ESI: electrospray ionization
APCI: atomospheric pressure chemical ionization
THF: tetrahydrofuran
MeOH: methanol
EtOH: ethanol
TEA: triethylamine
DEAD: diethyl (E)-diazene-1,2-dicarboxylate Example 1

2-(2-phenyl-1H-benzimidazol-5-yl)-5-(piperidin-1-yl)isoindolin-1-one

A) 5-(piperidin-1-yl)-2-benzofuran-1(3H)-one

To a mixture of 5-bromo-2-benzofuran-1(3H)-one (25.0 g), piperidine (13.92 mL) and toluene (250 mL) were added palladium acetate (2.63 g), 2,2'-bis(diphenylphosphino)-1,1'-binaphthyl (10.96 g) and cesium carbonate (26.78 g) at room temperature. The mixture was stirred at 100° C. for 12 hr. To a mixture was added dichloromethane, the impurity was removed by filtration through Celite, and the filtrate was concentrated under reduced pressure. The residue was purified by silica gel column chromatography (ethyl acetate/petroleum ether) to give the title compound (13.0 g).

MS: [M+H]$^+$ 218.

B) N-(4-amino-3-nitrophenyl)-2-(hydroxymethyl)-4-(piperidin-1-yl)benzamide

To a mixture of 2-nitrobenzene-1,4-diamine (9.17 g) and THF (200 mL) was added dropwise 2M trimethylaluminium toluene solution (65.89 mL) at 0° C., and the mixture was stirred at room temperature for 1 hr. To the reaction mixture was added a mixture of 5-(piperidin-1-yl)-2-benzofuran-1(3H)-one (13.0 g) and THF (100 mL) at room temperature, and the reaction mixture was stirred at room temperature for 48 hr. To a mixture was added saturated aqueous sodium hydrogencarbonate solution at 0° C., the impurity was removed by filtration through Celite, and the filtrate was extracted with ethyl acetate. The organic layer was separated, washed with saturated brine, dried over anhydrous sodium sulfate, and concentrated under reduced pressure. The residue was purified by silica gel column chromatography (MeOH/dichloromethane) to give the title compound (3.35 g).

MS [M+H]+ 371.

C) 2-(4-amino-3-nitrophenyl)-5-(piperidin-1-yl) isoindolin-1-one

To a mixture of N-(4-amino-3-nitrophenyl)-2-(hydroxymethyl)-4-(piperidin-1-yl)benzamide (3.35 g), tributylphosphine (2.9 mL) and THF (130 mL) was added DEAD (5.12 mL) at room temperature. The mixture was stirred at room-temperature for 16 hr, and the reaction solution was concentrated. To the obtained residue were added water and ethyl acetate, and the resulting solid was collected by filtration, washed with ethyl acetate, and dried to give the title compound (1.68 g).

MS[M+H]$^+$ 353.

D) 2-(3,4-diaminophenyl)-5-(piperidin-1-yl)isoindolin-1-one

To a mixture of 2-(4-amino-3-nitrophenyl)-5-(piperidin-1-yl)isoindolin-1-one (1.68 g) and EtOH (80 mL) was added 10% palladium on carbon (1.68 g) at room temperature. The mixture was stirred under hydrogen atmosphere of 3.4 atm, at room temperature for 12 hr. The catalyst was removed by filtration, and the filtrate was concentrated under reduced pressure to give the title compound (1.0 g).

MS [M+H]$^+$ 323.

E) 2-(2-phenyl-1H-benzimidazol-5-yl)-5-(piperidin-1-yl)isoindolin-1-one

To a mixture of 2-(3,4-diaminophenyl)-5-(piperidin-1-yl)isoindolin-1-one (0.075 g) and THF (2 mL) were added TEA (0.035 mL) and a mixture of benzoyl chloride (0.027 mL) and THF (1 mL) at 0° C. The mixture was stirred at 0° C. for 30 min, and then stirred at room temperature for 1 hr, and the reaction solution was concentrated. The obtained residue was partitioned between ethyl acetate-THF-water, and the organic layer was washed with saturated aqueous sodium hydrogencarbonate solution and saturated brine, dried over anhydrous sodium sulfate, and concentrated under reduced pressure. To the obtained residue were added MeOH (5 mL) and conc, hydrochloric acid (0.3 mL), and the mixture was refluxed for 12 hr, and the reaction solution was concentrated. To the obtained residue was added saturated aqueous sodium hydrogencarbonate solution, and the resulting solid was collected by filtration, washed with ethyl acetate, and dried to give the title compound (0.037 g).

Example 2

2-(2-benzyl-1H-benzimidazol-5-yl)-5-(piperidin-1-yl)isoindolin-1-one

To a mixture of phenylacetaldehyde (0.046 g) and EtOH (2 mL) were added sodium hydrogensulfite (0.181 g) and 2-(3,4-diaminophenyl)-5-(piperidin-1-yl)isoindolin-1-one (0.125 g) at 0° C. The mixture was stirred at room temperature for 16 hr, and the reaction solution was concentrated. To the obtained residue was added water, and the resulting solid was collected by filtration, and washed with water. The residue was purified by HPLC (L-Column 2 ODS, mobile phase: water/acetonitrile (containing 0.1% formic acid)) to give the title compound (0.024 g).

Example 3

2-(2-(4-(benzyloxy)phenyl)-1H-benzimidazol-5-yl)-5-(piperidin-1-yl)isoindolin-1-one To a mixture of 4-(benzyloxy)benzaldehyde (0.082 g) and EtOH (2 mL) were added sodium hydrogensulfite (0.181 g) and 2-(3,4-diaminophenyl)-5-(piperidin-1-yl)isoindolin-1-one (0.125 g) at 0° C. The mixture was stirred at room temperature for 18 hr, and the reaction solution was concentrated. To the residue was added water, and the resulting solid was collected by filtration, washed with water, and dried. The residue was purified by HPLC (L-Column 2 ODS, mobile phase: water/acetonitrile (containing 10 mM ammonium acetate)) to give the title compound (0.030 g).

Example 4

2-(2-(4-hydroxyphenyl)-1H-benzimidazol-5-yl)-5-(piperidin-1-yl) isoindolin-1-one To a mixture of 2-(2-(4-(benzyloxy)phenyl)-1H-benzimidazol-5-yl)-5-(piperidin-1-yl)isoindolin-1-one (0.150 g), MeOH (6 mL) and THF (3 mL) was added 10% palladium on carbon (0.1 g) at room temperature. The mixture was stirred under normal pressure of hydrogen atmosphere, at room temperature for 16 hr. The catalyst was removed by filtration, and the filtrate was concentrated under reduced pressure. The residue was washed with diethyl ether and MeOH, and dried to give the title compound (0.070 g).

Example 5 methyl (4-(5-(l-oxo-5-(piperidin-1-yl)-1,3-dihydro-2H-isoindol-2-yl)-1H-benzimidazol-2-yl)phenoxy) acetate To a mixture of methyl (4-formylphenoxy)acetate (0.120 g) and EtOH (3 mL) were added sodium hydrogensulfite (0.290 g) and 2-(3,4-diaminophenyl)-5-(piperidin-1-yl) isoindolin-1-one (0.2 g) at 0° C. The mixture was stirred at room temperature for 16 hr, and the reaction solution was concentrated. To the obtained residue was added water, and the resulting solid was collected by filtration, washed with water, and dried. The obtained solid was purified by silica gel column chromatography (MeOH/dichloromethane) to give the title compound (0.120 g).

Example 6

(4-(5-(l-oxo-5-(piperidin-1-yl)-1,3-dihydro-2H-isoindol-2-yl)-1H-benzimidazol-2-yl)phenoxy)acetic acid To a mixture of methyl (4-(5-(l-oxo-5-(piperidin-1-yl)-1,3-dihydro-2H-isoindol-2-yl)-1H-benzimidazol-2-yl)phenoxy)acetate (1.3 g), THF (13 mL) and water (13 mL) was added lithium hydroxide (0.330 g) at room temperature. The mixture was stirred at room temperature for 16 hr, and to the reaction solution was added water. The mixture was partitioned between ethyl acetate-water, and the aqueous layer was acidified with IN hydrochloric acid (pH <4). The resulting solid was collected by filtration, washed with water and MeOH, and dried to give the title compound (0.710 g).

Example 8

2-(2-(4-bromophenyl)-1H-benzimidazol-5-yl)-5-(morpholin-4-yl)isoindolin-1-one

A) 5-(4-morpholinyl)-2-benzofuran-1(3H)-one

A mixture of palladium acetate (0.948 g), 2,2'-bis(diphenylphosphino)-1,1'-binaphthyl (3.95 g), cesium carbonate (9.64 g) and toluene (70 mL) was stirred under nitrogen atmosphere for 5 min. To this mixture were added 5-bromo-2-benzofuran-1(3H)-one (9.0 g) and morpholine (4.4 mL), and the mixture was stirred under nitrogen atmosphere at 100° C. for 4 hr. The mixture was cooled, and concentrated under reduced pressure. To the residue was added chloroform, and the insoluble substance was removed by filtration through Celite, and the filtrate was concentrated under reduced pressure. To the residue was added ethyl acetate, and the resulting solid was collected by filtration to give a crude product. The crude product was crystallized from THE and ethyl acetate to give the title compound (6.39 g).

$^1$H NMR (200 MHz, CDCl$_3$) δ 3.31-3.36 (4H, m), 3.85-3.90 (4H, m), 5.22 (2H, s), 6.82 (1H, d, J=1.6 Hz), 7.00 (1H, dd, J=8.8, 2.2 Hz), 7.77 (1H, d, J=8.8 Hz).

B) 2-(4-bromophenyl)-5-nitro-1H-benzimidazole

To a mixture of 4-nitrobenzene-1,2-diamine (5.0 g), triethylamine (5.0 mL) and THE (80 mL) was added dropwise a mixture of 4-bromobenzoyl chloride (7.17 g) and THE (20 mL) at 0° C., and the mixture was stirred for 30 min, and then at room temperature for 1 hr. The mixture was concentrated under reduced pressure, saturated aqueous sodium hydrogencarbonate solution was added thereto, and the resulting solid was collected by filtration, washed with water to give a crude product. To a mixture of this crude product and methanol (100 mL) was added conc, hydrochloric acid (10 mL), and the mixture was stirred at 80° C. for 22 hr, and concentrated under reduced pressure. To the residue was added saturated aqueous sodium hydrogencarbonate solution, and the resulting solid was collected by filtration, and washed successively with water and ethyl acetate to give the title compound (8.84 g).

$^1$H NMR (200 MHz, DMSO-d$_6$) δ 7.71 (2H, d, J=8.8 Hz), 7.81 (1H, dd, J=9.0, 0.6 Hz), 8.17 (1H, dd, J=8.9, 2.3 Hz), 8.28 (2H, d, J=8.8 Hz), 8.50 (1H, d, J=2.0 Hz).

C) 2-(4-bromophenyl)-1H-benzimidazol-5-amine

A mixture of 2-(4-bromophenyl)-5-nitro-1H-benzimidazole (7.68 g), tin(II) chloride dihydrate (27.2 g) and ethanol (300 mL) was stirred at 65° C. for 3 hr. The mixture was cooled to room temperature, adjusted to pH=8 with saturated aqueous sodium hydrogencarbonate solution, and concentrated under reduced pressure. To the residue were added ethyl acetate and water, the insoluble substance was removed by filtration through Celite, and the aqueous layer was separated, and extracted with ethyl acetate. The organic layers were combined, washed with saturated aqueous sodium hydrogencarbonate solution and saturated brine, dried over anhydrous sodium sulfate, and concentrated under reduced pressure. The residue was washed with ethyl acetate to give the title compound (5.61 g).

$^1$H NMR (200 MHz, DMSO-d$_6$) δ 4.96 (2H, br), 6.54 (1H, dd, J=8.7, 2.1 Hz), 6.67 (1H, s), 7.29 (1H, d, J=8.4 Hz), 7.70 (2H, d, J=8.6 Hz), 8.00 (2H, d, J=8.4 Hz), 12.18 (1H, brs).

D) N-(2-(4-bromophenyl)-1H-benzimidazol-5-yl)-2-(hydroxymethyl)-4-(4-morpholinyl)benzamide To a mixture of 2-(4-bromophenyl)-1H-benzimidazol-5-amine (1.0 g) and THF (100 mL) was added dropwise 1M hexane solution (13.9 mL) of dimethylaluminium chloride, and the mixture was stirred for 5 min. 5-(4-Morpholinyl)-2-benzofuran-1(3H)-one (760.9 mg) was added thereto, and the mixture was stirred for 4 days. 0.005N Hydrochloric acid was added thereto by small portions, and the resulting solid was collected by filtration, washed successively with 0.005N hydrochloric acid, water, saturated aqueous sodium hydrogencarbonate solution and water to give a crude product. The product was crystallized from THF-methanol to give the title compound (1.033 g).

$^1$H NMR (300 MHz, DMSO-dg) δ 3.22 (4H, m), 3.77 (4H, m), 4.69 (2H, d, J=4.3 Hz), 5.43 (1H, t, J=4.8 Hz), 6.93 (1H, dd, J=8.7, 2.5 Hz), 7.16 (1H, d, J=2.4 Hz), 7.44 (1H, s), 7.57 (2H, d, J=8.5 Hz), 7.77 (2H, m), 8.09 (2H, d, J=8.5 Hz), 8.20 (1H, s), 10.33 (1H, s), 12.92 (1H, s).

E) 2-(2-(4-bromophenyl)-1H-benzimidazol-5-yl)-5-(morpholin-4-yl)isoindolin-1-one To a mixture of N-(2-(4-bromophenyl)-1H-benzimidazol-5-yl)-2-(hydroxymethyl)-4-(4-morpholinyl)benzamide (0.95 g) and N, N-dimethylformamide (10 mL) was added tributylphosphine (1.75 mL), and then DEAD (1.36 mL) was added dropwise thereto. The mixture was stirred for 1 hr, and the reaction solution was concentrated. To the obtained residue were added ethyl acetate and a small amount of water, and the mixture was heated under reflux for 3 min. The mixture was cooled, and the resulting solid was collected by filtration, washed with ethyl acetate, and dried to give the title compound (807 mg).

$^1$H NMR (300 MHz, DMSO-d$_6$) δ 3.29 (4H, t, J=4.7 Hz), 3.77 (4H, t, J=4.3 Hz), 4.99 (2H, s), 7.11 (2H, m), 7.72 (5H, m), 8.14 (3H, m), 13.00 (1H, s).

Example 17

N-(1,1-dioxido-2,3-dihydro-1-benzothiophen-5-yl)-2-(4-(5-(1-oxo-5-(piperidin-1-yl)-1,3-dihydro-2H-isoindol-2-yl)-1H-benzimidazol-2-yl)phenoxy)acetamide To a mixture of (4-(5-(l-oxo-5-(piperidin-1-yl)-1,3-dihydro-2H-isoindol-2-yl)-1H-benzimidazol-2-yl)phenoxy) acetic acid (15 mg), N,N-diisopropylethylamine (0.027 mL) and N,N-dimethylacetamide (1 mL) was added chloro-N,N,N',N'-bis(tetramethylene)formamidinium hexafluorophosphate (16 mg) at room temperature, and the mixture was stirred at room temperature for 0.5 hr. To a mixture was added 5-amino-2,3-dihydrobenzo[b]thiophene 1,1-dioxide (11.4 mg) at room temperature, and the mixture was stirred for 3 days. The mixture was filtered, and the residue was purified by HPLC (YMCTriartC18, mobile phase: water/acetonitrile (containing 10 mM ammonium bicarbonate)) to give the title compound (8.7 mg).

$^1$H NMR (300 MHz, DMSO-d$_6$) δ 1.57-1.67 (6H, m), 3.36-3.39 (6H, m), 3.53-3.61 (2H, m), 4.87 (2H, s), 4.95

(2H, s), 7.01-7.13 (2H, m), 7.14-7.22 (2H, m), 7.49-7.79 (5H, m), 7.91 (1H, s), 7.98-8.28 (3H, m), 10.57 (1H, brs), 12.78 (1H, brs).

Examples 9-16 and 18-28

To a mixture of (4-(5-(1-oxo-5-(piperidin-1-yl)-1,3-dihydro-2H-isoindol-2-yl)-1H-benzimidazol-2-yl)phenoxy)acetic acid (0.029 g, 0.06 mmol), chloro-N,N,N',N'-bis(tetramethylene)formamidinium hexafluorophosphate (0.030 g) and N,N-dimethylacetamide (1 mL) was added dropwise N,N-diisopropylethylamine (0.052 mL) at room temperature, and the mixture was stirred at room temperature for 0.5 hr. To a mixture was added the corresponding amine (0.12 mmol) at room temperature, and the mixture was stirred for 2 hr. To a mixture was added water (0.5 mL), and the mixture was concentrated at 60° C. The residue was purified by HPLC (YMCTriartC18, mobile phase: water/acetonitrile (containing 10 mM ammonium bicarbonate)) to give the compounds of Examples 9 to 16 and 18 to 28.

Examples 29-38

A mixture of the corresponding amine (0.16 mmol), 2-(4-(5-(5-morpholino-1-oxo-1,3-dihydro-2H-isoindolin-2-yl)-1H-benzimidazol-2-yl)phenoxy)acetic acid (0.039 g, 0.08 mmol) (synthesized according to the methods of Example 1 of Steps A-C. and Examples 5-6, except use of morpholine instead of piperidine), O-(7-azabenzotriazol-1-yl)-N,N,N',N'-tetramethyluroniumhexafluorophosphate (0.037 g), N,N-diisopropylethylamine (0.056 mmol) and N,N-dimethylformamide (1 mL) was stirred at room temperature for 16 hr, and the mixture was concentrated at 60° C. The residue was purified by HPLC (YMCTriartC18, mobile phase: water/acetonitrile (containing 10 mM ammonium bicarbonate)) to give the compounds of Example 29-38.

Example 45

5-(piperidin-1-yl)-2-(2-(pyridin-4-yl)-1H-benzimidazol-5-yl)isoindolin-1-one

To a mixture of 2-(3,4-diaminophenyl)-5-(piperidin-1-yl)isoindolin-1-one (0.125 g) and THF (3 mL) were added TEA (0.119 ml) and a mixture of isonicotinoyl chloride hydrochloride (0.069 g) and THF (2 mL) at 0° C. The mixture was stirred at 0° C. for 30 min, and then at room temperature for 16 hr, and the reaction solution was concentrated. The obtained residue was partitioned between ethyl acetate-THF-water, and the organic layer was washed with saturated aqueous sodium hydrogencarbonate solution and saturated brine, dried over anhydrous sodium sulfate, and concentrated under reduced pressure. To the obtained residue were added MeOH (10 mL) and conc, hydrochloric acid (0.6 mL), and the mixture was refluxed at 70° C. for 16 hr, and the reaction solution was concentrated. To the obtained residue was added saturated aqueous sodium hydrogencarbonate solution, and the resulting solid was collected by filtration to give a crude product. This crude product was purified by HPLC (L-Column 2 ODS, mobile phase: water/acetonitrile (containing 10 mM ammonium bicarbonate)) to give the title compound (32 mg).

$^1$H NMR (500 MHz, DMSO-$d_6$) δ 1.62 (6H, brs), 3.37 (4H, brs), 4.96 (2H, s), 7.07-7.10 (2H, m), 7.57 (1H, d, J=8.2 Hz), 7.69 (2H, q, J=8.7 Hz), 8.09 (2H, d, J=4.6 Hz), 8.19 (1H, s), 8.74 (2H, d, J=4.9 Hz).

Example 46

5-(piperidin-1-yl)-2-(2-(pyridin-3-yl)-1H-benzimidazol-5-yl)isoindolin-1-one

To a mixture of nicotinaldehyde and EtOH were added sodium hydrogensulfite (0.290 g) and 2-(3,4-diaminophenyl)-5-(piperidin-1-yl)isoindolin-1-one (0.200 g) at 0° C. The mixture was stirred at room temperature for 16 hr, and the reaction solution was concentrated. To the obtained residue was added water, and the resulting solid was collected by filtration, washed with water, and dried to give a crude product. This crude product was purified by HPLC (L-Column 2 ODS, mobile phase: water/acetonitrile (containing 10 mM ammonium bicarbonate)) to give the title compound (48 mg).

$^1$H NMR (500 MHz, DMSO-$d_6$) δ 1.62 (6H, brs), 3.37 (4H, brs), 4.96 (2H, d, J=7.0 Hz), 7.07-7.10 (2H, m), 7.56-7.60 (3H, m), 7.72 (0.6H, d, J=8.5 Hz), 7.88 (0.4H, d, J=8.5 Hz), 8.09 (0.4H, brs), 8.29 (0.6H, brs), 8.47-8.51 (1H, m), 8.67-8.68 (1H, m), 9.34-9.36 (1H, m), 13.10 (1H, brs).

The compounds of Examples are shown in the following tables. MS in the tables means actual measured value. The compounds of Examples 7, 39 to 44 and 47 to 73 in the following tables were synthesized according to the methods shown in the above-mentioned Examples or a method analogous thereto.

TABLE 1-1

| Ex.No. | IUPAC NAME | Structure | ADDITIVE | MS |
|---|---|---|---|---|
| 1 | 2-(2-phenyl-1H-benzimidazol-5-yl)-5-(piperidin-1-yl)isoindolin-1-one | 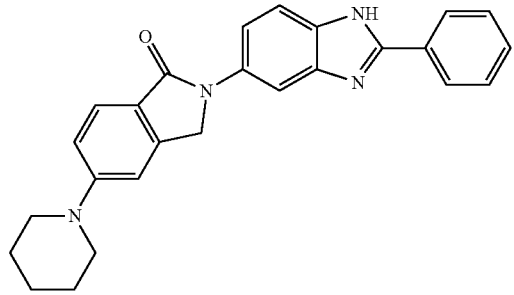 [SMILES: O=C1c2ccc(N3CCCCC3)cc2CN1c1ccc2[nH]c(-c3ccccc3)nc2c1] |  | 409.3 |

TABLE 1-1-continued

| Ex.No. | IUPAC NAME | Structure | ADDITIVE | MS |
|---|---|---|---|---|
| 2 | 2-(2-benzyl-1H-benzimidazol-5-yl)-5-(piperidin-1-yl)isoindolin-1-one | 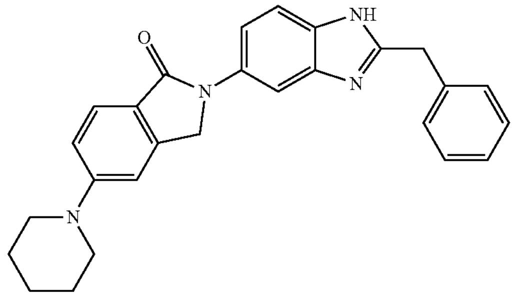 [SMILES: O=C1c2ccc(N3CCCCC3)cc2CN1c1ccc2[nH]c(Cc3ccccc3)nc2c1] | | 423.3 |
| 3 | 2-(2-(4-(benzyloxy)phenyl)-1H-benzimidazol-5-yl)-5-(piperidin-1-yl)isoindolin-1-one | 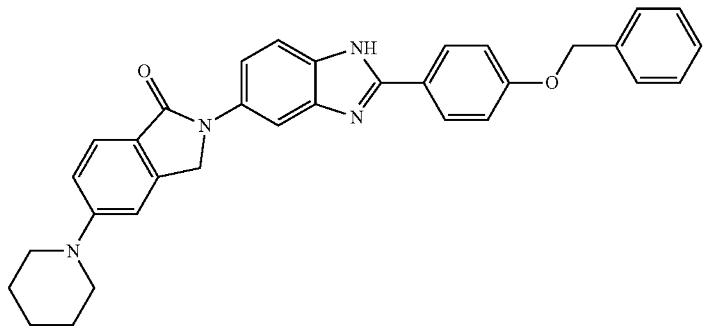 [SMILES: O=C1c2ccc(N3CCCCC3)cc2CN1c1ccc2[nH]c(-c3ccc(OCc4ccccc4)cc3)nc2c1] | | 515.3 |

TABLE 1-2

| Ex.No. | IUPAC NAME | Structure | ADDITIVE | MS |
|---|---|---|---|---|
| 4 | 2-(2-(4-hydroxyphenyl)-1H-benzimidazol-5-yl)-5-(piperidin-1-yl)isoindolin-1-one | 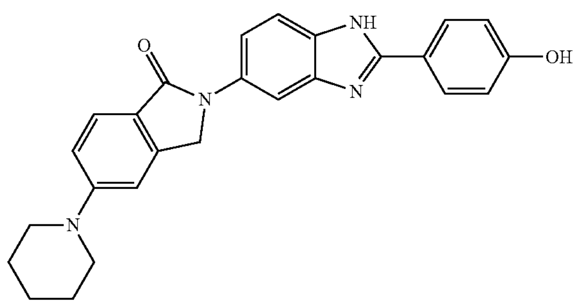 [SMILES: O=C1c2ccc(N3CCCCC3)cc2CN1c1ccc2[nH]c(-c3ccc(O)cc3)nc2c1] | | 425.3 |
| 5 | methyl (5-(5-(1-oxo-5-(piperidin-1-yl)-1,3-dihydro-2H-isoindol-2-yl)-1H-benzimidazol-2-yl)phenoxy)acetate | 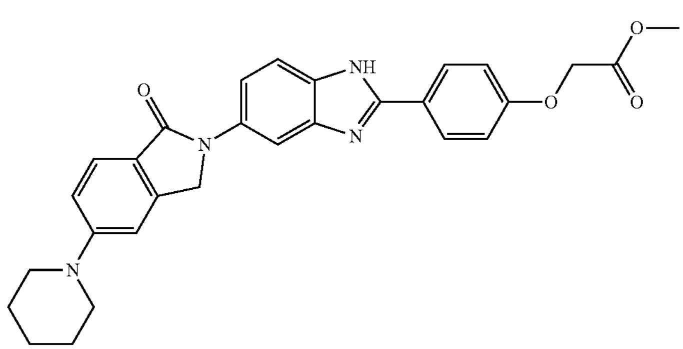 [SMILES: COC(=O)COc1ccc(-c2nc3cc(N4Cc5cc(N6CCCCC6)ccc5C4=O)ccc3[nH]2)cc1] | | 497.3 |

TABLE 1-2-continued

| Ex.No. | IUPAC NAME | Structure | ADDITIVE | MS |
|---|---|---|---|---|
| 6 | (4-(5-(1-oxo-5-(piperidin-1-yl)-1,3-dihydro-2H-isoindol-2-yl)-1H-benzimidazol-2-yl)phenoxy)acetate | 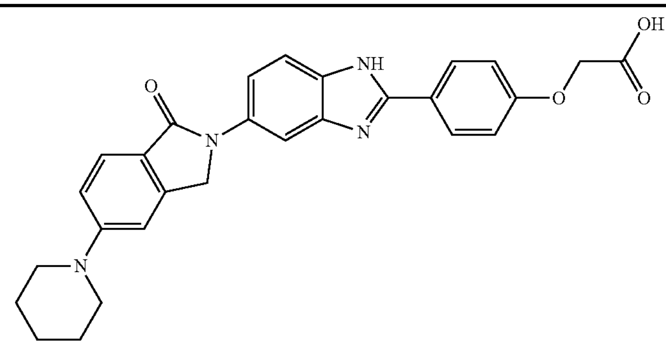 | | 483.2 |

TABLE 1-3

| Ex.No. | IUPAC NAME | Structure | ADDITIVE | MS |
|---|---|---|---|---|
| 7 | 2-(2-(4-methoxyphenyl)-1H-benzimidazol-5-yl)isoindolin-1-one | 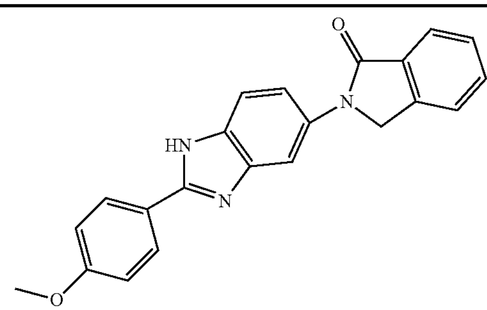 | | 356.2 |
| 8 | 2-(2-(4-bromophenyl)-1H-benzimidazol-5-yl)-5-(morpholin-4-yl)isoindolin-1-one | 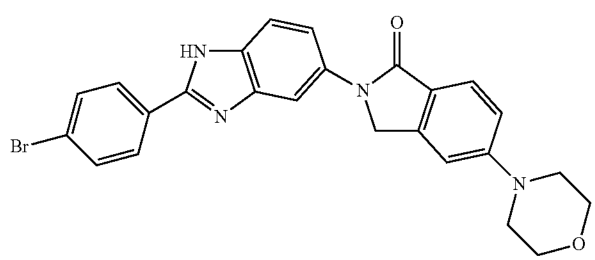 | | 489.1 |
| 9 | 2-(4-(5-(1-oxo-5-(piperidin-1-yl)-1,3-dihydro-2H-isoindol-2-yl)-1H-benzimidazol-2-yl)phenoxy)-N-((2E)-5-phenylpent-2-en-1-yl)acetamide | 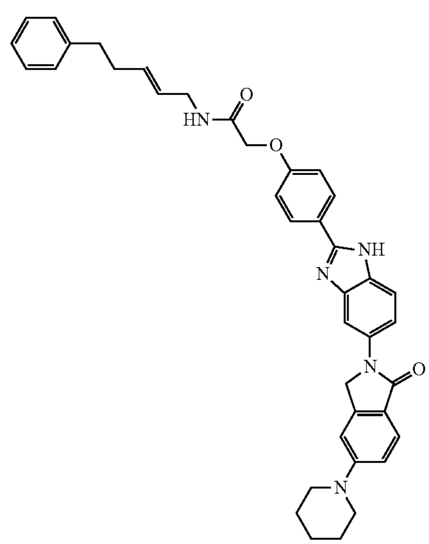 [SMILES: O=C(COc1ccc(-c2nc3cc(N4Cc5cc(N6CCCCC6)ccc5C4=O)ccc3[nH]2)cc1)NC/C=C/CCc1ccccc1] | | 626.4 |

TABLE 1-4

| Ex.No. | IUPAC NAME | Structure | ADDITIVE | MS |
|---|---|---|---|---|
| 10 | N-(2-((3-fluorophenyl)amino)ethyl)-2-(4-(5-(1-oxo-5-(piperidin-1-yl)-1,3-dihydro-2H-isoindol-2-yl)-1H-benzimidazol-2-yl)phenoxy)acetamide | 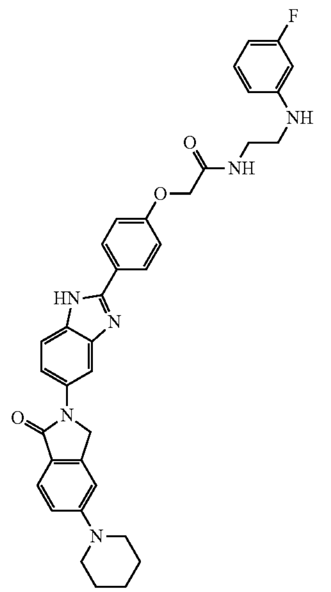 [SMILES: O=C(COc1ccc(-c2nc3cc(N4Cc5cc(N6CCCCC6)ccc5C4=O)ccc3[nH]2)cc1)NCCNc1cccc(F)c1] | | 619.3 |
| 11 | N-methyl-N⁻2⁻-((4-(5-(1-oxo-5-(piperidin-1-yl)-1,3-dihydro-2H-isoindol-2-yl)-1H-benzimidazol-2-yl)phenoxy)acetyl)-N-(2-phenylethyl)glycinamide | 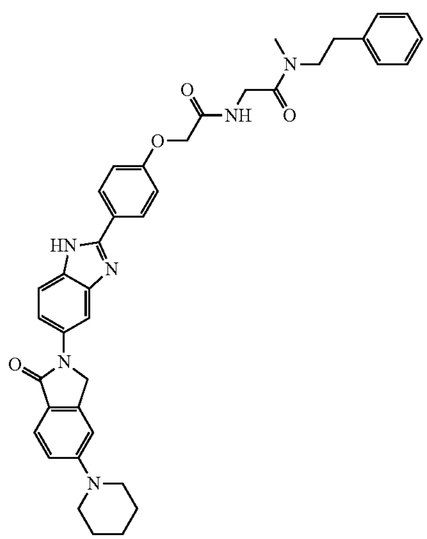 [SMILES: CN(CCc1ccccc1)C(=O)CNC(=O)COc1ccc(-c2nc3cc(N4Cc5cc(N6CCCCC6)ccc5C4=O)ccc3[nH]2)cc1] | | 657.3 |
| 12 | 2-(4-(5-(1-oxo-5-(piperidin-1-yl)-1,3-dihydro-2H-isoindol-2-yl)-1H-benzimidazol-2-yl)phenoxy)-N-(3-(pyridin-4-yl)propyl)acetamide | 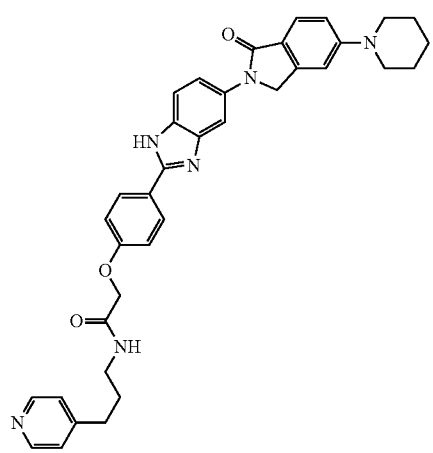 [SMILES: O=C(COc1ccc(-c2nc3cc(N4Cc5cc(N6CCCCC6)ccc5C4=O)ccc3[nH]2)cc1)NCCCc1ccncc1] | | 601.3 |

TABLE 1-5

| Ex.No. | IUPAC NAME | Structure | ADDITIVE | MS |
| --- | --- | --- | --- | --- |
| 13 | N,N-dimethyl-2-(((4-(5-(1-oxo-5-(piperidin-1-yl)-1,3-dihydro-2H-isoindol-2-yl)-1H-benzimidazol-2-yl)phenoxy)acetyl)amino)-2-phenylacetamide | 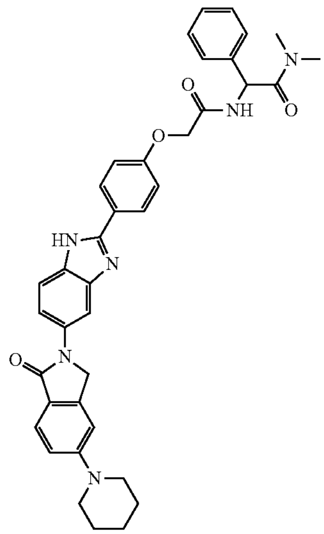 [SMILES: CN(C)C(=O)C(NC(=O)COc1ccc(-c2nc3cc(N4Cc5cc(N6CCCCC6)ccc5C4=O)ccc3[nH]2)cc1)c1ccccc1] | | 643.4 |
| 14 | N-methyl-2-(4-(5-(1-oxo-5-(piperidin-1-yl)-1,3-dihydro-2H-isoindol-2-yl)-1H-benzimidazol-2-yl)phenoxy)-N-(tetrahydro-2H-pyran-4-yl)acetamide | 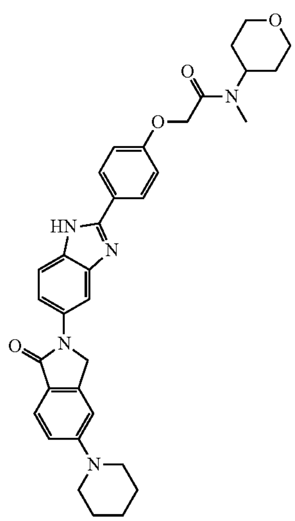 [SMILES: CN(C(=O)COc1ccc(-c2nc3cc(N4Cc5cc(N6CCCCC6)ccc5C4=O)ccc3[nH]2)cc1)C1CCOCC1] | | 580.3 |
| 15 | 2-(2-(4-(2-(4-hydroxy-4-methylpiperidin-1-yl)-2-oxoethoxy)phenyl)-1H-benzimidazol-5-yl)-5-(piperidin-1-yl)isoindolin-1-one | 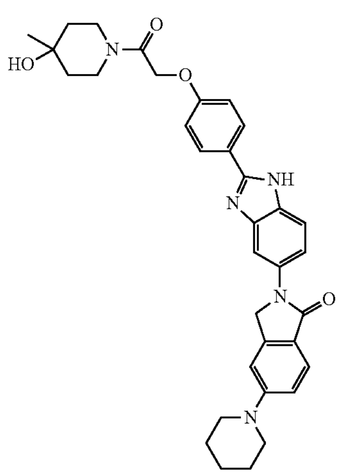 [SMILES: CC1(O)CCN(C(=O)COc2ccc(-c3nc4cc(N5Cc6cc(N7CCCCC7)ccc6C5=O)ccc4[nH]3)cc2)CC1] | | 580.3 |

TABLE 1-6

| Ex.No. | IUPAC NAME | Structure | ADDITIVE | MS |
|---|---|---|---|---|
| 16 | 2-(2-(4-(1,1-dioxido-1,3-thiazolidin-3-yl)-2-oxoethoxy)phenyl)-1H-benzimidazol-5-yl)-5-(piperidin-1-yl)isoindolin-1-one | 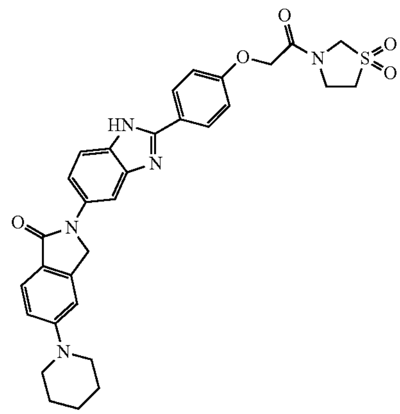 [SMILES: O=C(COc1ccc(-c2nc3cc(N4Cc5cc(N6CCCCC6)ccc5C4=O)ccc3[nH]2)cc1)N1CCS(=O)(=O)C1] | | 586.2 |
| 17 | N-(1,1-dioxido-2,3-dihydro-1-benzothiophen-5-yl)-2-(4-(5-(1-oxo-5-(piperidin-1-yl)-1,3-dihydro-2H-isoindol-2-yl)-1H-benzimidazol-2-yl)phenoxy)acetamide | 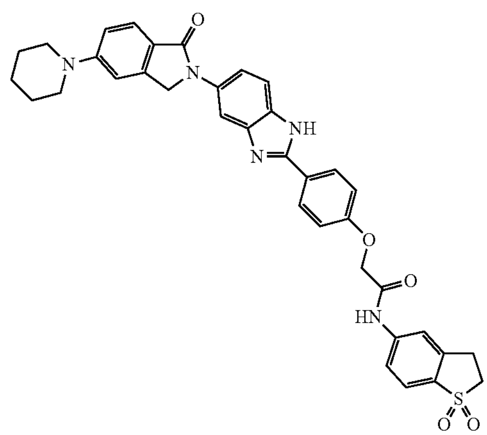 [SMILES: O=C(COc1ccc(-c2nc3cc(N4Cc5cc(N6CCCCC6)ccc5C4=O)ccc3[nH]2)cc1)Nc1ccc2c(c1)CCS2(=O)=O] | | 648.3 |
| 18 | N-(1-methylcyclopropyl)-2-(4-(5-(1-oxo-5-(piperidin-1-yl)-1,3-dihydro-2H-isoindol-2-yl)-1H-benzimidazol-2-yl)phenoxy)acetamide | 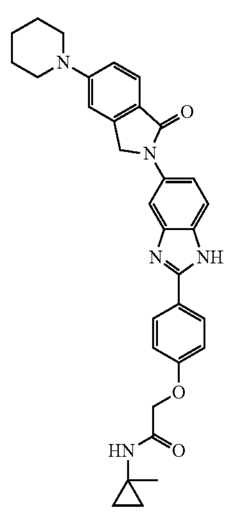 [SMILES: CC1(NC(=O)COc2ccc(-c3nc4cc(N5Cc6cc(N7CCCCC7)ccc6C5=O)ccc4[nH]3)cc2)CC1] | | 536.3 |

TABLE 1-7
| Ex. No. | IUPAC NAME | Structure | ADDITIVE | MS |
|---|---|---|---|---|
| 19 | N-(4-fluorophenyl)-2-(4-(5-(1-oxo-5-(piperidin-1-yl)-1,3-dihydro-2H-isoindol-2-yl)-1H-benzimidazol-2-yl)phenoxy)acetamide | 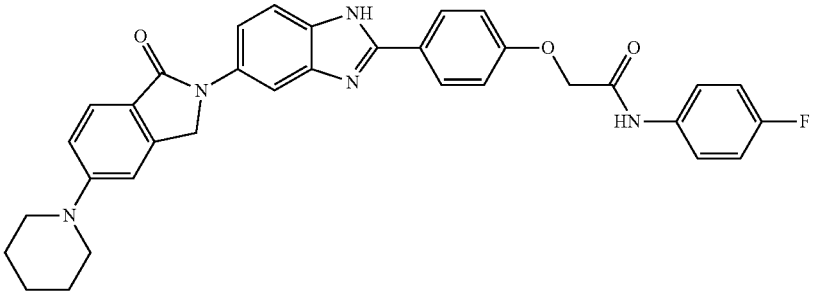 [SMILES: O=C(COc1ccc(-c2nc3cc(N4Cc5cc(N6CCCCC6)ccc5C4=O)ccc3[nH]2)cc1)Nc1ccc(F)cc1] | | 576.3 |
| 20 | N-(2-fluorophenyl)-2-(4-(5-(1-oxo-5-(piperidin-1-yl)-1,3-dihydro-2H-isoindol-2-yl)-1H-benzimidazol-2-yl)phenoxy)acetamide | 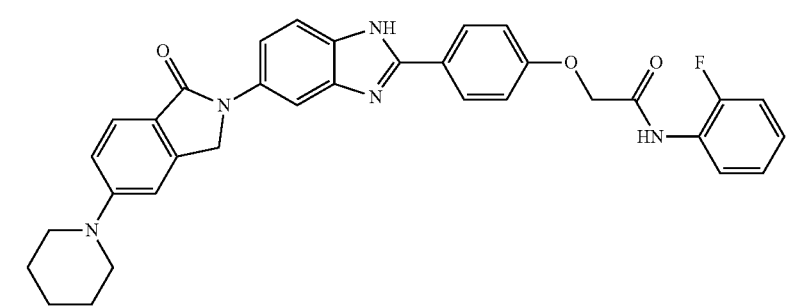 [SMILES: O=C(COc1ccc(-c2nc3cc(N4Cc5cc(N6CCCCC6)ccc5C4=O)ccc3[nH]2)cc1)Nc1ccccc1F] | | 576.2 |
| 21 | N-(4-chlorophenyl)-2-(4-(5-(1-oxo-5-(piperidin-1-yl)-1,3-dihydro-2H-isoindol-2-yl)-1H-benzimidazol-2-yl)phenoxy)acetamide | 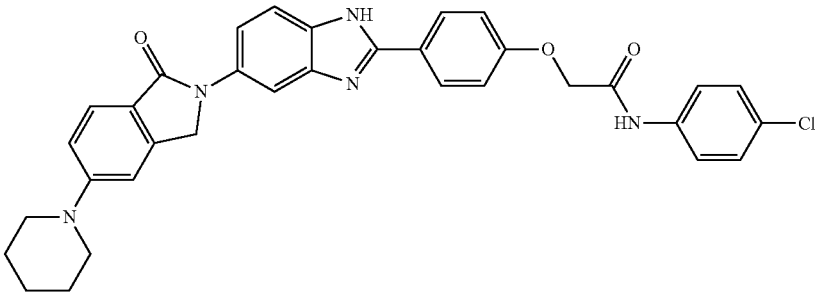 [SMILES: O=C(COc1ccc(-c2nc3cc(N4Cc5cc(N6CCCCC6)ccc5C4=O)ccc3[nH]2)cc1)Nc1ccc(Cl)cc1] | | 592.2 |

TABLE 1-8

| Ex. No. | IUPAC NAME | Structure | ADDITIVE | MS |
|---|---|---|---|---|
| 22 | N-(4-methylphenyl)-2-(4-(5-(1-oxo-5-(piperidin-1-yl)-1,3-dihydro-2H-isoindol-2-yl)-1H-benzimidazol-2-yl)phenoxy)acetamide | 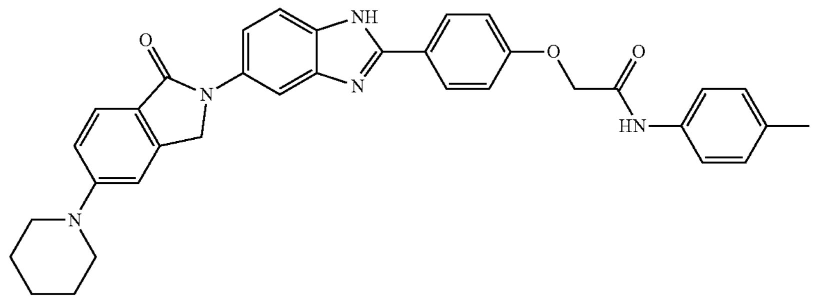 [SMILES: Cc1ccc(NC(=O)COc2ccc(-c3nc4cc(N5Cc6cc(N7CCCCC7)ccc6C5=O)ccc4[nH]3)cc2)cc1] | | 572.2 |
| 23 | N-(3-methylphenyl)-2-(4-(5-(1-oxo-5-(piperidin-1-yl)-1,3-dihydro-2H-isoindol-2-yl)-1H-benzimidazol-2-yl)phenoxy)acetamide | 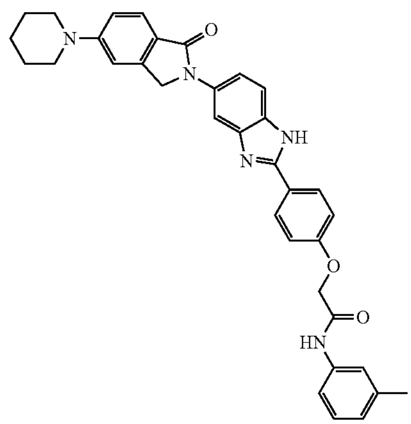 [SMILES: Cc1cccc(NC(=O)COc2ccc(-c3nc4cc(N5Cc6cc(N7CCCCC7)ccc6C5=O)ccc4[nH]3)cc2)c1] | | 572.2 |
| 24 | 2-(4-(5-(1-oxo-5-(piperidin-1-yl)-1,3-dihydro-2H-isoindol-2-yl)-1H-benzimidazol-2-yl)phenoxy)-N-(3-phenylpropyl)acetamide | 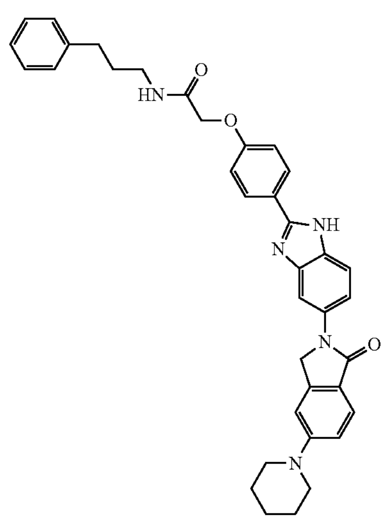 [SMILES: O=C(COc1ccc(-c2nc3cc(N4Cc5cc(N6CCCCC6)ccc5C4=O)ccc3[nH]2)cc1)NCCCc1ccccc1] | | 600.3 |

TABLE 1-9
| Ex.No. | IUPAC NAME | Structure | ADDITIVE | MS |
|---|---|---|---|---|
| 25 | N-cyclopropyl-2-(4-(5-(1-oxo-5-(piperidin-1-yl)-1,3-dihydro-2H-isoindol-2-yl)-1H-benzimidazol-2-yl)phenoxy)acetamide | 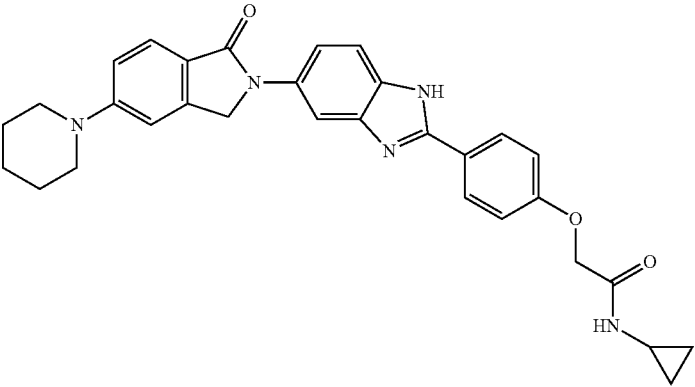 [SMILES: O=C(COc1ccc(-c2nc3cc(N4Cc5cc(N6CCCCC6)ccc5C4=O)ccc3[nH]2)cc1)NC1CC1] | | 522.3 |
| 26 | N-isobutyl-2-(4-(5-(1-oxo-5-(piperidin-1-yl)-1,3-dihydro-2H-isoindol-2-yl)-1H-benzimidazol-2-yl)phenoxy)acetamide | 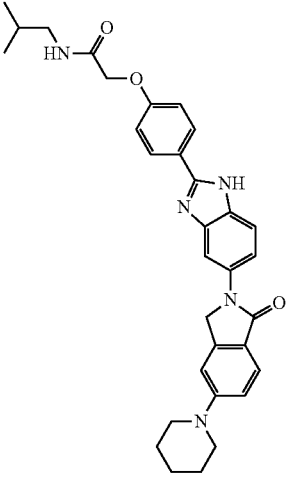 [SMILES: CC(C)CNC(=O)COc1ccc(-c2nc3cc(N4Cc5cc(N6CCCCC6)ccc5C4=O)ccc3[nH]2)cc1] | | 538.3 |
| 27 | N-(cyclopropylmethyl)-2-(4-(5-(1-oxo-5-(piperidin-1-yl)-1,3-dihydro-2H-isoindol-2-yl)-1H-benzimidazol-2-yl)phenoxy)acetamide | 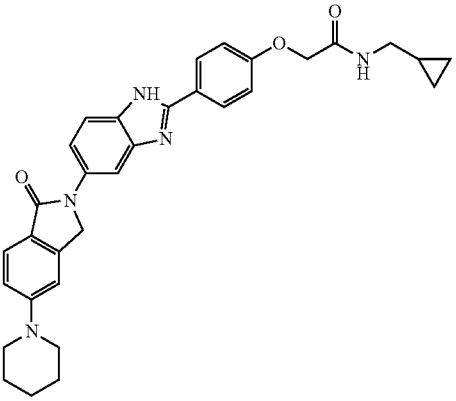 [SMILES: O=C(COc1ccc(-c2nc3cc(N4Cc5cc(N6CCCCC6)ccc5C4=O)ccc3[nH]2)cc1)NCC1CC1] | | 536.3 |

TABLE 1-10
| Ex. No. | IUPAC NAME | Structure | ADDITIVE | MS |
|---|---|---|---|---|
| 28 | 2-(4-(5-(1-oxo-5-(piperidin-1-yl)-1,3-dihydro-2H-isoindol-2-yl)-1H-benzimidazol-2-yl)phenoxy)-N-propylacetamide | 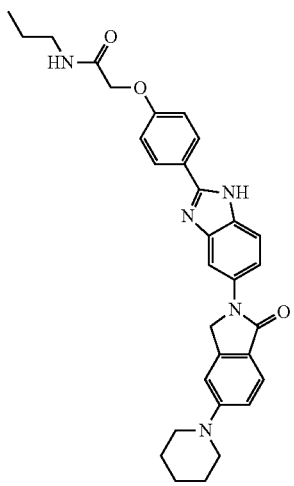 [SMILES: CCCNC(=O)COc1ccc(-c2nc3cc(N4Cc5cc(N6CCCCC6)ccc5C4=O)ccc3[nH]2)cc1] | | 524.3 |
| 29 | N-isopropyl-2-(4-(5-(5-(morpholin-4-yl)-1-oxo-1,3-dihydro-2H-isoindol-2-yl)-1H-benzimidazol-2-yl)phenoxy)acetamide | 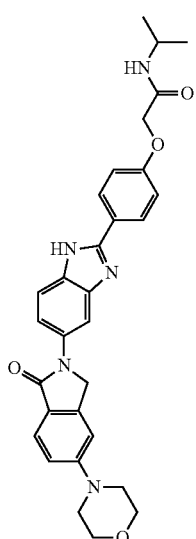 | | 526.2 |
| 30 | 2-(4-(5-(5-(morpholin-4-yl)-1-oxo-1,3-dihydro-2H-isoindol-2-yl)-1H-benzimidazol-2-yl)phenoxy)-N-(tetrahydro-2H-pyran-4-ylmethyl)acetamide | 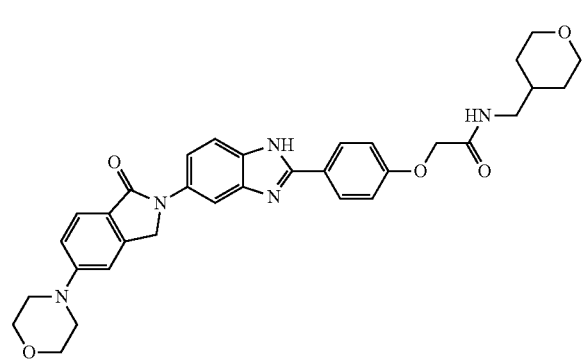 [SMILES: O=C(COc1ccc(-c2nc3cc(N4Cc5cc(N6CCOCC6)ccc5C4=O)ccc3[nH]2)cc1)NCC1CCOCC1] | | 582.3 |

TABLE 1-11

| Ex.No. | IUPAC NAME | Structure | ADDITIVE | MS |
|---|---|---|---|---|
| 31 | 2-(4-(5-(5-(morpholin-4-yl)-1-oxo-1,3-dihydro-2H-isoindol-2-yl)-1H-benzimidazol-2-yl)phenoxy)-N-(tetrahydro-2H-pyran-4-yl)acetamide | 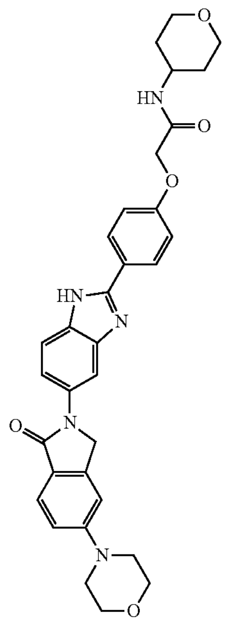 [SMILES: O=C(COc1ccc(-c2nc3cc(N4Cc5cc(N6CCOCC6)ccc5C4=O)ccc3[nH]2)cc1)NC1CCOCC1] | | 568.3 |
| 32 | 5-(morpholin-4-yl)-2-(2-(4-(2-(morpholin-4-yl)-2-oxoethoxy)phenyl)-1H-benzimidazol-5-yl)isoindolin-1-one | 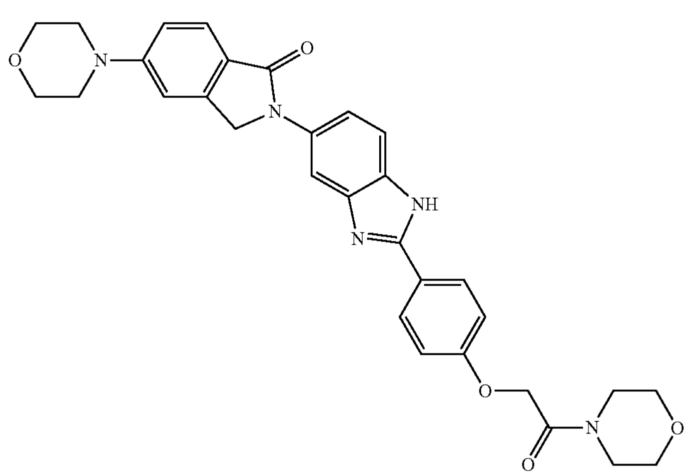 [SMILES: O=C(COc1ccc(-c2nc3cc(N4Cc5cc(N6CCOCC6)ccc5C4=O)ccc3[nH]2)cc1)N1CCOCC1] | | 554.3 |

TABLE 1-11-continued

| Ex.No. | IUPAC NAME | Structure | ADDITIVE | MS |
|---|---|---|---|---|
| 33 | 5-(morpholin-4-yl)-2-(2-(4-(2-oxo-2-(piperidin-1-yl)ethoxy)phenyl)-1H-benzimidazol-5-yl)isoindolin-1-one | 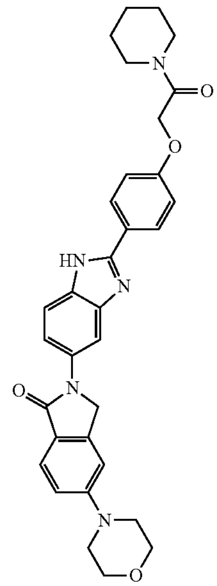 [SMILES: O=C(COc1ccc(-c2nc3cc(N4Cc5cc(N6CCOCC6)ccc5C4=O)ccc3[nH]2)cc1)N1CCCCC1] | | 552.2 |

TABLE 1-12

| Ex. No. | IUPAC NAME | Structure | ADDITIVE | MS |
|---|---|---|---|---|
| 34 | 5-(morpholin-4-yl)-2-(2-(4-(2-oxo-2-(pyrrolidin-1-yl)ethoxy)phenyl)-1H-benzimidazol-5-yl)isoindolin-1-one | 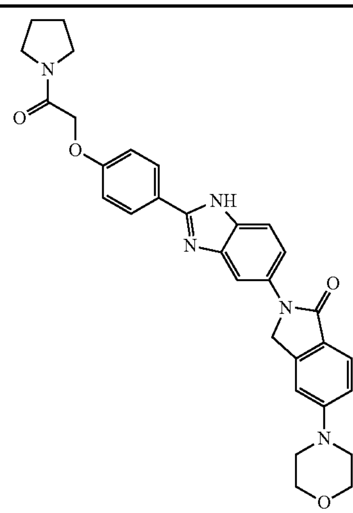 | | 538.3 |
| 35 | 2-(4-(5-(5-(morpholin-4-yl)-1-oxo-1,3-dihydro-2H-isoindol-2-yl)-1H-benzimidazol-2-yl)phenoxy)-N-(pyridin-4-yl)acetamide | 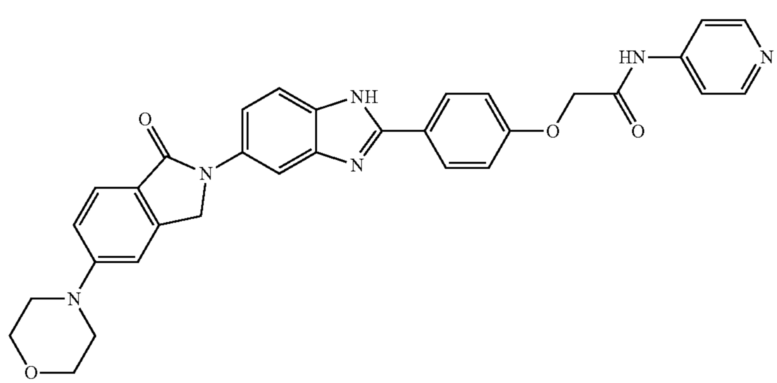 [SMILES: O=C(COc1ccc(-c2nc3cc(N4Cc5cc(N6CCOCC6)ccc5C4=O)ccc3[nH]2)cc1)Nc1ccncc1] | | 561.1 |

TABLE 1-12-continued

| Ex. No. | IUPAC NAME | Structure | ADDITIVE | MS |
|---|---|---|---|---|
| 36 | N-benzyl-2-(4-(5-(5-(morpholin-4-yl)-1-oxo-1,3-dihydro-2H-isoindol-2-yl)-1H-benzimidazol-2-yl)phenoxy)acetamide | 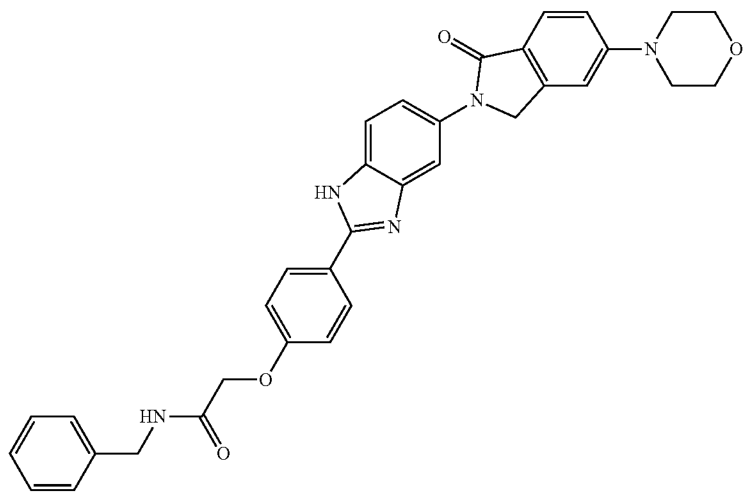 [SMILES: O=C(COc1ccc(-c2nc3cc(N4Cc5cc(N6CCOCC6)ccc5C4=O)ccc3[nH]2)cc1)NCc1ccccc1] | | 574.2 |

TABLE 1-13

| Ex. No. | IUPAC NAME | Structure | ADDITIVE | MS |
|---|---|---|---|---|
| 37 | 2-(4-(5-(5-(rnorpholin-4-yl)-1-oxo-1,3-dihydro-2H-isoindol-2-yl)-1H-benzimidazol-2-yl)phenoxy)-N-phenylacetamide | 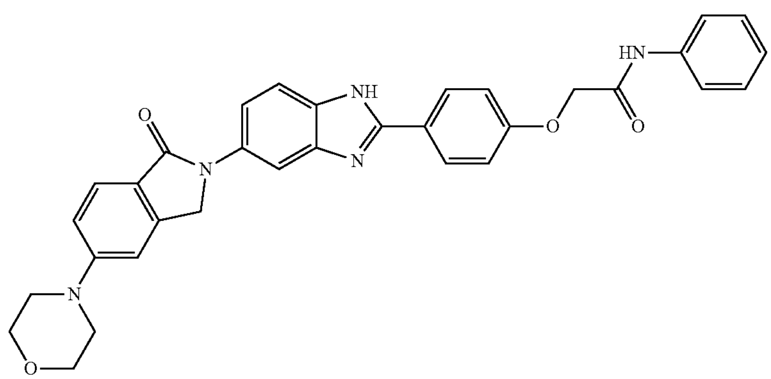 [SMILES: O=C(COc1ccc(-c2nc3cc(N4Cc5cc(N6CCOCC6)ccc5C4=O)ccc3[nH]2)cc1)Nc1ccccc1] | | 560.2 |
| 38 | N,N-dimethyl-2-(4-(5-(5-(morpholin-4-yl)-1-oxo-1,3-dihydro-2H-isoindol-2-yl)-1H-benzimidazol-2-yl)phenoxy)acetamide | 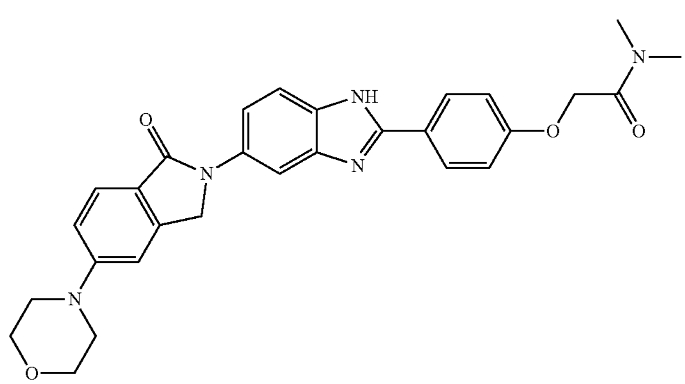 [SMILES: CN(C)C(=O)COc1ccc(-c2nc3cc(N4Cc5cc(N6CCOCC6)ccc5C4=O)ccc3[nH]2)cc1] | | 512.3 |

TABLE 1-13-continued

| Ex. No. | IUPAC NAME | Structure | ADDITIVE | MS |
|---|---|---|---|---|
| 39 | 5-(piperidin-1-yl)-2-(2-(piperidin-4-yl)-1H-benzimidazol-5-yl)isoindolin-1-one | 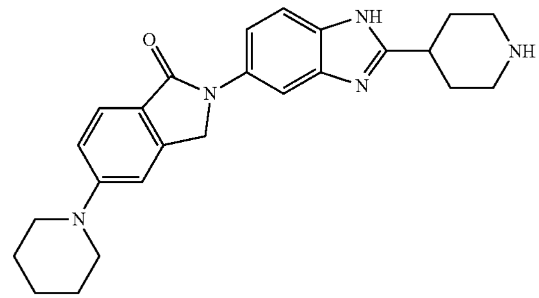 [SMILES: O=C1c2ccc(N3CCCCC3)cc2CN1c1ccc2[nH]c(C3CCNCC3)nc2c1] | HCl | 416.3 |

TABLE 1-14

| Ex.No. | IUPAC NAME | Structure | ADDITIVE | MS |
|---|---|---|---|---|
| 40 | 2-(2-(1,2-oxazol-5-yl)-1H-benzimidazol-5-yl)-5-(piperidin-1-yl)isoindolin-1-one | 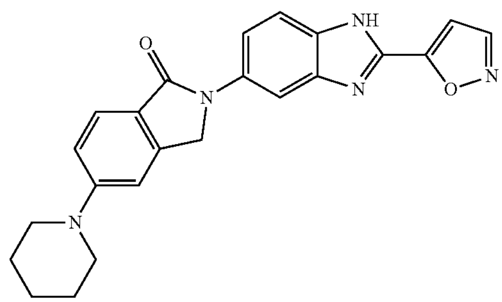 [SMILES: O=C1c2ccc(N3CCCCC3)cc2CN1c1ccc2[nH]c(-c3ccno3)nc2c1] | | 400.2 |
| 41 | 5-(piperidin-1-yl)-2-(2-(2-thienyl)-1H-benzimidazol-5-yl)isoindolin-1-one | 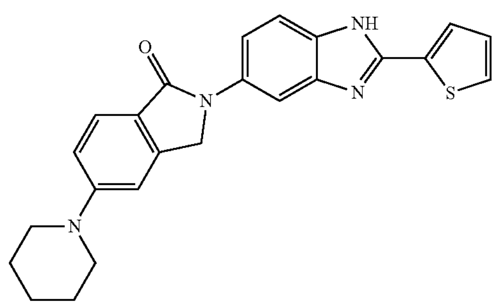 [SMILES: O=C1c2ccc(N3CCCCC3)cc2CN1c1ccc2[nH]c(-c3cccs3)nc2c1] | | 415.3 |
| 42 | tert-butyl 4-(5-(1-oxo-5-(piperidin-1-yl)-1,3-dihydro-2H-isoindol-2-yl)-1H-benzimidazol-2-yl)piperidine-1-carboxylate | 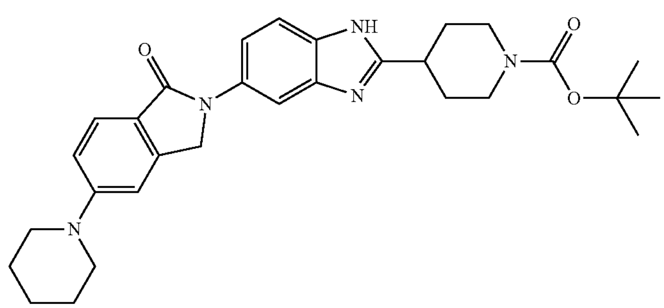 [SMILES: CC(C)(C)OC(=O)N1CCC(c2nc3cc(N4Cc5cc(N6CCCCC6)ccc5C4=O)ccc3[nH]2)CC1] | | 516.3 |

TABLE 1-15

| Ex.No. | IUPAC NAME | Structure | ADDITIVE | MS |
|---|---|---|---|---|
| 43 | 5-(piperidin-1-yl)-2-(2-(tetrahydro-2H-pyran-4-yl)-1H-benzimidazol-5-yl)isoindolin-1-one | 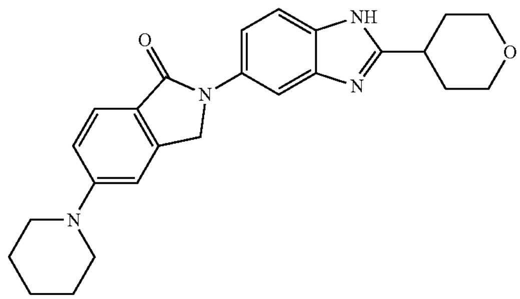 [SMILES: O=C1c2ccc(N3CCCCC3)cc2CN1c1ccc2[nH]c(C3CCOCC3)nc2c1] | | 417.3 |
| 44 | 2-(2-cyclohexyl-1H-benzimidazol-5-yl)-5-(piperidin-1-yl)isoindolin-1-one | 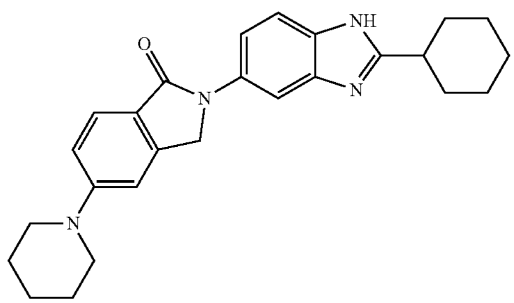 [SMILES: O=C1c2ccc(N3CCCCC3)cc2CN1c1ccc2[nH]c(C3CCCCC3)nc2c1] | | 415.4 |
| 45 | 5-(piperidin-1-yl)-2-(2-(pyridin-4-yl)-1H-benzimidazol-5-yl)isoindolin-1-one | 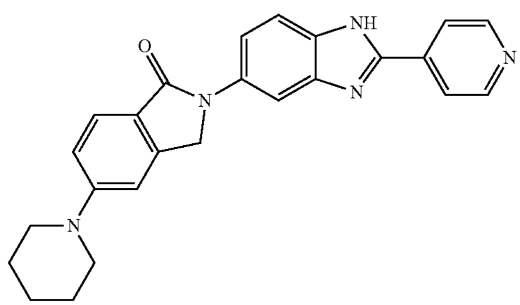 [SMILES: O=C1c2ccc(N3CCCCC3)cc2CN1c1ccc2[nH]c(-c3ccncc3)nc2c1] | | 410.3 |

TABLE 1-16

| Ex.No. | IUPAC NAME | Structure | ADDITIVE | MS |
|---|---|---|---|---|
| 46 | 5-(piperidin-1-yl)-2-(2-(pyridin-3-yl)-1H-benzimidazol-5-yl)isoindolin-1-one | 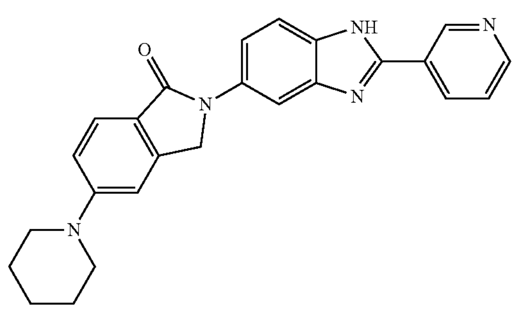 [SMILES: O=C1c2ccc(N3CCCCC3)cc2CN1c1ccc2[nH]c(-c3cccnc3)nc2c1] | | 410.3 |

TABLE 1-16-continued

| Ex.No. | IUPAC NAME | Structure | ADDITIVE | MS |
|---|---|---|---|---|
| 47 | 5-(piperidin-1-yl)-2-(2-(pyridin-2-yl)-1H-benzimidazol-5-yl)isoindolin-1-one | 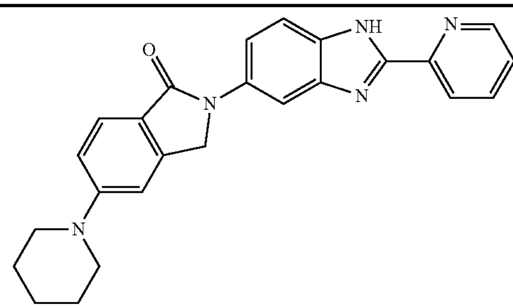 | | 410.3 |
| 48 | 2-(2-(4-isopropoxyphenyl)-1H-benzimidazol-5-yl)-5-(piperidin-1-yl)isoindolin-1-one | 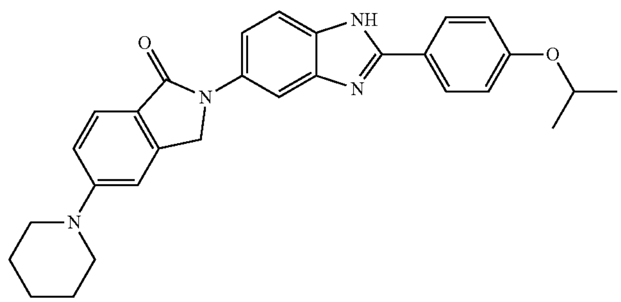 [SMILES: CC(C)Oc1ccc(-c2nc3cc(N4Cc5cc(N6CCCCC6)ccc5C4=O)ccc3[nH]2)cc1] | | 467.3 |

TABLE 1-17

| Ex. No. | IUPAC NAME | Structure | ADDITIVE | MS |
|---|---|---|---|---|
| 49 | 2-(4-(5-(5-(morpholin-4-yl)-1-oxo-1,3-dihydro-2H-isoindol-2-yl)-1H-benzimidazol-2-yl)phenoxy)-N-propylacetannide | 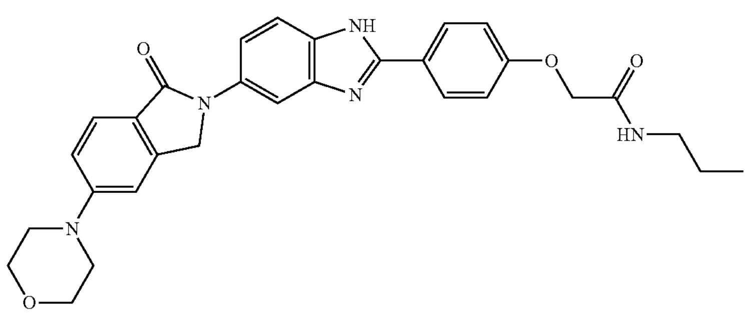 [SMILES: CCCNC(=O)COc1ccc(-c2nc3cc(N4Cc5cc(N6CCOCC6)ccc5C4=O)ccc3[nH]2)cc1] | | 526.3 |
| 50 | methyl (4-(5-(5-(morpholin-4-yl)-1-oxo-1,3-dihydro-2H-isoindol-2-yl)-1H-benzimidazol-2-yl)phenoxy)acetate | 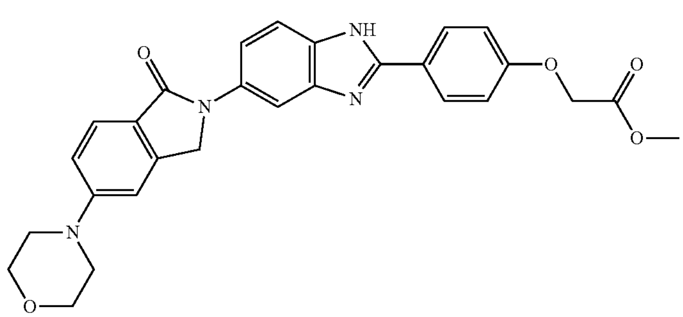 [SMILES: COC(=O)COc1ccc(-c2nc3cc(N4Cc5cc(N6CCOCC6)ccc5C4=O)ccc3[nH]2)cc1] | | 499.2 |

TABLE 1-17-continued

| Ex. No. | IUPAC NAME | Structure | ADDITIVE | MS |
|---|---|---|---|---|
| 51 | (4-(5-(5-(morpholin-4-yl)-1-oxo-1,3-dihydro-2H-isoindol-2-yl)-1H-benzimidazol-2-yl)phenoxy)acetic acid | 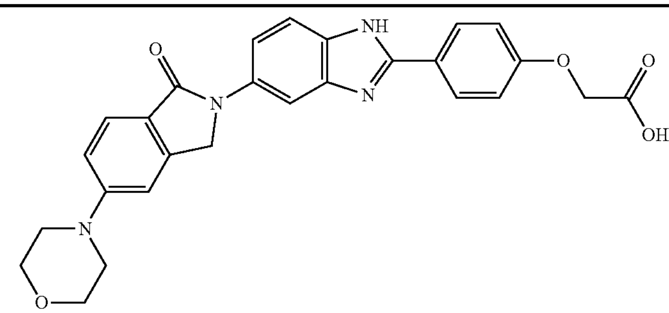 | | 485.2 |

TABLE 1-18

| Ex. No. | IUPAC NAME | Structure | ADDITIVE | MS |
|---|---|---|---|---|
| 52 | benzyl (4-(5-(5-(morpholin-4-yl)-1-oxo-1,3-dihydro-2H-isoindol-2-yl)-1H-benzimidazol-2-yl)phenoxy)acetate | 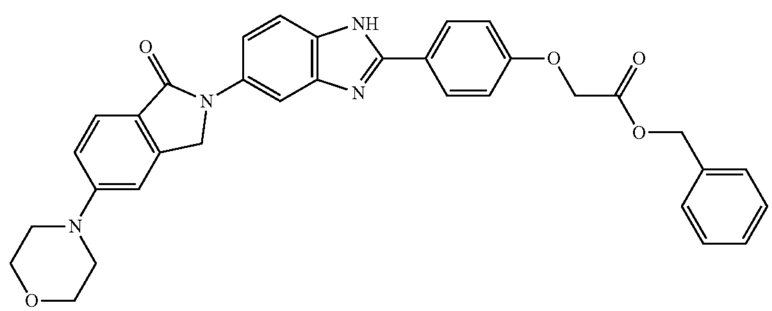 [SMILES: O=C(COc1ccc(-c2nc3cc(N4Cc5cc(N6CCOCC6)ccc5C4=O)ccc3[nH]2)cc1)OCc1ccccc1] | | 575.2 |
| 53 | 2-(2-(4-hydroxyphenyl)-1H-benzimidazol-5-yl)-5-(morpholin-4-yl)isoindolin-1-one | 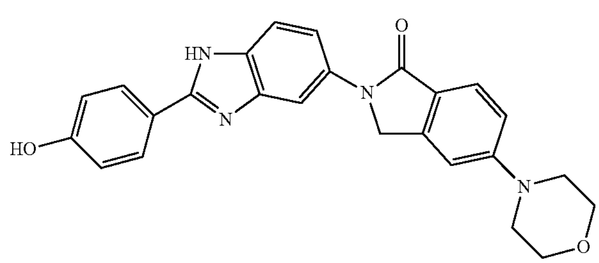 [SMILES: O=C1c2ccc(N3CCOCC3)cc2CN1c1ccc2[nH]c(-c3ccc(O)cc3)nc2c1] | | 427.3 |
| 54 | 2-(2-(4-(hexyloxy)phenyl)-1H-benzimidazol-5-yl)-5-(morpholin-4-yl)isoindolin-1-one | 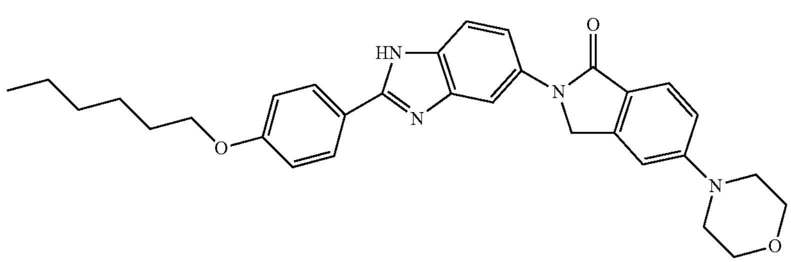 [SMILES: CCCCCCOc1ccc(-c2nc3cc(N4Cc5cc(N6CCOCC6)ccc5C4=O)ccc3[nH]2)cc1] | | 511.4 |

TABLE 1-19

| Ex.No. | IUPAC NAME | Structure | ADDITIVE | MS |
|---|---|---|---|---|
| 55 | 2-(2-(4-(benzyloxy)phenyl)-1H-benzimidazol-5-yl)-5-(morpholin-4-yl)isoindolin-1-one | 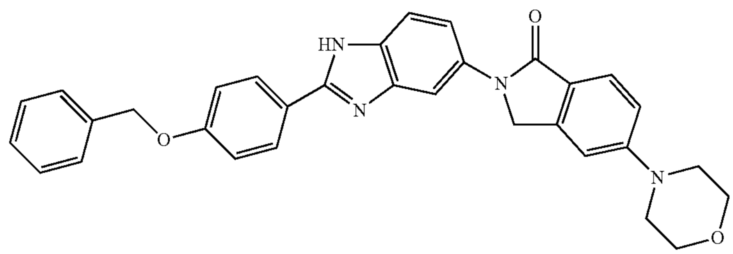 [SMILES: O=C1c2ccc(N3CCOCC3)cc2CN1c1ccc2[nH]c(-c3ccc(OCc4ccccc4)cc3)nc2c1] | | 517.3 |
| 56 | 2-(2-(4-chlorophenyl)-1H-benzimidazol-5-yl)-5-(morpholin-4-yl)isoindolin-1-one | 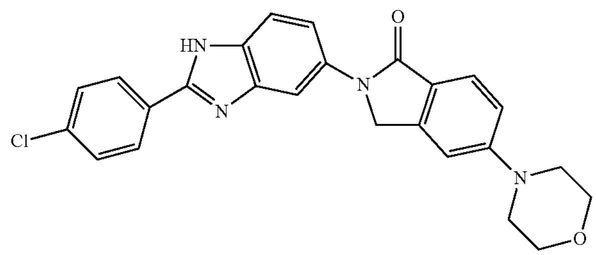 [SMILES: O=C1c2ccc(N3CCOCC3)cc2CN1c1ccc2[nH]c(-c3ccc(Cl)cc3)nc2c1] | | 445.2 |
| 57 | 2-(2-(4-ethoxybenzyl)-1H-benzimidazol-5-yl)-5-(morpholin-4-yl)isoindolin-1-one | 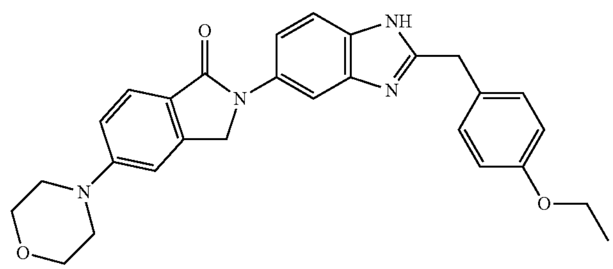 [SMILES: CCOc1ccc(Cc2nc3cc(N4Cc5cc(N6CCOCC6)ccc5C4=O)ccc3[nH]2)cc1] | | 469.3 |

TABLE 1-20

| Ex.No. | IUPAC NAME | Structure | ADDITIVE | MS |
|---|---|---|---|---|
| 58 | 5-(morpholin-4-yl)-2-(2-(4-propoxyphenyl)-1H-benzimidazol-5-yl)isoindolin-1-one | 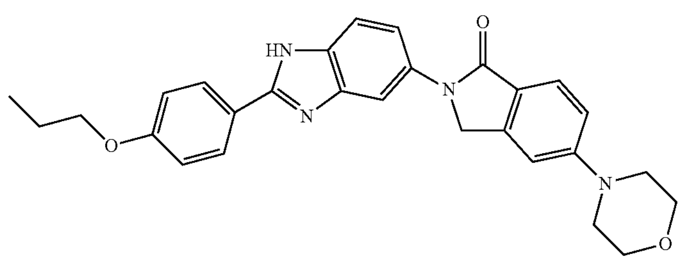 [SMILES: CCCOc1ccc(-c2nc3cc(N4Cc5cc(N6CCOCC6)ccc5C4=O)ccc3[nH]2)cc1] | | 469.3 |
| 59 | 2-(2-(4-ethoxyphenyl)-1-methyl-1H-benzimidazol-5-yl)-5-(morpholin-4-yl)isoindolin-1-one | 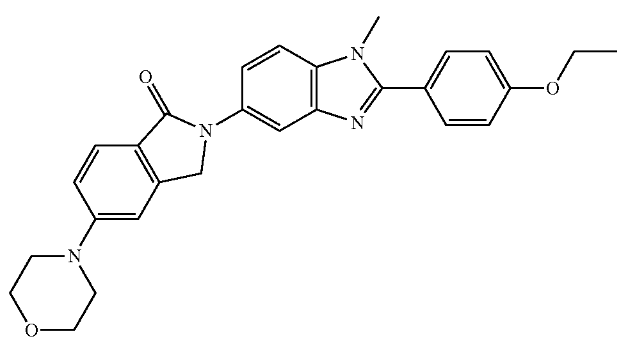 [SMILES: CCOc1ccc(-c2nc3cc(N4Cc5cc(N6CCOCC6)ccc5C4=O)ccc3n2C)cc1] | | 469.3 |

TABLE 1-20-continued

| Ex.No. | IUPAC NAME | Structure | ADDITIVE | MS |
|---|---|---|---|---|
| 60 | 2-(2-(4-ethoxyphenyl)-1-methyl-1H-benzimidazol-6-yl)-5-(morpholin-4-yl)isoindolin-1-one | 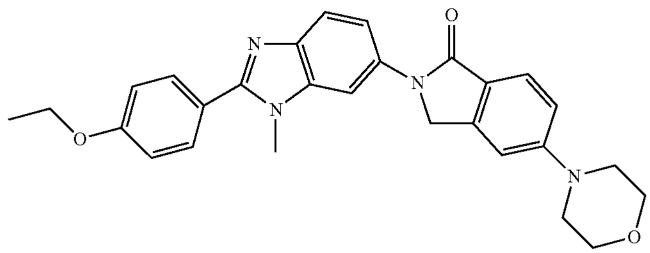 [SMILES: CCOc1ccc(-c2nc3ccc(N4Cc5cc(N6CCOCC6)ccc5C4=O)cc3n2C)cc1] | | 469.3 |

TABLE 1-21

| Ex.No. | IUPAC NAME | Structure | ADDITIVE | MS |
|---|---|---|---|---|
| 61 | 5-(dimethylamino)-2-(2-(4-ethoxyphenyl)-1H-benzimidazol-5-yl)isoindolin-1-one | 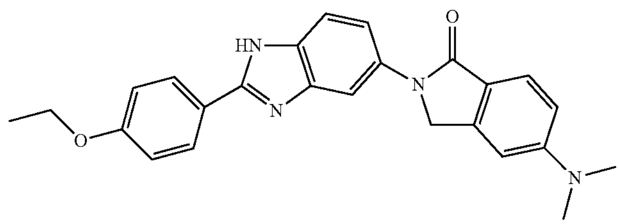 [SMILES: CCOc1ccc(-c2nc3cc(N4Cc5cc(N(C)C)ccc5C4=O)ccc3[nH]2)cc1] | | 413.3 |
| 62 | 2-(2-(4-ethoxyphenyl)-1H-benzimidazol-5-yl)-5-(4-methylpiperazin-1-yl)isoindolin-1-one | 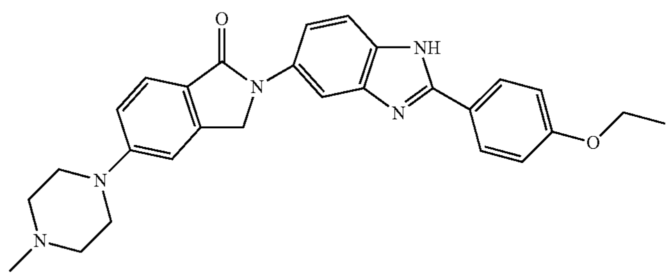 [SMILES: CCOc1ccc(-c2nc3cc(N4Cc5cc(N6CCN(C)CC6)ccc5C4=O)ccc3[nH]2)cc1] | | 468.3 |
| 63 | 2-(2-(4-ethoxyphenyl)-1H-benzimidazol-5-yl)-5-(1H-pyrrol-1-yl)isoindolin-1-one | 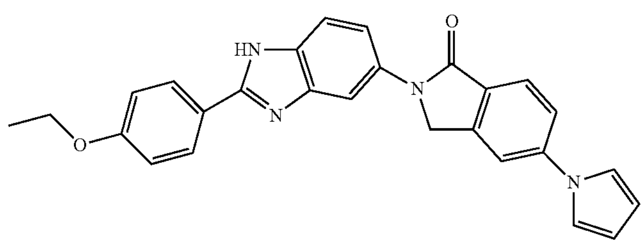 [SMILES: CCOc1ccc(-c2nc3cc(N4Cc5cc(-n6cccc6)ccc5C4=O)ccc3[nH]2)cc1] | | 435.2 |

TABLE 1-22

| Ex.No. | IUPAC NAME | Structure | ADDITIVE | MS |
|---|---|---|---|---|
| 64 | 5-(diethylamino)-2-(2-(4-ethoxyphenyl)-1H-benzimidazol-5-yl)isoindolin-1-one | 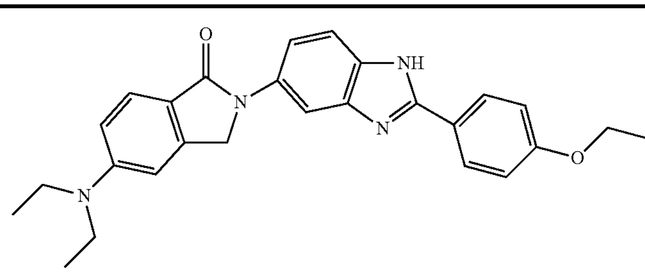 | | 441.3 |

TABLE 1-22-continued

| Ex.No. | IUPAC NAME | Structure | ADDITIVE | MS |
|---|---|---|---|---|
| 65 | 2-(2-(4-ethoxyphenyl)-1H-benzimidazol-5-yl)-5-(piperidin-1-yl)isoindolin-1-one | 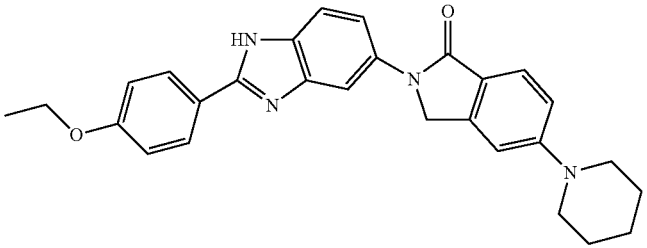 [SMILES: CCOc1ccc(-c2nc3cc(N4Cc5cc(N6CCCCC6)ccc5C4=O)ccc3[nH]2)cc1] | | 453.3 |
| 66 | 2-(2-(4-(methoxymethyl)phenyl)-1H-benzimidazol-5-yl)-5-(morpholin-4-yl)isoindolin-1-one | 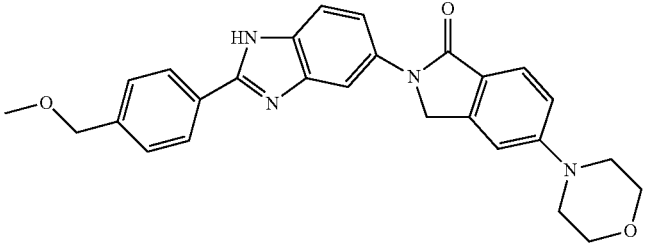 [SMILES: COCc1ccc(-c2nc3cc(N4Cc5cc(N6CCOCC6)ccc5C4=O)ccc3[nH]2)cc1] | | 455.3 |

TABLE 1-23

| Ex.No. | IUPAC NAME | Structure | ADDITIVE | MS |
|---|---|---|---|---|
| 67 | 2-(2-(4-fluorophenyl)-1H-benzimidazol-5-yl)-5-(morpholin-4-yl)isoindolin-1-one | 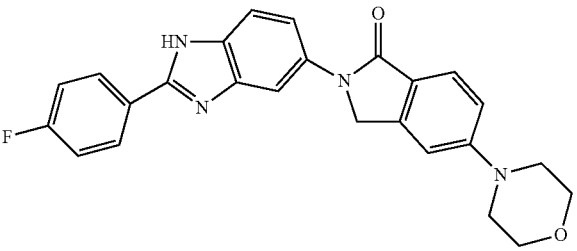 [SMILES: O=C1c2ccc(N3CCOCC3)cc2CN1c1ccc2[nH]c(-c3ccc(F)cc3)nc2c1] | | 429.3 |
| 68 | 2-(2-(4-methoxyphenyl)-1H-benzimidazol-5-yl)-5-(piperidin-1-yl)isoindolin-1-one | 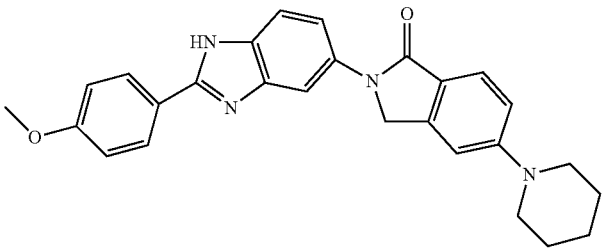 [SMILES: COc1ccc(-c2nc3cc(N4Cc5cc(N6CCCCC6)ccc5C4=O)ccc3[nH]2)cc1] | | 439.3 |
| 69 | 2-(2-(4-methoxyphenyl)-1H-benzimidazol-5-yl)-5-(morpholin-4-yl)isoindolin-1-one | 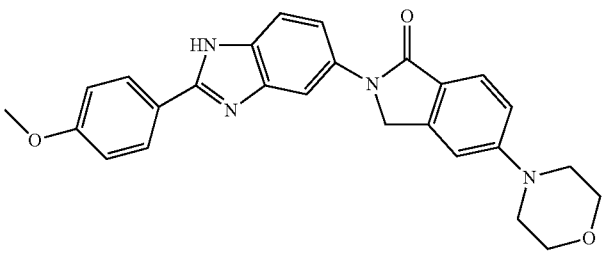 | | 441.3 |

TABLE 1-24

| Ex.No. | IUPAC NAME | Structure | ADDITIVE | MS |
|---|---|---|---|---|
| 70 | 5-bromo-2-(2-(4-methoxyphenyl)-1H-benzimidazol-5-yl)isoindolin-1-one | 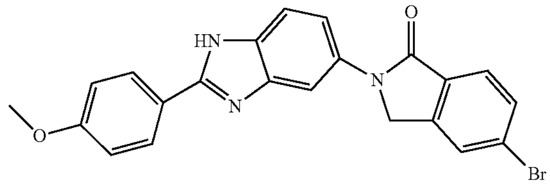 [SMILES: COc1ccc(-c2nc3cc(N4Cc5cc(Br)ccc5C4=O)ccc3[nH]2)cc1] | | 434.1 |
| 71 | 5-(diethylamino)-2-(2-(4-methoxyphenyl)-1H-benzimidazol-5-yl)isoindolin-1-one | 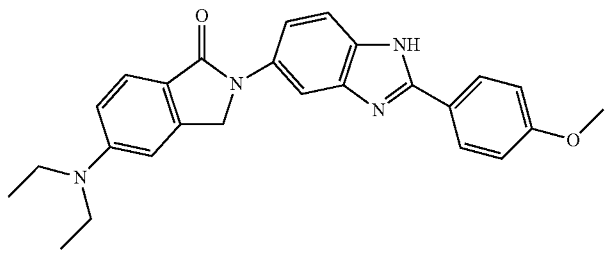 [SMILES: CCN(CC)c1ccc2c(c1)CN(c1ccc3[nH]c(-c4ccc(OC)cc4)nc3c1)C2=O] | | 427.3 |
| 72 | 2-(2-(4-ethoxyphenyl)-1H-benzimidazol-5-yl)-5-(morpholin-4-yl)isoindolin-1-one | 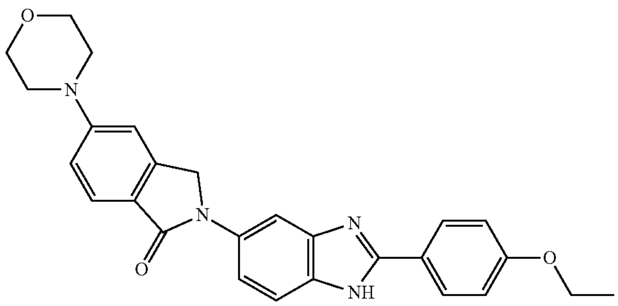 [SMILES: CCOc1ccc(-c2nc3cc(N4Cc5cc(N6CCOCC6)ccc5C4=O)ccc3[nH]2)cc1] | | 455.1 |

TABLE 1-25

| Ex.No. | IUPAC NAME | Structure | ADDITIVE | MS |
|---|---|---|---|---|
| 73 | 5-(morpholin-4-yl)-2-(2-phenyl-1H-benzimidazol-5-yl)isoindolin-1-one | 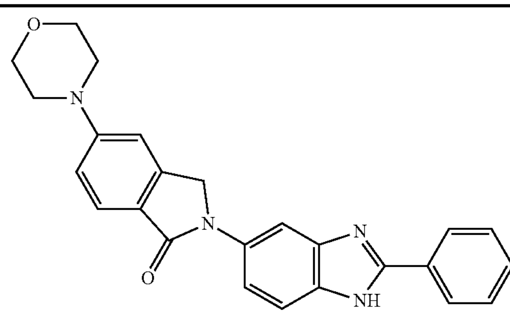 | | 411.2 |

Experimental Example 1

For detection of cardiomyocyte maturation, double knock-in human iPS cell lines, in which reporter protein sequences, EmGFP (Sequence Number 1) and mCherry (Sequence Number 2) were inserted into gene loci for TNNI1 and TNNI3, respectively, were prepared (the human iPS cells were prepared from episomal vector (loaded gene; OCT3/4, KLF4, SOX2, L-MYC, LIN28, mouse p53DD) using PBMC (LP_167, Sample ID: 20130318) purchased from CTL (reference literature; Okita K, et al. Stem Cells. 2012 Nov. 29. doi: 10.1002/stem.1293)).

The maintenance culture of the above-mentioned reporter iPS cell lines was carried out by a conventional method (Okita K, et al. Stem Cells. 2012 Nov. 29. doi: 10.1002/stem.1293).

For differentiation induction into cardiomyocytes, the reporter iPS cell lines were treated with 0.5×TrypLE select (Life Technologies, diluted in 1/2 with 0.5 mM EDTA/PBS) for 4 to 5 minutes, and the cells were exfoliated using a cell scraper (IWAKI), and then dissociated into the single cell by pipetting. The medium was removed by centrifugation (1,000 rpm, 5 min), and the obtained cells were seeded on a bioreactor (ABLE) by $1 \times 10^7$ cells per 30 mL of the bioreactor, and then cultured in a medium prepared by adding 1% L-glutamine, transferrin 150 μg/mL, ascorbic acid 50 μg/mL (Sigma), monothioglycerol 4×10$^{-4}$ M, 10 μM Rock inhibitor (Y-27632), 2 ng/mL BMP4 (R&D) and 0.5% Matrigel (Growth Factor Reduced) to a medium after removal of solution C from StemFit AK02 (AJINOMOTO AK02, 400 mL of solution A and 100 mL of B solution, total 500 mL), at 37° C., under 5% oxygen condition (55 rpm, stirred suspension culture method) to form embryoid bodies (0 day).

Next day (1st day), 9 μL (final concentration 3 ng/mL) of 10 μg/mL activin A, 15 μL (final concentration 5 ng/mL) of 10 μg/mL bFGF and 24 μL (final concentration 10 ng/mL) of 10 μg/mL BMP4 were added to the bioreactor, and the cells were cultured at 37° C. for additional 2 days, under 5% oxygen condition.

Then (3rd day), the obtained embryoid bodies were collected in a 50 mL centrifuge tube, and then subjected to centrifugation (200 g, 1 min). The medium was removed, and the embryoid bodies were cultured in a medium prepared by adding 1% L-glutamine, transferrin 150 μg/mL, ascorbic acid 50 μg/mL (Sigma), monothioglycerol 4×10$^{-4}$ M, 10 ng/mL VEGF, 1 μM IWP-3, 0.6 μM dorsomorphin and 5.4 μM SB431542 to a medium after removal of solution C from StemFit AK02 (AJINOMOTO AK02, 400 mL of solution A and 100 mL of B solution, total 500 mL), at 37° C. for 3 days, under 5% oxygen condition (55 rpm, stirred suspension culture method).

Then (6th day), the bioreactor was left to stand to precipitate the embryoid bodies, and 80 to 90% of the medium was removed. A medium prepared by adding 1% L-glutamine, transferrin 150 μg/mL, ascorbic acid 50 μg/mL (Sigma), monothioglycerol 4×10$^4$ M and 5 ng/mL VEGF to a medium after removal of solution C from StemFit AK02 (AJINOMOTO AK02, 400 mL of solution A and 100 mL of B solution, total 500 mL) was added to the bioreactor so that the total volume became 30 mL, and the embryoid bodies were cultured for 8 days, at 37° C., under 5% oxygen condition (55 rpm, stirred suspension culture method). During the culture, the medium was replaced with a medium under the same conditions every 2 to 3 days.

14th Day after the start of the differentiation induction, the embryoid bodies were treated with 2 mg/mL collagenase type I (Sigma) for 2 hr, and then with 0.25% trypsin/EDTA (Invitrogen) for 10 min. 50% FBS/IMDM (Thermo Fisher Science) was added thereto, and the embryoid bodies were dissociated into the single cell by pipetting, and then subjected to centrifugation (1,000 rpm, 5 minutes). After the centrifugation, the supernatant was removed, and the cells were re-suspended in a 100 mL of StemFit AK02 medium-based AK02 medium for cardiomyocyte differentiation (prepared by adding ascorbic acid 50 μg/mL, L-glutamine 2 mM, transferrin 150 mg/mL, monothioglycerol 4×10$^{-4}$ M and VEGF 5 ng/ml to AJINOMOTO AK02 (400 mL of solution A and 100 mL of B solution, total 500 mL)). The re-suspended cells were seeded on CellCarrier-384 Ultra Microplate (Perkin Elmer/6057300) pre-coated with iMatrix-511 (purchased from Nippi, Inc.) by 1.0×10$^4$ cells/well, and cultured in StemFit AK02 medium-based AK02 medium for cardiomyocyte differentiation (prepared by adding ascorbic acid 50 μg/mL, L-glutamine 2 mM, transferrin 150 mg/mL and monothioglycerol 4×10$^{-4}$ M to AJINOMOTO AK02 (400 mL of solution A and 100 mL of B solution, total 500 mL) by 70 μL/well).

The test compound (1 or 30 μM, one compound per well) was added to the wells by 50 μL/well on 3rd and 6th culture days. On 8th culture day, the cells were fixed with paraformaldehyde (Wako Pure Chemical Corporation, 163-20145), and subjecting to immunostaining using rat anti-mCherry (Invitrogen, M11217) as a primary antibody and goat anti-rat IgG Alexa 647 (Invitrogen, A-21247) as a secondary antibody. The expression level of Alexa 647 was measured by HCS (high contents screening) system (Perkin Elmer/OperaPhenix High Contents Imaging System) (shooting mode; non-confocal, objective lens; 10×air NA0.3).

The average fluorescent intensity (average of n=60) of control well (no addition of the test compound) was 797, calculated from the measured fluorescent intensities. The results are shown in Table 2 (average of n=3 (Example 1 to 7, 9 to 59, 61 to 71) or n=6 (Example 8, 60, 72 and 73)). The symbol in Table 2 means that the average fluorescent intensity cannot be evaluated due to cell decrease.

TABLE 2

| Example No. | average fluorescent intensity (at 1 μM) | average fluorescent intensity (at 30 μM) |
|---|---|---|
| 1 | 1098 | — |
| 2 | 943 | 1073 |
| 3 | 933 | 1441 |
| 4 | 1621 | 894 |
| 5 | 1078 | — |
| 6 | 974 | 987 |
| 7 | 859 | 1631 |
| 8 | 985 | — |
| 9 | 948 | — |
| 10 | 1032 | — |
| 11 | 1182 | — |
| 12 | 1675 | 1226 |
| 13 | 1212 | — |
| 14 | 2143 | 2012 |
| 15 | 1701 | 2697 |
| 16 | 1366 | 3604 |
| 17 | 1544 | 1079 |
| 18 | 1272 | 1704 |
| 19 | 1292 | 860 |
| 20 | 1685 | |
| 21 | 1120 | — |
| 22 | 1211 | — |
| 23 | 1386 | |
| 24 | 1241 | — |
| 25 | 1260 | 900 |
| 26 | 1809 | — |
| 27 | 1821 | |
| 28 | 1540 | — |
| 29 | 1120 | 910 |
| 30 | 1005 | 876 |
| 31 | 736 | 888 |
| 32 | 1312 | 1937 |
| 33 | 1568 | 3010 |
| 34 | 1540 | — |
| 35 | 1536 | 1204 |
| 36 | 1006 | 1743 |
| 37 | 1696 | 1290 |
| 38 | 1633 | — |
| 39 | 1042 | 1026 |
| 40 | 1089 | 1327 |
| 41 | 1107 | 1571 |
| 42 | 980 | 1041 |
| 43 | 1087 | 1153 |
| 44 | 1071 | 1141 |
| 45 | 1130 | 814 |
| 46 | 1142 | 1616 |
| 47 | 1115 | 1348 |
| 48 | 1182 | 1408 |
| 49 | 1382 | 890 |
| 50 | 1126 | 1717 |
| 51 | 963 | 1279 |
| 52 | 937 | 973 |
| 53 | 880 | 2812 |
| 54 | 838 | — |
| 55 | 1092 | |
| 56 | 1185 | 897 |
| 57 | 778 | 1666 |
| 58 | 994 | 819 |
| 59 | 803 | 1301 |

TABLE 2-continued

| Example No. | average fluorescent intensity (at 1 µM) | average fluorescent intensity (at 30 µM) |
|---|---|---|
| 60 | 770 | 868 |
| 61 | 1150 | — |
| 62 | 1004 | — |
| 63 | 1194 | — |
| 64 | 1328 | — |
| 65 | 1245 | 836 |
| 66 | 1338 | 1358 |
| 67 | 1367 | 1188 |
| 68 | 1301 | — |
| 69 | 1222 | 1942 |
| 70 | 998 | 4335 |
| 71 | 923 | — |
| 72 | 1370 | 948 |
| 73 | 1231 | 922 |

Experimental Example 2

For detection of cardiomyocyte maturation, double knock-in human iPS cell lines, in which reporter protein sequences, EmGFP (Sequence Number 1) and mCherry (Sequence Number 2) were inserted into gene loci for TNNI1 and TNNI3, respectively, were prepared (the human iPS cells were prepared from episomal vector (loaded gene; OCT3/4, KLF4, SOX2, L-MYC, LIN28, mouse p53DD) using PBMC (LP_167, Sample ID: 20130318) purchased from CTL (reference literature; Okita K, et al. Stem Cells. 2012 Nov. 29. doi: 10.1002/stem.1293)).

The maintenance culture of the above-mentioned reporter iPS cell lines was carried out by a conventional method (Okita K, et al. Stem Cells. 2012 Nov. 29. doi: 10.1002/stem.1293).

For differentiation induction into cardiomyocytes, the reporter iPS cell lines were treated with 0.5×TrypLE select (Life Technologies, diluted in 1/2 with 0.5 mM EDTA/PBS) for 4 to 5 minutes, and the cells were exfoliated using a cell scraper (IWAKI), and then dissociated into the single cell by pipetting. The medium was removed by centrifugation (1,000 rpm, 5 min), and the obtained cells were suspended in a medium prepared by adding 1% L-glutamine, transferrin 150 µg/mL, ascorbic acid 50 µg/mL (Sigma), monothioglycerol $4 \times 10^{4}$ M, 10 µM Rock inhibitor (Y-27632), 2 ng/mL BMP4 (R&D) and 0.5% Matrigel (Growth Factor Reduced) to StemPro-34 SFM (ThermoFisher) in a 6 well-plate by $2 \times 10^6$ cells/1.5 mL/well, and then subjected to static culture at 37° C., under 5% oxygen condition to form embryoid bodies (0 day).

Next day (1st day), a medium prepared by adding 1% L-glutamine, transferrin 150 µg/mL, ascorbic acid 50 µg/mL (Sigma), monothioglycerol $4 \times 10^{-4}$ M, 1.8 µL (concentration 12 ng/mL) of 10 µg/mL activin A, 15 µL (concentration 10 ng/mL) of 10 µg/mL bFGF and 2.7 µL (concentration 18 ng/mL) of 10 µg/mL BMP4 to 1.5 mL of StemPro-34 SFM (ThermoFisher) was added to each well of the 6 well plate containing the embryoid bodies to adjust the volume combined with the 0 day's medium to final 3 mL (activin A: 6 ng/ml, bFGF: 5 ng/ml, BMP4: 10 ng/ml), and the embryoid bodies were cultured at 37° C. for additional 2 days, under 5% oxygen condition.

Then (3rd day), the 6 well plate containing the embryoid bodies was inclined, and then left to stand for 1 to 2 minutes until the embryoid bodies were precipitated at the edges of the wells, and the supernatant was aspirated so as not to suck the embryoid bodies. Then, IMDM (ThermoFisher) medium was added to each well, and, as above, the plate was inclined, and then left to stand for 1 to 2 minutes, and the supernatant was aspirated so as not to suck the embryoid bodies. A medium prepared by adding 1% L-glutamine, transferrin 150 µg/mL, ascorbic acid 50 µg/mL (Sigma), monothioglycerol $4 \times 10^{-4}$ M, 10 ng/mL VEGF, 1 µM IWP-3, 0.6 µM dorsomorphin and 5.4 µM SB431542 to 3 mL of StemPro-34 SFM (ThermoFisher) was added to each well of the 6 well plate, and then the embryoid bodies were cultured at 37° C. for 3 days, under 5% oxygen condition.

Then (6th day), the 6 well plate containing the embryoid bodies was inclined, and then left to stand for 1 to 2 minutes until the embryoid bodies were precipitated at the edges of the wells, and the supernatant was aspirated so as not to suck the embryoid bodies. A medium prepared by adding 1% L-glutamine, transferrin 150 µg/mL, ascorbic acid 50 µg/mL (Sigma), monothioglycerol $4 \times 10^{-4}$ M and 5 ng/mL VEGF to 2 mL of StemPro-34 SFM (ThermoFisher) was added to each well of the 6 well plate, and then the embryoid bodies were cultured at 37° C. for 2 days, under 5% oxygen condition.

Then (8th day), the 6 well plate containing the embryoid bodies was inclined, and then left to stand for 1 to 2 minutes until the embryoid bodies were precipitated at the edges of the wells, and the supernatant was aspirated so as not to suck the embryoid bodies. A medium prepared by adding (1) 1% L-glutamine, transferrin 150 µg/mL, ascorbic acid 50 µg/mL (Sigma), monothioglycerol $4 \times 10^{-4}$ M and 5 ng/mL VEGF, and (2) the test compound (each 3 µM) shown in Table 3 or DMSO (0.1% addition relative to the medium volume) to 2 mL of StemPro-34 SFM (ThermoFisher) was added to each well of the 6 well plate, and then the embryoid bodies were cultured at 37° C. for 2 days, under 5% oxygen condition.

Then (10th day), the 6 well plate containing the embryoid bodies was inclined, and then left to stand for 1 to 2 minutes until the embryoid bodies were precipitated at the edges of the wells, and the supernatant was aspirated so as not to suck the embryoid bodies. A medium prepared by adding (1) 1% L-glutamine, transferrin 150 µg/mL, ascorbic acid 50 µg/mL (Sigma), monothioglycerol $4 \times 10^{-4}$ M and 5 ng/mL VEGF, and (2) the test compound (each 3 µM) shown in Table 3 or DMSO (0.1% addition relative to the medium volume) to 3 mL of StemPro-34 SFM (ThermoFisher) was added to each well of the 6 well plate, and then the embryoid bodies were cultured at 37° C. for 6 days, under general oxygen condition. On 13th day, the medium was replaced with a medium under the same conditions.

On the 16th day, after the embryoid bodies under each condition were photographed by fluorescence microscope, the 6 well plate containing the embryoid bodies was inclined, and then left to stand for 1 to 2 minutes until the embryoid bodies were precipitated at the edges of the wells, and the supernatant was aspirated so as not to suck the embryoid bodies. Then, 2 mL of PBS was added to each well, and, as above, the plate was inclined, and then left to stand for 1 to 2 minutes, and the PBS was aspirated so as not to suck the embryoid bodies. A solution prepared by adding DNase 10 µg/mL and Liberase 100 µg/mL to 3 mL of IMDM was added to each well, and the plate was left to stand at 37° C. for 1 hr, under general oxygen condition. After 1 hr, the plate was inclined, and then left to stand for 1 to 2 minutes until the embryoid bodies were precipitated at the edges of the wells, and the supernatant was aspirated so as not to suck the embryoid bodies. Then, 2 mL of PBS was added to each well, and, as above, the plate was inclined, and then left to stand for 1 to 2 minutes, and the PBS was aspirated so as not to suck the embryoid bodies. A solution prepared by adding DNase 10 µg/mL to 2 mL of TrypLE select was added to each well, and the plate was left to stand at 37° C. for 10 minutes, under general oxygen condition. Then, a medium prepared by adding 1% L-glutamine, transferrin 150 µg/mL, ascorbic acid 50 µg/mL (Sigma), monothioglycerol $4\times10^{-4}$ M, 5 ng/mL VEGF and DNase 10 µg/mL to 2 mL of StemPro-34 SFM (ThermoFisher) was added to each well, and the embryoid bodies were dissociated into the single cell by pipetting, and then subjected to centrifugation (1,000 rpm, 5 minutes). After the centrifugation, the supernatant was removed, the cells were suspended in 1 to 2 mL of 2% FBS/PBS, and the mCherry expression in TNNI1+ cells was analyzed by flow cytometry (BD FACSAria Fusion cell sorter). The results are shown in Table 3 and FIGS. 1 to 7.

TABLE 3

|  | mCherry+ (%) |
|---|---|
| control (addition of (1) alone) | 7.1 |
| control (0.1% DMSO addition relative to the medium volume) | 7.8 |
| Example 8 3 µM | 61.0 |
| Example 46 3 µM | 47.2 |
| Example 45 3 µM | 66.6 |
| Example 4 3 µM | 58.1 |
| Example 17 3 µM | 42.1 |

Experimental Example 3

For detection of cardiomyocyte maturation, double knock-in human iPS cell lines, in which reporter protein sequences, EmGFP (Sequence Number 1) and mCherry (Sequence Number 2) were inserted into gene loci for TNNI1 and TNNI3, respectively, were prepared (the human iPS cells were prepared from episomal vector (loaded gene; OCT3/4, KLF4, SOX2, L-MYC, LIN28, mouse p53DD) using PBMC (LP_167, Sample ID: 20130318) purchased from CTL (reference literature; Okita K, et al. Stem Cells. 2012 Nov. 29. doi: 10.1002/stem.1293)).

The maintenance culture of the above-mentioned reporter iPS cell lines was carried out by a conventional method (Okita K, et al. Stem Cells. 2012 Nov. 29. doi: 10.1002/stem.1293).

For differentiation induction into cardiomyocytes, the reporter iPS cell lines were treated with 0.5×TrypLE select (Life Technologies, diluted in 1/2 with 0.5 mM EDTA/PBS) for 4 to 5 minutes, and the cells were exfoliated using a cell scraper (IWAKI), and then dissociated into the single cell by pipetting. The medium was removed by centrifugation (1,000 rpm, 5 min), and the obtained cells were suspended in a medium prepared by adding 1% L-glutamine, transferrin 150 µg/mL, ascorbic acid 50 µg/mL (Sigma), monothioglycerol $4\times10^{-4}$ M, 10 µM Rock inhibitor (Y-27632), 2 ng/mL BMP4 (R&D) and 0.5% Matrigel (Growth Factor Reduced) to StemPro-34 SFM (ThermoFisher) in a 6 well-plate by $2\times10^6$ cells/1.5 mL/well, ID and then subjected to static culture at 37° C., under 5% oxygen condition to form embryoid bodies (0 day).

Next day (1st day), a medium prepared by adding 1% L-glutamine, transferrin 150 µg/mL, ascorbic acid 50 µg/mL (Sigma), monothioglycerol $4\times10^{-4}$ M, 1.8 µL (concentration 12 ng/mL) of 10 µg/mL activin A, 15 µL (concentration 10 ng/mL) of 10 µg/mL bFGF and 2.7 µL (concentration 18 ng/mL) of 10 µg/mL BMP4 to 1.5 mL of StemPro-34 SFM (ThermoFisher) was added to each well of the 6 well plate containing the embryoid bodies to adjust the volume combined with the 0 day's medium to final 3 mL (activin A: 6 ng/ml, bFGF: 5 ng/ml, BMP4: 10 ng/ml), and the embryoid bodies were cultured at 37° C. for additional 2 days, under 5% oxygen condition.

Then (3rd day), the 6 well plate containing the embryoid bodies was inclined, and then left to stand for 1 to 2 minutes until the embryoid bodies were precipitated at the edges of the wells, and the supernatant was aspirated so as not to suck the embryoid bodies. Then, IMDM (ThermoFisher) medium was added to each well, and, as above, the plate was inclined, and then left to stand for 1 to 2 minutes, and the supernatant was aspirated so as not to suck the embryoid bodies. A medium prepared by adding 1% L-glutamine, transferrin 150 µg/mL, ascorbic acid 50 µg/mL (Sigma), monothioglycerol $4\times10^{-4}$ M, 10 ng/mL VEGF, 1 µM IWP-3, 0.6 µM dorsomorphin and 5.4 µM SB431542 to 3 mL of StemPro-34 SFM (ThermoFisher) was added to each well of the 6 well plate, and then the embryoid bodies were cultured at 37° C. for 3 days, under 5% oxygen condition.

Then (6th day), the 6 well plate containing the embryoid bodies was inclined, and then left to stand for 1 to 2 minutes until the embryoid bodies were precipitated at the edges of the wells, and the supernatant was aspirated so as not to suck the embryoid bodies. A medium prepared by adding 1% L-glutamine, transferrin 150 µg/mL, ascorbic acid 50 µg/mL (Sigma), monothioglycerol $4\times10^{-4}$ M and 5 ng/mL VEGF to 2 mL of StemPro-34 SFM (ThermoFisher) was added to each well of the 6 well plate, and then the embryoid bodies were cultured at 37° C. for 2 days, under 5% oxygen condition.

Then (8th day), the 6 well plate containing the embryoid bodies was inclined, and then left to stand for 1 to 2 minutes until the embryoid bodies were precipitated at the edges of the wells, and the supernatant was aspirated so as not to suck the embryoid bodies. A medium prepared by adding (1) 1% L-glutamine, transferrin 150 µg/mL, ascorbic acid 50 µg/mL (Sigma), monothioglycerol $4\times10^{-4}$ M and 5 ng/mL VEGF, and (2) the compound of Example 8 (3 µM) or DMSO (0.1% addition relative to the medium volume) to 2 mL of StemPro-34 SFM (ThermoFisher) was added to each well of the 6 well plate, and then the embryoid bodies were cultured at 37° C. for 2 days, under 5% oxygen condition.

On the 10th day, the medium was replaced with a medium prepared by adding (1) 1% L-glutamine, transferrin 150 µg/mL, ascorbic acid 50 µg/mL (Sigma), monothioglycerol $4\times10^{-4}$ M and 5 ng/mL VEGF, and (2) Compound A (40 nM, the structure is shown below), or a mixture of the compound of Example 8 (3 µM) and Compound A (40 nM), or DMSO (0.1% addition relative to the medium volume) to 2 mL of StemPro-34 SFM (ThermoFisher), and then the embryoid bodies were cultured at 37° C. for 6 days, under general oxygen condition. On 13th day, the medium was replaced with a medium under the same conditions.

Figure 8:
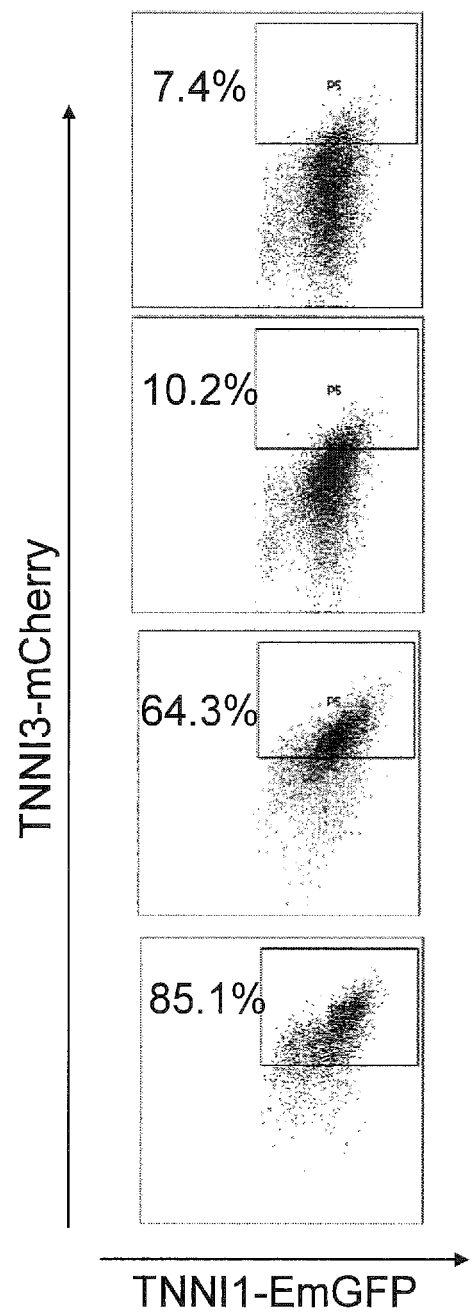
FIG. 8 shows the results of mCherry expression analysis by flow cytometry in Experimental Example 3. The figures show the results in cases of control (no addition), control (DMSO addition), addition of compound of Example 8 and compound A (Example 8: 8-9 days, compound A: 10-15 days), and addition of compound of Example 8 and compound A (Example 8: 8-15 days, compound A: 10-15 days), in order from the top.

On the 16th day, after the embryoid bodies under each condition were photographed by fluorescence microscope, the 6 well plate containing the embryoid bodies was inclined, and then left to stand for 1 to 2 minutes until the embryoid bodies were precipitated at the edges of the wells, and the supernatant was aspirated so as not to suck the embryoid bodies. Then, 2 mL of PBS was added to each well, and, as above, the plate was inclined, and then left to stand for 1 to 2 minutes, and the PBS was aspirated so as not to suck the embryoid bodies. A solution prepared by adding DNase 10 µg/mL and Liberase 100 µg/mL to 3 ml of IMDM was added to each well, and the plate was left to stand at 37° C. for 1 hr, under general oxygen condition. After 1 hr, the plate was inclined, and then left to stand for 1 to 2 minutes until the embryoid bodies were precipitated at the edges of the wells, and the supernatant was aspirated so as not to suck the embryoid bodies. Then, 2 mL of PBS was added to each well, and, as above, the plate was inclined, and then left to stand for 1 to 2 minutes, and the PBS was aspirated so as not to suck the embryoid bodies. A solution prepared by adding DNase 10 μg/mL to 2 mL of TrypLE select was added to each well, and the plate was left to stand at 37° C. for 10 minutes, under general oxygen condition. Then, a medium prepared by adding 1% L-glutamine, transferrin 150 μg/mL, ascorbic acid 50 μg/mL (Sigma), monothioglycerol $4 \times 10^{-4}$ M, 5 ng/mL VEGF and DNase 10 μg/mL to 2 mL of StemPro-34 SFM (ThermoFisher) was added to each well, and the embryoid bodies were dissociated into the single cell by pipetting, and then subjected to centrifugation (1,000 rpm, 5 minutes). After the centrifugation, the supernatant was removed, the cells were suspended in 1 to 2 mL of 2% FBS/PBS, and the mCherry expression in TNNI1$^+$ cells was analyzed by flow cytometry (BD FACSAria Fusion cell sorter). The results are shown in Table 4 and FIG. 8.

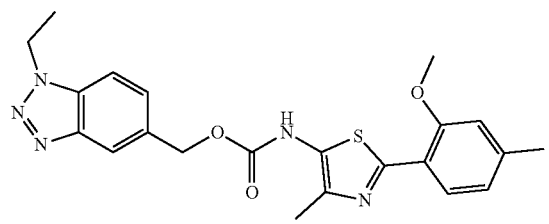 [SMILES: CCn1nnc2cc(COC(=O)Nc3sc(-c4ccc(C)cc4OC)nc3C)ccc21]

TABLE 4

|  | mCherry$^+$ (%) |
| --- | --- |
| control (addition of (1) alone) | 7.4 |
| control (0.1% DMSO addition relative to the medium volume) (8-15th days) | 10.2 |
| Example 8 (3 μM, 8-9th days) compound A (40 nM, 10-15th days) | 64.3 |
| Example 8 (3 μM, 8-9 days) Example 8 (3 μM) + Compound A (40 nM) (10-15th days) | 85.1 |

Experimental Example 4

For analysis of electrophysiological function of cardiomyocytes, humans iPS cell lines 409B2 (prepared from episomal vector (pCXLE-hOCT3/4-shp53-F, pCXLE-hSK, pCXLE-hUL) using HDF1388 purchased from Cell Applications, Inc (reference literature; Okita et al., Nat Methods. 8(5):409-12. (2011))) were used.

The maintenance culture of the above-mentioned iPS cell lines was carried out by a conventional method (Takahashi K, et al. Cell. 131: 861-72, 2007 and Nakagawa M, et al. Nat Biotechnol. 26: 101-6, 2008).

For differentiation induction into cardiomyocytes, the iPS cell lines were treated with CTK solution (ReproCELL) for 2 minutes, the solution was removed, and then the iPS cell lines were treated with Accumax (Innovative Cell Technologies) for 5 minutes, and the cells were dissociated into the single cell by pipetting. The cells were collected by centrifugation (1,000 rpm, 5 min), and seeded on low attachment 96 well dish (Corning) by 5000 cells/70 μL/well, and cultured in a medium prepared by adding 1% L-glutamine, transferrin 150 μg/mL, ascorbic acid 50 μg/mL (Sigma), monothioglycerol $4 \times 10^{-4}$ M, 10 μM Rock inhibitor (Y-27632), 2 ng/mL BMP4 (R&D) and 0.5% Matrigel (Growth Factor Reduced) to StemPro-34 SFM (ThermoFisher) at 37° C., under 5% oxygen condition to form embryoid bodies (0 day).

Next day (1st day), a medium (70 μL) prepared by adding 1% L-glutamine, transferrin 150 μg/mL, ascorbic acid 50 μg/mL (Sigma), monothioglycerol $4 \times 10^{-4}$ M, 12 ng/mL activin A, 10 ng/mL bFGF and 18 ng/mL BMP4 to StemPro-34 SFM (ThermoFisher) was added to each well of the 96 well plate containing the embryoid bodies to adjust the volume combined with the 0 day's medium to final 140 μL, and the embryoid bodies were cultured at 37° C. for additional 2 days, under 5% oxygen condition.

Then (3rd day), the obtained embryoid bodies were collected, the medium was removed by centrifugation (1,000 rpm, 3 min), and Accumax (innovative cell technologies) was added thereto. After 5 minutes, the embryoid bodies were dissociated into the single cell by pipetting, IMDM (5 ml, invitrogen) was added thereto, and the medium was removed by centrifugation (1,000 rpm, 5 min). The cells were seeded on low attachment 96 well plate (Corning) by 10000 cells/100 μL/well, and cultured in a medium prepared by adding 1% L-glutamine, transferrin 150 μg/mL, ascorbic acid 50 μg/mL (Sigma), monothioglycerol $4 \times 10^{-4}$ M, 10 ng/mL VEGF and 1 μM IWP-3 to StemPro-34 SFM (ThermoFisher) at 37° C. for 3 days, under 5% oxygen condition.

Then (6th day), the obtained embryoid bodies were collected, and put in a low attachment 6 well plate so as not to exceed 60 EB per well. The 6 well plate containing the embryoid bodies was inclined, and then left to stand for 1 to 2 minutes until the embryoid bodies were precipitated at the edges of the wells, and the supernatant was aspirated so as not to suck the embryoid bodies. A medium prepared by adding 1% L-glutamine, transferrin 150 μg/mL, ascorbic acid 50 μg/mL (Sigma), monothioglycerol $4 \times 10^{-4}$ M and 5 ng/mL VEGF to 2 mL of StemPro-34 SFM (ThermoFisher) was added to each well of the 6 well plate, and then the embryoid bodies were cultured at 37° C. for 4 days, under 5% oxygen condition. On 8th day, the medium was replaced with a medium under the same conditions.

Then (10th day), the 6 well plate containing the embryoid bodies was inclined, and then left to stand for 1 to 2 minutes until the embryoid bodies were precipitated at the edges of the wells, and the supernatant was aspirated so as not to suck the embryoid bodies. A medium prepared by adding 1% L-glutamine, transferrin 150 μg/mL, ascorbic acid 50 μg/mL (Sigma), monothioglycerol $4 \times 10^{-4}$ M and 5 ng/mL VEGF to 2 mL of StemPro-34 SFM (ThermoFisher) was added to each well of the 6 well plate, and then the embryoid bodies were cultured at 37° C. for 10 days, under general oxygen condition. During the culture, the medium was replaced with a medium under the same conditions every 2 to 3 days.

Then (20th day), the 6 well plate containing the embryoid bodies was inclined, and then left to stand for 1 to 2 minutes until the embryoid bodies were precipitated at the edges of the wells, and the supernatant was aspirated so as not to suck the embryoid bodies. Then, 2 mL of PBS was added to each well, and, as above, the plate was inclined, and then left to stand for 1 to 2 minutes, and the PBS was aspirated so as not to suck the embryoid bodies. A solution prepared by adding DNase 10 μg/mL and Liberase 100 μg/mL to 3 mL of IMDM was added to each well, and then the embryoid bodies were left to stand at 37° C. for 1 hr, under general oxygen condition. After 1 hr, the plate was inclined, and then left to stand for 1 to 2 minutes until the embryoid bodies were precipitated at the edges of the wells, and the supernatant was aspirated so as not to suck the embryoid bodies. Then, 2 mL of PBS was added to each well, and, as above, the plate was inclined, and then left to stand for 1 to 2 minutes, and the PBS was aspirated so as not to suck the embryoid bodies. A solution prepared by adding DNase 10 μg/mL to 2 mL of TrypLE select was added to each well, and then the embryoid bodies were left to stand at 37° C. for 10 minutes, under general oxygen condition. Then, a medium prepared by adding 1% L-glutamine, transferrin 150 μg/mL, ascorbic acid 50 μg/mL (Sigma), monothioglycerol $4 \times 10^{-4}$ M, 5 ng/mL VEGF and DNase 10 μg/mL to 2 mL of StemPro-34 SFM (ThermoFisher) was added to each well, and the embryoid bodies were dissociated into the single cell by pipetting. The cells were subjected to centrifugation (1,000 rpm, 5 min). After the centrifugation, the supernatant was removed, and the cells were suspended in 1 to 2 mL of 2% FBS/PBS, and stained with SIRPa and Lineage (CD31, CD49a, CD90, CD140b) antibody, and the SIRPa$^+$Lin$^-$cell group was collected by flow cytometry (BD FACSAria Fusion cell sorter) (see, Dubois N C, et al. Nat Biotechnol. 29: 1011-8, 2011). The collected cells were subjected to centrifugation (1,000 rpm, 5 min), suspended in a medium prepared by adding 1% L-glutamine, transferrin 150 μg/mL, ascorbic acid 50 μg/mL (Sigma), monothioglycerol $4 \times 10^{-4}$ M and 5 ng/mL VEGF to StemPro-34 SFM (ThermoFisher), and seeded on a glass bottom dish pre-coated with fibronectin by $5 \times 10^4$ cells/5 μL, and the dish was left to stand for 2 to 3 hr at 37° C., under general oxygen condition. Then, a medium prepared by adding 1% L-glutamine, transferrin 150 μg/mL, ascorbic acid 50 μg/mL (Sigma), monothioglycerol $4 \times 10^{-4}$ M and 5 ng/mL VEGF to 2 mL of StemPro-34 SFM (ThermoFisher) was added to the dish, and the cells were cultured at 37° C. for 5 days, under general oxygen condition. During the culture, the medium was replaced with a medium under the same conditions every 2 to 3 days.

On 25th day, the medium was removed from the dish, and replaced with a medium containing the test compound I (the compound of Example 8, 30 μM), the test compound II (a mixture of the compound of Example 8 (30 μM) and Compound A (40 nM)) or DMSO (final concentration 0.1%) as a control (the medium was prepared by adding 1% L-glutamine, transferrin 150 μg/mL, ascorbic acid 50 μg/mL (Sigma), monothioglycerol $4 \times 10^{-4}$ M and 5 ng/mL VEGF to StemPro-34 SFM (ThermoFisher)). The cells were cultured at 37° C. for 4 days, under general oxygen condition, and, on 28th day, the cells were subjected to membrane potential analysis.

The medium was removed from the dish containing the cells on 28th day, and a solution prepared by adding 0.2 μL of FluoVolt™ membrane potential dye (Invitrogen, F10488) to 200 μL of gay balanced salt solution (Sigma) was added dropwise to the glass part of the dish, and the cells were incubated at 37° C. for 15 min, under general oxygen condition. After the incubation, the solution containing the membrane potential dye was removed, 1 mL of gay balanced salt solution was added to the dish, and the cells were incubated in an incubator on a microscope stage (37° C., general oxygen) for 1 hr. After the incubation, the cells were subjected to a fluorescence reaction for 30 seconds every 5.9 millisecond with excitation light of 490 nm using AquaCosmos 2.6 (Hamamatsu Photonics K.K). The measurement range (ROI) was set to 512×64 pixels, and three ROIs were measured per dish. The results are shown in Table 5.

TABLE 5 beats per minute (each group n = 3, mean ± standard deviation)

|  | control | compound I | compound II |
|---|---|---|---|
| beats (mean) | 70.7 | 32.0 | 38.0 |
| standard deviation | 2.3 | 0 | 2 |

INDUSTRIAL APPLICABILITY

Since compound (I) has an activity to promote the maturation of a cardiomyocyte, it is useful as a cardiomyocyte maturation promoter.

This application is based on patent application No. 2018-69872 filed on Mar. 30, 2018 in Japan, the contents of which are encompassed in full herein.

The invention claimed is:

1. A compound represented by the formula (I):

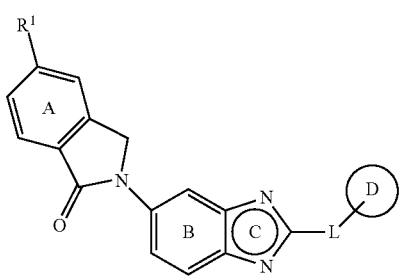

wherein
Ring A is a benzene ring;
Ring B is a benzene ring;
Ring C is an imidazole ring optionally further substituted by $C_{1-6}$ alkyl group(s);
L is a bond or a methylene group;
$R^1$ is
(1) a hydrogen atom,
(2) a halogen atom,
(3) a mono- or di-$C_{1-6}$ alkylamino group,
(4) a 5- to 14-membered aromatic heterocyclic group, or
(5) a 3- to 14-membered non-aromatic heterocyclic group optionally substituted by 1 to 3 $C_{1-6}$ alkyl groups; and Ring D is
(1) a benzene ring optionally further substituted by 1 to 3 substituents selected from
(a) a halogen atom,
(b) a hydroxy group,
(c) a $C_{1-6}$ alkyl group optionally substituted by 1 to 3 $C_{1-6}$ alkoxy groups,
(d) a $C_{1-6}$ alkoxy group optionally substituted by 1 to 3 substituents selected from
(i) a carboxy group,
(ii) a $C_{1-6}$ alkoxy-carbonyl group,
(iii) a $C_{7-16}$ aralkyloxy-carbonyl group,
(iv) a carbamoyl group optionally mono- or di-substituted by substituent(s) selected from
(I) $C_{1-6}$ alkyl group optionally substituted by 1 to 3 substituents selected from
(A) a $C_{3-10}$ cycloalkyl group,
(B) a $C_{6-14}$ aryl group,
(C) a $C_{6-14}$ arylamino group optionally substituted by 1 to 3 halogen atoms,
(D) a 5- to 14-membered aromatic heterocyclic group,
(E) a 3- to 14-membered non-aromatic heterocyclic group, and
(F) a carbamoyl group optionally mono- or di-substituted by substituent(s) selected from a $C_{1-6}$ alkyl group and a $C_{7-16}$ aralkyl group,
(II) a $C_{2-6}$ alkenyl group optionally substituted by 1 to 3 $C_{6-14}$ aryl groups, (III) a $C_{3-10}$ cycloalkyl group optionally substituted by 1 to 3 $C_{1-6}$ alkyl groups,
(IV) a $C_{6-14}$ aryl group optionally substituted by 1 to 3 substituents selected from
(A) a halogen atom, and
(B) a $C_{1-6}$ alkyl group,
(V) a $C_{7-16}$ aralkyl group,
(VI) a 5- to 14-membered aromatic heterocyclic group, and
(VII) a 3- to 14-membered non-aromatic heterocyclic group, and
(v) a 3- to 14-membered non-aromatic heterocyclylcarbonyl group optionally substituted by 1 to 3 substituents selected from
(I) a hydroxy group, and
(II) a $C_{1-6}$ alkyl group, and
(e) a $C_{7-16}$ aralkyloxy group,
(2) a cyclohexane ring,
(3) a pyridine ring,
(4) an isoxazole ring,
(5) a thiophene ring,
(6) a piperidine ring optionally further substituted by 1 to 3 $C_{1-6}$ alkoxy-carbonyl groups, or
(7) a tetrahydropyran ring,
or a salt thereof.

2. N-(1,1-Dioxido-2,3-dihydro-1-benzothiophen-5-yl)-2-(4-(5-(1-oxo-5-(piperidin-1-yl)-1,3-dihydro-2H-isoindol-2-yl)-1H-benzimidazol-2-yl)phenoxy)acetamide, or a salt thereof.

3. 2-(2-(4-Bromophenyl)-1H-benzimidazol-5-yl)-5-(morpholin-4-yl)isoindolin-1-one, or a salt thereof.

4. 5-(Piperidin-1-yl)-2-(2-(pyridin-3-yl)-1H-benzimidazol-5-yl)isoindolin-1-one, or a salt thereof.

5. 5-(Piperidin-1-yl)-2-(2-(pyridin-4-yl)-1H-benzimidazol-5-yl)isoindolin-1-one, or a salt thereof.

6. 2-(2-(4-Hydroxyphenyl)-1H-benzimidazol-5-yl)-5-(piperidin-1-yl)isoindolin-1-one, or a salt thereof.

7. A cardiomyocyte maturation promoter comprising the compound or salt according to claim 1.

8. A method for preparing a mature cardiomyocyte, which comprises a step of culturing an immature cardiomyocyte in the presence of the compound or salt according to claim 1.

9. A mature cardiomyocyte obtained by the method according to claim 8.

10. The compound or salt according to claim 1, wherein
Ring A is a benzene ring;
Ring B is a benzene ring;
Ring C is an imidazole ring;
L is a bond;
$R^1$ is a 3- to 8-membered monocyclic non-aromatic heterocyclic group; and
Ring D is
(1) a benzene ring optionally further substituted by 1 to 3 substituents selected from
(a) a halogen atom,
(b) a hydroxy group, and
(c) a $C_{1-6}$ alkoxy group optionally substituted by carbamoyl group(s) optionally mono- or di-substituted by 9- to 14-membered fused polycyclic non-aromatic heterocyclic group(s), or
(2) a pyridine ring.

11. The compound or salt according to claim 10, wherein $R^1$ is 5- to 6-membered non-aromatic heterocyclic group.

12. The compound or salt according to claim 10, wherein $R^1$ is 5- to 6-membered monocyclic non-aromatic cyclic amino group.

13. The compound or salt according to claim 1, wherein
Ring A is a benzene ring;
Ring B is a benzene ring;
Ring C is an imidazole ring;
L is a bond;
$R^1$ is a 3- to 8-membered monocyclic non-aromatic cyclic amino group; and
Ring D is a benzene ring further substituted by one substituent selected from
(a) a halogen atom and
(b) a $C_{1-6}$ alkoxy group substituted by carbamoyl group(s) mono-substituted by a 9- to 14-membered fused polycyclic non-aromatic heterocyclic group.

14. The compound or salt according to claim 13, wherein $R^1$ is 5- to 6-membered monocyclic non-aromatic cyclic amino group.

15. The compound or salt according to claim 13, wherein Ring D is a benzene ring further substituted by one $C_{1-6}$ alkoxy group substituted by carbamoyl group(s) mono-substituted by a 9- to 14-membered fused bicyclic or tricyclic non-aromatic heterocyclic group.

16. The compound or salt according to claim 13, wherein Ring D is a benzene ring further substituted by one methoxy group substituted by carbamoyl group(s) mono-substituted by a 9- to 14-membered fused bicyclic or tricyclic non-aromatic heterocyclic group.

17. The compound or salt according to claim 13, wherein Ring D is a benzene ring further substituted by one $C_{1-6}$ alkoxy group substituted by carbamoyl group(s) mono-substituted by a 1,1-dioxidodihydrobenzothienyl group.

18. A cardiomyocyte maturation promoter comprising the compound or salt according to claim 2.

19. A cardiomyocyte maturation promoter comprising the compound or salt according to claim 3.

20. A cardiomyocyte maturation promoter comprising the compound or salt according to claim 4.

21. A cardiomyocyte maturation promoter comprising the compound or salt according to claim 5.

22. A cardiomyocyte maturation promoter comprising the compound or salt according to claim 6.

23. A cardiomyocyte maturation promoter comprising the compound or salt according to claim 10.

24. A cardiomyocyte maturation promoter comprising the compound or salt according to claim 11.

25. A cardiomyocyte maturation promoter comprising the compound or salt according to claim 12.

26. A cardiomyocyte maturation promoter comprising the compound or salt according to claim 13.

27. A cardiomyocyte maturation promoter comprising the compound or salt according to claim 14.

28. A cardiomyocyte maturation promoter comprising the compound or salt according to claim 15.

29. A cardiomyocyte maturation promoter comprising the compound or salt according to claim 16.

30. A cardiomyocyte maturation promoter comprising the compound or salt according to claim 17.

31. A method for preparing a mature cardiomyocyte, which comprises a step of culturing an immature cardiomyocyte in the presence of the compound or salt according to claim 2.

32. A method for preparing a mature cardiomyocyte, which comprises a step of culturing an immature cardiomyocyte in the presence of the compound or salt according to claim 3.

33. A method for preparing a mature cardiomyocyte, which comprises a step of culturing an immature cardiomyocyte in the presence of the compound or salt according to claim 4.

34. A method for preparing a mature cardiomyocyte, which comprises a step of culturing an immature cardiomyocyte in the presence of the compound or salt according to claim 5.

35. A method for preparing a mature cardiomyocyte, which comprises a step of culturing an immature cardiomyocyte in the presence of the compound or salt according to claim 6.

36. A method for preparing a mature cardiomyocyte, which comprises a step of culturing an immature cardiomyocyte in the presence of the compound or salt according to claim 10.

37. A method for preparing a mature cardiomyocyte, which comprises a step of culturing an immature cardiomyocyte in the presence of the compound or salt according to claim 11.

38. A method for preparing a mature cardiomyocyte, which comprises a step of culturing an immature cardiomyocyte in the presence of the compound or salt according to claim 12.

39. A method for preparing a mature cardiomyocyte, which comprises a step of culturing an immature cardiomyocyte in the presence of the compound or salt according to claim 13.

40. A method for preparing a mature cardiomyocyte, which comprises a step of culturing an immature cardiomyocyte in the presence of the compound or salt according to claim 14.

41. A method for preparing a mature cardiomyocyte, which comprises a step of culturing an immature cardiomyocyte in the presence of the compound or salt according to claim 15.

42. A method for preparing a mature cardiomyocyte, which comprises a step of culturing an immature cardiomyocyte in the presence of the compound or salt according to claim 16.

43. A method for preparing a mature cardiomyocyte, which comprises a step of culturing an immature cardiomyocyte in the presence of the compound or salt according to claim 17.

* * * * *

SEQUENCE LISTING

<160> NUMBER OF SEQ ID NOS: 2

<210> SEQ ID NO 1
<211> LENGTH: 720
<212> TYPE: DNA
<213> ORGANISM: Artificial Sequence
<220> FEATURE:
<223> OTHER INFORMATION: Emerald Green Fluorescent Protein (EmGFP)

<400> SEQUENCE: 1

| atggtgagca | agggcgagga | gctgttcacc | ggggtggtgc | ccatcctggt | cgagctggac | 60 |
| ggcgacgtaa | acggccacaa | gttcagcgtg | tccggcgagg | gcgagggcga | tgccacctac | 120 |
| ggcaagctga | ccctgaagtt | catctgcacc | accggcaagc | tgcccgtgcc | ctggcccacc | 180 |
| ctcgtgacca | ccttcaccta | cggcgtgcag | tgcttcgccc | gctaccccga | ccacatgaag | 240 |
| cagcacgact | tcttcaagtc | cgccatgccc | gaaggctacg | tccaggagcg | caccatcttc | 300 |
| ttcaaggacg | acggcaacta | caagacccgc | gccgaggtga | agttcgaggg | cgacaccctg | 360 |
| gtgaaccgca | tcgagctgaa | gggcatcgac | ttcaaggagg | acggcaacat | cctggggcac | 420 |
| aagctggagt | acaactacaa | cagccacaag | gtctatatca | ccgccgacaa | gcagaagaac | 480 |

```
ggcatcaagg tgaacttcaa gacccgccac aacatcgagg acggcagcgt gcagctcgcc      540
gaccactacc agcagaacac ccccatcggc gacggccccg tgctgctgcc cgacaaccac      600
tacctgagca cccagtccgc cctgagcaaa gacccaacg agaagcgcga tcacatggtc       660
ctgctggagt tcgtgaccgc cgccgggatc actctcggca tggacgagct gtacaagtaa     720

<210> SEQ ID NO 2
<211> LENGTH: 711
<212> TYPE: DNA
<213> ORGANISM: Artificial Sequence
<220> FEATURE:
<223> OTHER INFORMATION: mCherry

<400> SEQUENCE: 2
atggtgagca gggcgagga ggataacatg gccatcatca aggagttcat gcgcttcaag        60
gtgcacatgg agggctccgt gaacggccac gagttcgaga tcgagggcga gggcgagggc     120
cgcccctacg agggcaccca gaccgccaag ctgaaggtga ccaagggtgg ccccctgccc     180
ttcgcctggg acatcctgtc ccctcagttc atgtacggct ccaaggccta cgtgaagcac     240
cccgccgaca tccccgacta cttgaagctg tccttccccg agggcttcaa gtgggagcgc     300
gtgatgaact cgaggacgg cggcgtggtg accgtgaccc aggactcctc cctgcaggac      360
ggcgagttca tctacaaggt gaagctgcgc ggcaccaact tcccctccga cggcccgta     420 atgcagaaga agaccatggg ctgggaggcc tcctccgagc ggatgtaccc cgaggacggc     480
gccctgaagg gcgagatcaa gcagaggctg aagctgaagg acggcggcca ctacgacgct    540
gaggtcaaga ccacctacaa ggccaagaag cccgtgcagc tgcccggcgc ctacaacgtc    600
aacatcaagt tggacatcac ctcccacaac gaggactaca ccatcgtgga acagtacgaa    660
cgcgccgagg gccgccactc caccggcggc atggacgagc tgtacaagta g             711
```